US008758723B2

(12) United States Patent
Yang et al.

(10) Patent No.: US 8,758,723 B2
(45) Date of Patent: Jun. 24, 2014

(54) COMPOSITIONS AND METHODS FOR CELLULAR IMAGING AND THERAPY

(75) Inventors: David J. Yang, Sugar Land, TX (US); Chang-Sok Oh, Houston, TX (US); Dong-Fang Yu, Houston, TX (US); Ali Azhdarinia, Houston, TX (US); Saady Kohanim, Sugar Land, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 2352 days.

(21) Appl. No.: 11/737,694

(22) Filed: Apr. 19, 2007

(65) Prior Publication Data

US 2007/0248537 A1 Oct. 25, 2007

Related U.S. Application Data

(60) Provisional application No. 60/745,148, filed on Apr. 19, 2006.

(51) Int. Cl.
*A61K 51/00* (2006.01)
*A61B 5/055* (2006.01)

(52) U.S. Cl.
USPC ...... 424/1.49; 424/1.69; 424/9.34; 424/9.363

(58) Field of Classification Search
USPC ............... 424/1.11, 1.69, 9.35, 9.36; 514/10, 514/14–16
See application file for complete search history.

(56) References Cited

U.S. PATENT DOCUMENTS

| | | | |
|---|---|---|---|
| 4,141,654 A | 2/1979 | Wardlaw et al. ........... 356/243.1 |
| 4,181,654 A | 1/1980 | Weitl et al. .................... 260/239 |
| 4,279,992 A | 7/1981 | Boguslaski et al. ............. 435/7 |
| 4,418,068 A | 11/1983 | Jones ............................. 514/337 |
| 4,507,466 A | 3/1985 | Tomalia et al. ............... 528/332 |
| 4,558,120 A | 12/1985 | Tomalia et al. ............... 528/363 |
| 4,568,737 A | 2/1986 | Tomalia et al. ............... 528/332 |
| 4,587,329 A | 5/1986 | Tomalia et al. ............... 528/363 |
| 4,631,337 A | 12/1986 | Tomalia et al. ............... 528/391 |
| 4,694,064 A | 9/1987 | Tomalia et al. ............... 528/332 |
| 4,713,975 A | 12/1987 | Tomalia et al. .............. 73/865.8 |
| 4,730,968 A | 3/1988 | Diperstein et al. ........... 411/178 |
| 4,732,863 A | 3/1988 | Tomasi et al. ................ 424/1.53 |
| 4,737,550 A | 4/1988 | Tomalia ........................ 525/418 |
| 4,789,542 A | 12/1988 | Goodman et al. ........... 424/1.73 |
| 4,824,659 A | 4/1989 | Hawthorne .................. 424/1.53 |
| 4,832,940 A | 5/1989 | Ege ............................... 424/1.41 |
| 4,857,599 A | 8/1989 | Tomalia et al. ............... 525/259 |
| 4,861,869 A | 8/1989 | Nicolotti et al. ............. 424/1.53 |
| 4,871,779 A | 10/1989 | Killat et al. ..................... 521/28 |
| 4,925,650 A | 5/1990 | Nosco et al. ................. 424/1.65 |
| 4,965,392 A | 10/1990 | Fritzberg et al. ............. 558/254 |
| 4,988,496 A | 1/1991 | Srinivasan et al. ........... 424/1.53 |
| 5,013,556 A | 5/1991 | Woodle et al. ............... 424/450 |
| 5,071,965 A | 12/1991 | Dunn et al. .................... 534/14 |
| 5,087,616 A | 2/1992 | Myers et al. .................... 514/21 |
| 5,108,921 A | 4/1992 | Low et al. ..................... 435/375 |
| 5,164,294 A | 11/1992 | Skold et al. ..................... 435/7.5 |
| 5,242,679 A | 9/1993 | Fritzberg et al. ............. 424/1.53 |
| 5,268,163 A | 12/1993 | Verbruggen .................... 534/14 |
| 5,279,811 A | 1/1994 | Bergstein et al. ............ 424/1.65 |
| 5,310,536 A | 5/1994 | Srinivasan .................... 424/1.65 |
| 5,356,793 A | 10/1994 | Koezuka et al. ................ 435/32 |
| 5,364,613 A | 11/1994 | Sieving et al. ................. 424/9.3 |
| 5,412,072 A | 5/1995 | Sakurai et al. ................ 530/322 |
| 5,416,016 A | 5/1995 | Low et al. ..................... 435/375 |
| 5,474,756 A | 12/1995 | Tweedle et al. ............. 424/9.363 |
| 5,517,993 A | 5/1996 | Unger et al. .................. 600/410 |
| 5,534,241 A | 7/1996 | Torchilin et al. ........... 424/9.321 |
| 5,541,287 A | 7/1996 | Yau et al. ...................... 530/317 |
| 5,601,800 A | 2/1997 | Katti et al. .................... 424/1.77 |
| 5,605,671 A | 2/1997 | Lyle et al. ..................... 424/1.41 |
| 5,605,672 A | 2/1997 | Bogdanov et al. ........... 424/1.65 |
| 5,608,060 A | 3/1997 | Axworthy et al. ............ 540/474 |
| 5,609,847 A | 3/1997 | Belinka et al. ............... 424/1.69 |
| 5,620,675 A | 4/1997 | McBride et al. ............. 424/1.69 |
| 5,635,382 A | 6/1997 | Low et al. ..................... 435/458 |
| 5,635,603 A | 6/1997 | Hansen et al. ............. 530/391.5 |
| 5,643,883 A | 7/1997 | Marchase et al. .............. 514/23 |
| 5,648,063 A | 7/1997 | Gries et al. ................. 424/9.363 |
| 5,670,132 A | 9/1997 | Griffiths et al. .............. 424/1.11 |
| 5,674,470 A | 10/1997 | Tweedle et al. ............. 424/9.363 |
| 5,684,149 A * | 11/1997 | Morrow ........................ 540/474 |
| 5,688,487 A | 11/1997 | Linder et al. ................. 424/1.65 |
| 5,688,488 A | 11/1997 | Low et al. ..................... 424/1.69 |
| 5,716,596 A | 2/1998 | Dean et al. ................... 424/1.69 |
| 5,730,968 A | 3/1998 | Butterfield et al. ........ 424/78.37 |

(Continued)

FOREIGN PATENT DOCUMENTS

CA 2 419 631 4/2002
EP 1156091 11/2001

(Continued)

OTHER PUBLICATIONS

Suzanne V.Smith, Molecular imaging with copper-64, Journal of Inorganic biochemistry, 98, 1874-1901, 2004.*
Ozaki et al., "Assesment of tumor imaging using $^{99m}$Tc-LA-beled guanine analogue," *The Journal of Nuclear Medicine*, 44(Suppl. 5):298P(Abstract 1067), 2003.
Zareneyrizi et al., "Synthesis of [$^{99m}$Tc]ethylenedicysteine-clchicine for evaluation of antiangiogenic effect," *Anti-Cancer Drugs*, 10:685-692, 1999.
PCT International Search Report and Written Opinion, issued in International Application No. PCT/US 07/82411, dated Mar. 26, 2008.
Aime et al., "Ternary Gd(III)L-HAS adducts: evidence for the replacement of inner-sphere water molecules by coordinating groups of the protein, implications for the design of contrast agents for MRI," *J. of Biol. Inorg. Chem.*, 5:488-497, 2000.

(Continued)

*Primary Examiner* — Michael G Hartley
*Assistant Examiner* — Jagadishwar Samala
(74) *Attorney, Agent, or Firm* — Parker Highlander PLLC

(57) ABSTRACT

The present invention relates generally to the fields of chemistry and radionuclide imaging. More particularly, it concerns compositions, kits and methods for imaging and therapy involving $N_4$ compounds and derivatives.

35 Claims, 29 Drawing Sheets

(56) References Cited

U.S. PATENT DOCUMENTS

| | | | |
|---|---|---|---|
| 5,820,847 A | 10/1998 | Low et al. | 424/9.1 |
| 5,830,431 A | 11/1998 | Srinivasan et al. | 424/1.69 |
| 5,834,266 A | 11/1998 | Crabtree et al. | 435/456 |
| 5,846,519 A | 12/1998 | Tweedle et al. | 424/9.363 |
| 5,847,121 A | 12/1998 | Yau et al. | 540/474 |
| 5,877,289 A | 3/1999 | Thorpe et al. | 530/387.1 |
| 5,880,281 A | 3/1999 | Argese et al. | 540/474 |
| 5,891,468 A | 4/1999 | Martin et al. | 424/450 |
| 5,908,777 A | 6/1999 | Lee et al. | 435/320.1 |
| 5,951,964 A | 9/1999 | Dean et al. | 424/1.69 |
| 5,955,053 A | 9/1999 | Marzilli et al. | 424/1.11 |
| 5,955,605 A | 9/1999 | Axworthy et al. | 540/474 |
| 5,958,374 A | 9/1999 | Meares et al. | 424/1.65 |
| 5,977,163 A | 11/1999 | Li et al. | 514/449 |
| 5,986,074 A | 11/1999 | Marzilli et al. | 534/14 |
| 6,033,884 A | 3/2000 | Woo et al. | 435/455 |
| 6,054,436 A | 4/2000 | Crabtree et al. | 514/31 |
| 6,071,490 A | 6/2000 | Griffiths et al. | 424/1.49 |
| 6,071,533 A | 6/2000 | Papahadjopoulos et al. | 424/450 |
| 6,083,741 A | 7/2000 | Hart et al. | 435/320.1 |
| 6,096,874 A * | 8/2000 | Wallace et al. | 534/10 |
| 6,113,946 A | 9/2000 | Szoka et al. | 424/486 |
| 6,143,274 A | 11/2000 | Tweedle et al. | 424/1.65 |
| 6,177,551 B1 | 1/2001 | Kasina | 534/10 |
| 6,187,286 B1 | 2/2001 | Elmaleh et al. | 424/1.73 |
| 6,197,278 B1 | 3/2001 | Blankenberg et al. | 424/1.69 |
| 6,232,295 B1 | 5/2001 | Kayyem et al. | 514/44 |
| 6,251,866 B1 | 6/2001 | Prakash et al. | 514/17 |
| 6,262,107 B1 | 7/2001 | Li et al. | 514/449 |
| 6,440,389 B1 | 8/2002 | Rabito | 424/9.6 |
| 6,521,209 B1 | 2/2003 | Meade et al. | 424/9.6 |
| 6,610,269 B1 | 8/2003 | Klaveness et al. | 424/9.1 |
| 6,613,305 B1 | 9/2003 | Collins et al. | 424/1.73 |
| 6,656,450 B2 | 12/2003 | Hubin et al. | 424/9.363 |
| 6,673,333 B1 * | 1/2004 | Meade et al. | 424/9.35 |
| 6,692,724 B1 | 2/2004 | Yang et al. | 424/1.49 |
| 6,713,046 B1 | 3/2004 | Meade | 424/9.363 |
| 6,737,247 B2 | 5/2004 | Bogdanov et al. | 435/25 |
| 7,067,111 B1 | 6/2006 | Yang et al. | 424/9.1 |
| 7,121,926 B2 | 10/2006 | Sabde | 451/41 |
| 7,223,380 B2 | 5/2007 | Yang et al. | 424/9.4 |
| 7,229,604 B2 | 6/2007 | Yang et al. | 424/9.1 |
| 7,261,875 B2 | 8/2007 | Li et al. | 424/1.69 |
| 2001/0034363 A1 | 10/2001 | Li et al. | 514/449 |
| 2001/0041189 A1 | 11/2001 | Xu | 424/488 |
| 2003/0013772 A1 | 1/2003 | Murphy et al. | 514/674 |
| 2003/0053954 A1 | 3/2003 | Meade et al. | 424/9.363 |
| 2003/0143235 A1* | 7/2003 | Cheesman et al. | 424/178.1 |
| 2003/0152512 A1 | 8/2003 | Rajopadhye et al. | 424/1.49 |
| 2003/0198597 A1 | 10/2003 | Meade et al. | 424/9.34 |
| 2003/0206865 A1 | 11/2003 | Platzek et al. | 424/9.363 |
| 2006/0241018 A1 | 10/2006 | De Haen et al. | 514/3 |
| 2007/0009428 A1* | 1/2007 | Syud et al. | 424/1.11 |

FOREIGN PATENT DOCUMENTS

| | | |
|---|---|---|
| JP | 2002-516823 | 6/2002 |
| JP | 2002-522382 | 7/2002 |
| JP | 2002-241307 | 8/2002 |
| JP | 2004-509152 | 3/2004 |
| WO | WO 91/16076 | 10/1991 |
| WO | WO 95/28966 | 11/1995 |
| WO | WO 97/33552 | 9/1997 |
| WO | WO 98/08859 | 3/1998 |
| WO | WO 99/39748 | 8/1999 |
| WO | WO 99/49901 | 10/1999 |
| WO | WO 99/56792 | 11/1999 |
| WO | WO 99/61512 | 12/1999 |
| WO | WO 00/45857 | 8/2000 |
| WO | WO 00/53233 | 9/2000 |
| WO | WO 00/61788 | 10/2000 |
| WO | WO 01/49324 | 7/2001 |
| WO | WO 01/80906 | 11/2001 |
| WO | WO 01/88106 | 11/2001 |
| WO | WO 01/91807 | 12/2001 |
| WO | WO 01/97843 | 12/2001 |
| WO | WO 02/06209 | 1/2002 |
| WO | WO 02/11677 | 2/2002 |
| WO | WO 02/24235 | 3/2002 |
| WO | WO 02/39995 | 5/2002 |
| WO | WO 02/43775 | 6/2002 |
| WO | WO 02/056692 | 7/2002 |
| WO | WO 03/009874 | 2/2003 |
| WO | WO 03/051403 | 6/2003 |
| WO | WO 2004/062574 | 7/2004 |
| WO | WO 2006/016784 | 5/2006 |

OTHER PUBLICATIONS

Anderson et al., "N,N'ethylene-di-L-cysteine (EC) complexes of Ga(III) and In(III): molecular modeling, thermodynamic stability and in vivo studies," *Nucl. Med. Biol.*, 22:165-173, 1995.

Anderson et al., Preparation, biodistribution and dosimetry of Copper-64-labeled anti-colorectal carcinoma monoclonal antibody fragments (1A3-F(ab')$_2$, *J. of Nuclear Medicine*, 36:850-858, 1995.

Angello et al., "Effect of eating on thallium-201 myocardial redistribution after myocardial ischemia," *Am J Cardiol.*, 60:528-533, 1987.

Blondeau et al., "Dimerization of an intermediate during the sodium in liquid ammonia reduction of L-thiazolidine-4-carboxylic acid," *Can. J. Chem.*, 45:49-52, 1967.

Borchardt et al., "Targeted actinium-225 in vivo generators for therapy of ovarian cancer," *Cancer Research*, 63:5084-5090, 2003.

Boschi et al., "A $cd_4/t_4$ receptor peptide ligand labeled with technetium-99m: synthesis and biological actibity," *Nuclear Med. Biol*, 27:791-795, 2000.

Botta et al., "NMR relaxometric study of new $Gd^{III}$ macrocyclic complexes and their interaction with human serum albumin," *Organic & Biomolecular Chemistry*, 2:570-577, 2004.

Brouwers et al., "Optimization of radioimmunotherapy of renal cell carcinoma: labeling of monoclonal antibody cG250 with $^{131}$I, $^{90}$I, $^{177}$Lu, or $^{186}$Re," *J. Nucl. Med.*, 45:327-337, 2004.

Canet et al., "Kinetic characterization of CMD-A2-Gd-DOTA as an intravascular contrast agent for myocardial perfusion measurement with MRI," *Magentic Resonance in Medicine*, 43:403-409, 2000.

Chappell et al., "Synthesis, characterization, and evaluation of a novel bifunctional chelating agent for the lead isotopes $^{203}$Pb and $^{212}$Pb," *Nucl. Med. Biol.*, 27:93-100, 2000.

Chmura et al., "Electrophilic chelating agents for irreversible binding of metal chelates to engineered antibodies," *J. of Controlled Release*, 78:249-258, 2002.

Corsi et al., "Inulin as a carrier for contrast agents in magnetic resonance imaging," *Chem.*, 7:64-71, 2001.

Cronin et al., "A new class of macrocycle capable of binding exogenous metals: synthesis, structure, magnetic and electrochemical properties of a Cu(II) trinuclear complex based upon 1,4,8,11-tetraazacyclotetradecane-2,3-dione [exoO(2)]cyclam," *J. Chem. Soc., Dalton Transactions*, 12:1925-1927, 1999.

Das et al., "[$^{186/188}$Re] rhenium-ethylene dicysteine (Re-Ec): preparation and evaluation for possible use in endovascular brachytherapy," *Nucl. Med. Biol.*, 27:189-197, 2000.

Davison et al., "A new class of oxotechnetium(5+) chelate complexes containing a $TcOn_2S_2$ core," *Inorg. Chem.*, 20:1629-1632, 1981.

DeNardo et al., "Enhancement of $^{67}$Cu-2IT-BAT-LYM-1 therapy in mice with human Burkitt's lymphoma (Raji) using interleukin-2," *Cancer*, 80:2576-2582, 1997.

Drapé et al., "Intraarticular diffusion of Gd-DOTA after intravenous injection in the kneww: MR imaging evaluation," *Radiology*, 188:227-234, 1993.

Edreira et al., "Optimization of the small-scale synthesis of DOTA-Tyr$^3$-octreotide," *Nuclear Medicine Communications*, 23:493-499, 2002.

Ellis and Sharma, "Co, Fe and Ga chelates for cell labelling: a potential use in PET imaging?" *Nuclear Medicine Communications*, 20:1017-1021, 1999.

Froidevaux et al., "Preclinical comparison in AR4-2J tumore bearing mice of four radiolabeled 1,4,7,10-tetraazacyclododecane-1,4,7,10-tetraacetic acid somatostatin analogs for tumor diagnosis and internal radiotherapy," *Endocrinology*, 141:3304-3312, 2000.

(56) References Cited

OTHER PUBLICATIONS

Greene and Wuts, In: *Protective Groups in Organic Synthesis*, John Wiley & Sons, New York, Chapter 1, 1999.

Gregson et al., "meso-5,5,7,12,14-Hexamethyl-1,4,8,11-tetraazacyclotetradecane as a building block in supramolecular chemistry; salts formed with 2,2'-biphenol, 4,4'-thiodiphenol, 4,4'-sulfonyldiphenol, 3-and 4-hydroxybenzoic acids, 3,5-dihydroxybenzoic acid and phenylphosphonic acid; supramolecular structures in zero, one, two and three dimensions," *Acta Crystallogr.*, B56:39-57, 2000.

Griffiths et al., "$^{90}$Y-DOTA-hLL2: an agent for radioimmunotherapy of Non-Hodgkin's lymphoma," *J. Nucl. Med.*, 44:77-84, 2003.

Gutman et al., "Time to completed redistribution of thallium-201 in exercise myocardial scintigraphy: relationship to the degree of coronary atery stenosis," *Am. Heart J.*, 106:989-995, 1983.

Henson et al., "Gadolinium-enhanced CT angiography of the circle of willis and neck," *AJNR Am. J. Neuroradiol.*, 25:969-972, 2004.

Ilgan et al., "$^{99m}$Tc-ethylenedicysteinefolate: a new tumor imaging agent. synthesis, labeling and evaluation in animals," *Cancer Biotherapy Radiopharm.*, 13:427-435, 1998.

Im et al., "Formation, properties, and characterization of a fully reduced Fe(II)Fe(II) form of spinach (and parsley) [2Fe-2S] ferredoxin with the macrocyclic complex [Cr(15-aneN(4))(H(2)O)(2)](2+) as reductant," *Inorg. Chem.*, 36:1388-1396, 1997.

Im et al., "The $Cr^{II}$reduction of [2Fe-2S] ferredoxins and site of attachment of $Cr^{III}$ using $^1$H NMR and site-directed mutagenesis," *Inorg. Chem.*, 39:1755-1764, 2000.

International Search Report mailed Sep. 25, 2006.

Kao et al., "Technetium-99m methoxyisobutylisonitrile chest imaging of small cell lung carcinoma," *Cancer*, 83:64-68, 1998.

Kitamura and Shibata, "Preparation and the covalent hydration of a hexafluoro-2,4-pentanedionatotetraaminecobalt(III) complex," *Inorganica Chimica Acta*, 203:37-42, 1993.

Kundra et al., "Noninvasive monitoring of somatostatin receptor type 2 chimeric gene transfer," *J. Nucl. Med.*, 43:406-412, 2002.

Laissy et al., "Functional evaluation of normal and ischemic kidney by means of gadolinium-DOTA enhanced TurboFLASH MR imaging: a preliminary comparison with 99Tc-MAG3 dynamic scintigraphy," *Magn. Reson. Imaging*, 12:413-419, 1994.

Lewis et al., "Conjugation of monoclonal antibodies with TETA using activated esters: biological comparison of $^{64}$Cu-TETA-1A3 with $^{64}$Cu-BAT-2IT-1A3," *Cancer Biotherapy & Radiopharmaceuticals*, 16:483-494, 2001.

Li et al., "N,N' Ethylenedi-$_L$-cysteine (EC) and its metal complexes: synthesis, characterization, crystal structures, and equilibrium constants," *Inorg. Chem.*, 35:404-414, 1996.

Li et al., "Vinyl sulfone bifunctional derivatives of DOTA allow sulfhydryl- or amino-directed coupling to antibodies. Conjugates retain immunoreactivity and have similar biodistributions," *Bioconjugate Chem.*, 13:110-115, 2002.

Luckay et al., "Synthesis and structure of a complex of bismuth(III) with nitrogen donor macrocycle," *Journal of the Chemical Society, Chem. Comm.*, 2365-2366, 1995.

Mathias et al., "Indium-111-DTPA-folate as a potential folate-receptor-targeted radiopharmaceutical," *J. Nucl. Med.*, 39:1579-1585, 1998.

Mathias et al., "Tumor-selective radiopharmaceutical targeting via receptor-mediated endocytosis of gallium-67-deferoxamine-folate," *J. Nucl. Med.*, 37:1003-1008, 1996.

Mathias et al., "Indium-111-DTPA-folate as a radiopharmaceutical for targeting tumor-associated folate binding protein (FBP)," *J. Nucl. Med.*, 38:133P, 1997.

Mathias et al., "Synthesis of Tc-99m-DTPA-folate and preliminary evaluation as a folate-receptor-targeted radiopharmaceutical," *J. Nucl. Med.*, 38:87P, 1997.

Ohtsuki et al., "Technetium-99m HYNIC-annexin V: a potential radiopharmaceutical for the in-vivo detection of apoptosis," *Eur. J. Nucl. Med.*, 26:1251-1258, 1999.

Panneerselvam et al., "(12-hydroxymethyl-5,5,7,12,14-pentamethyl-1,4,8,11-tetraazacyclo-tetradecane-N-acetato-N,N',N'',N''',0,0 ')cobalt(III) chloride perchlorate monohydrate," *Acta Crystallogr.,C* 56:659-660, 2000.

Pohost et al., "Differentiation of transiently ischemic from infarcted myocardium by serial imaging after a single dose of thallium-201," *Circulation*, 55:294-302, 1977.

Ranganathan et al., "Polymethylated DOTA ligands. 2. synthesis of rigified lanthanide chelates and studies on the effect of alkyl substitution on conformational mobility and relaxivity," *Inorg. Chem.*, 41:6856-6866, 2002.

Ruegg et al., "Improved in vivo stability and tumor targeting of bismuth-labeled antibody," *Cancer research*, 50:4221-4226, 1990.

Schechter et al., "Assessment of epidermal growth factor receptor with $^{99m}$Tc-ethylenedicysteine-C225 monoclonal antibody," *Anticancer Drugs*, 14:49-56, 2003.

Sharkey et al., "Radioimmunotherapy of Non-Hodgkin's lymphoma with $^{90}$Y-DOTA humanized anti-CD22 IgG ($^{90}$Y-Epratuzumab): do tumor targeting and dosimetry predict therapeutic response?" *J. Nucl. Med.*, 44:2000-2018, 2003.

Smith et al., "Radiochemical investigations of $^{177}$Lu-DOTA-8-Aoc-BBN[7-14]$NH_2$: an in vitro/in vivo assessment of the targeting ability of this new radiopharmaceutical for PC-3 human prostate cancer cells," *Nuclear Medicine and Biol.*, 30:101-109, 2003.

Song et al., "Prognostication of recovery in patients with acute ischemic stroke through the use of brain SPECT with $^{99m}$Tc-labeled metronidazole," *Stroke*, 34:982-986, 2003.

Srivastava et al., "Comparative evaluation of chelating agents on the mobilization cadmium: a mechanistic approach," *J. Toxicology and Environmental Health*, 47:173-182, 1996.

Stein et al., "Radioimmunotherapy of a human lung cancer xenograft with monoclonal antibody RS7: evaluation of $^{177}$Lu and comparison of its efficacy with that of $^{90}$Y and residualizing $^{131}$I," *J. Nucl. Med.*, 42:967-974, 2001.

Surma et al., "Usefulness of 99Tcm-N,N'-ethylene-1-dicysteine complex for dynamic kidney investigations." *Nucl. Med. Comm.*, 15:628-635, 1994.

Van Nerom et al., "First experience in healthy volunteers with technetium-99m L.L-ethylenedicysteine, a new renal imaging agent," *Eur. J. Nucl. Med.*, 20:738-746, 1993.

Van Nerom et al., "Comparative evaluation of Tc-99m L,L-ethylenedicysteine and Tc-99m MAG3 in volunteers," *Eur. J. Nucl. Med.*, 16:417, 1990.

Verbruggen et al., "Evaluation of Tc-99m L, L-ethylenedicysteine as a potential alternative to Tc-99m MAG3," *Eur. J. Nucl. Med.*, 16:429, 1990.

Verbruggen et al., "Technetium-99m-L,L-ethylenedicysteine: a renal imaging agent. I. labeling and evaluation in animals," *J. Nucl. Med.*, 33:551-557, 1992.

Vogler et al., "Pre-clinical evaluation of gadobutrol: a new, neutral, extracellular contrast agent for magnetic resonance imaging," *Eur. J. Radiol.*, 21:1-10, 1995.

Vriens et al., "The use of technetium $^{99m}$Tc annexin V for in vivo imaging of apoptosis during cardiac allograft rejection," *J. Thorac. Cardiovasc. Surg.*, 116:844-853, 1998.

Wang et al., "[$Cu(L)Mn(N_3)_2$]n: the first complex containing both macrocyclic oxamido and alternate (mu-1,1 and mu-1,3) azido bridges," *Inorg. Chem.*, 43:852-854, 2004.

Wu et al., "High-resolution microPET imaging of carcino-embryonic antigen-positive xenografts by using a copper-64-labeled engineered antibody fragment," *Proc. Nat. Acad. Sci. USA*, 97:8495-8500, 2000.

Wu et al., "Using Tc-99m DMSA renal cortex scan to detect renal damage in women with type 2 diabetes," *J. Diabetes Complications*, 17:297-300, 2003.

Wu et al., "Investigations of N-linked macrocycles for 111In and 90Y labeling of proteins," *Nucl. Med. & Biol.*, 19:239-244, 1992.

Yang et al., "Assessment of antiangiogeneic effect using $^{99m}$Tc-EC-endostatin," *Cancer Biotherapy Radioharm*, 17:233-246, 2002.

Yang et al., "Imaging with $^{99m}$Tc ECDG targeted at the multifunctional glucose transport system: feasibility study with rodents," *Radiology*, 226:465-473, 2003.

(56) References Cited

OTHER PUBLICATIONS

Yang et al., "In vivo and in vitro measurement of apoptosis in breast cancer cells using $^{99m}$Tc-EC-annexin V," *Cancer Biotherapy Radiopharm.*, 16:73-84, 2001.

Yang et al., "Noninvasive assessment of tumor hypoxia with $^{99m}$Tc-labeled metronidazole," *Pharm Res.*, 16:743-750, 1999.

Yang et al., "Targeted molecular imaging in oncology," *Annals of Nuclear Medicine*, 20:1-11, 2006.

Zareneyrizi et al., "Synthesis of $^{99m}$Tc-ethylenedicysteine-colchicine for evaluation of antiangiogenic effects," *Anti-Cancer drugs*, 10:685-692, 1999.

Zhang et al., "A ferromagnetically coupled $CrCu_3$ tetramer and $GdCu_4$ pentamer with a $[15]N_4$ macrocylic ligand incorporating an oxamido bridge," *Inorg. Chem.*, 42:1462-1466, 2003.

Zhao et al., "Effects of Dextranation on the pharmacokinetics of short peptides. a PET study on mEGF," *Bioconjugate Chem.*, 10:938-946, 1999.

Zhou et al., "Efficient intracellular delievery of oligonucleotides formulated in folate receptor-targeted lipid vesicles," *Bioconjugate Chem.*, 13:1220-1225, 2002.

U.S. Appl. No. 10/627,763, filed Jul. 28, 2003, Lin.

U.S. Appl. No. 11/737,694, filed Apr. 19, 2007, Yang.

U.S. Appl. No. 60/828,347, filed Oct. 5, 2006, Yang.

Abrams et al., "Technetium-99m-human polyclonal IgG radiolabeled via the hydrazino nicotinamide derivative for imaging focal sites of infection in rats," *J. Nucl. Med.*, 31:2022-2028, 1990.

Alauddin and Conti, "Synthesis and preliminary evaluationo f 9-(4-{18F -Fluoro-3-Hydroxymethylbutyl)guanine ([18F]FHBG): a new potential imaging agent for viral infection and gene therapy," *Nucl. Med. Biol.*, 25:175-180, 1998.

Alauddin et al., "Evaluation of 9-[(3-18F]-fluoro-1-hydroxy-2-propoxy)methyl guanine ([18F]-FHPG) in vitro and in vivo as probe for PET imaging of gene incorporation and expression in tumors," *Nucl. Med. Biol.*, 26:371-376, 1999.

Alauddin et al., "Receptor mediated uptake of a radiolabeled contrast agent sensitive to β-galactosidase activity," *Nucl. Med. Biol.*, 30:261-265, 2003.

Alauddin et al., "Synthesis of 9-[(3-18F]-fluoro-1-hydroxy-2-propoxy)methyl guanine ([18F]-FHPG): a potential imaging agent of viral infection and gene therapy using PET," *Nucl. Med. Biol.*, 23:787-792, 1996.

Alper et al., "Assessment of renal functional changes following transurethral prostatectomy suing tc-99m ethylenedicysteine," *J. Nuclear Med.*, 37:289P, Abstract No. 1292, 1996.

Anderson and Welch, "Radiometal-labeled agents (non-technetium) for diagnostic imaging," *Chem. Rev.*, 99:2219-2234, 1999.

Anderson et al., "Copper-64-labeled antibodies for PET imaging," *J. Nucl. Med.*, 33:1685-1691, 1992.

Antony, "Folate receptors," *Ann. Rev.*, 16:501-521 1996.

Aoi et al., "Globular carbohydrate macromolecule 'sugar balls' 3. 'radical-growth polymerization' of sugar-substituted α-amino acid N-carboxyanhydrides (glycoNCAs) with a dendritic initiator," *Tetrahedron, Elsevier Science Publishers*, 53(45):15415-15427 1997.

Appelbaum et al., "The use of radiolabeled anti-CD33 antibody to augment marrow irridation prior to marrow transplantation for acute myelogenous leukemia," *Transplantation*, 54(5):829-833, 1992.

Auzeloux et al., "Technetium-99m radiolabelling of an N-aminoalkyl-benzamide nitrido-and oxo-technetium bis(aminoethanethiol) derivative syntesis and biological results. Potential melano tracer agents," *Journal of Labelled Compounds and Radiopharmaceuticals*, 42:567-579, 1999.

Baidoo and Lever, "Evaluation of a diaminedithiol-based bifunctional chelate for labeling small molecules with $^{99m}$Tc," *Technetitum and Rhenium in Chemsitry and Nuclear Medicine*, 1990.

Baidoo et al., "Synthesis of a new diaminedithiol bifunctional chelate for the preparation of nuetral technetium complexes," *J. Nuclear Med.*, 31:806, Abstract No. 414, 1990.

Bajorin et al., "Phase I trial of anti-GD3 mouse monoclonal antibody (Mab) and IL-2 in patients with melanoma," *Proc. Annu. Meet. Am. Soc. Clin. Oncol.*, 7:250, A967, 1988.

Bakker et al., "Receptor scintigraphy with a radioiodinated somatostatin analogue: radiolabeling, purification, biologic activity and in vivo application in animals," *J. Nucl. Med.*, 31:1501-1509, 1990.

Bar-Sever et al., "Comparison of living related donor and recipient renograms in predicting the early postransplantation course," *J. Nuclear Med.*, 37:292P, Abstract No. 1305, 1996.

Baselga et al., "Phase I studies of anti-epidermal growth factor receptor cheimeric antibody C225 alone and in combination with cisplatin," *J. Clinical Oncology*, 18(4):904-914, 2000.

Baselga et al., "Recombinant humanized anti-HER2 antibody (herceptin) enhances the antitumor activity of paciltazel and doxorubicin against HER2/new overexpressing human breast cancer xenografts," *Cancer Research*, 58:2825-2831, 1998.

Becker et al., "Analysis of E-cadherin in diffuse-type gastric cancer using a mutation-specific monoclonal antibody," *American Journal of Pathology*, 155(6):1803-1809, 1999.

Benns et al., "Tailoring new gene delivery designs for specific targets," *Journal of Drug Targeting*, 8(1), Database Medline on STN International, Accession No. 2000222278, 2 pages, 2000.

Benveniste and Davies, "Aminoglycoside antibiotic-inactivating enzymes in actinomycetes similar to those present clinical isolates of antibiotic-resistant bacteria," *Proc. Natl. Acad. Sci. USA*, 70:2276-2280, 1973.

Bertolini et al., "Angiogenic growth factors and endostatin in non-Hodgkin's lymphoma," *Br. J. Haematol.*, 106:504-9, 1999.

Blair and Ghose., "Linkage of cytotoxin agents to immunoglobulins," *Journal of Immunological Methods*, 59:129-143 1983.

Blakenberg et al., "Imaging of apoptosis (programmed cell death) with $^{99m}$Tc annexin V.," *J. Nucl. Med.*, 40:184-191 1999.

Blankenberg et al., "Apoptosis: the importance of nuclear medicine," *Nucl. Med. Comm.*, 21:241-250, 2000.

Blankenberg et al., "In vivo detection and imaging of phosphatidylserine expression during programmed cell death," *Proc. Natl. Acad. Sci. USA*, 95:6349-6354, 1998.

Block, "Poly(g-benzyl-L-glutamate) and other glutamic acid containing polymers," Gordon and Breach Science Publishers, New York, 11-31, 1983.

Boersma et al., "Quantification of apoptotic cells with fluorescein isothiocyanate-labeled annexin V in Chinese hamster ovary cell cultures treated with cisplatin," *Cytometry*, 24:123-130, 1996.

Bohdiewicz, "Indium-III satumomab pendetide: the first FDA-approved monoclonal antibody for tumor imaging," *J. Nuclear Medicine Technology*, 26(3):155-163, 1998.

Bormans et al., "Synthesis and biological characteristics of the fourn stereoisomers of 99mTc-N, N'-bis-(mercaptoacetyl)2,3-diaminopropanoate," *Int. J. Rad. Appl. Instrum. B.*, 17(5);499-506, 1990.

Borodina et al., "Metabolic network analysis of *Streptomyces tenebrarius*, a *Streptomyces* species with an active entner-doudoroff pathway," *Appl. Environ. Microb.*, 71:2294-2302, 2005.

Brechbiel et al., "Synthesis of 1 (P-isothiocyanatobenzyl) derivatives of DTPA and EDTA: antibody labeling and tumor-imaging studies," *Inorg. Chem.*, 25:2772-2781, 1986.

Brogi et al., "Hypoxia-induced paracrine regulation pf vascular endothelial growth factor receptor expression," *J. Clin. Invest.*, 97(2):469-476, 1996.

Brokx et al., "Designing peptide-based scaffolds as drug delivery vehicles," *Science*, 78(1-3):115-123, 2002.

Budihardjo et al., "Biochemical pathways of caspase activation during apoptosis," *Annu. Rev. Cell Dev. Biol.*, 15:269-290, 1999.

Burgen, "Targets of drug action," *Ann. Rev. Pharmacol. Toxicol.*, 40:1-16, 2000.

Burian et al., "Angiogenic factors in laryngeal carcinomas: do they have prognostic relevance?," *Acta Otolaryngol.*, 119:289-292, 1999.

Bush et al., "Definitive evidence for hypoxic cells influencing cure in cancer therapy," *Br J Cancer*, (Suppl. III) 37:302-306 1978.

Cafaggi et al., "Synthesis and antitumor activity of a new cis-diammineplatinum (III) complex containing procaine hydrochloride," *Anticancer Research*, 12:2285-2292, 1992.

(56) References Cited

OTHER PUBLICATIONS

Cammisuli et al., "SDZ 281-977: a modified partial structure of lavendustin A that exerts potent and selective antiproliferative activities in vitro and in vivo," *Int J Cancer*, 65:351-359, 1996.
Campbell et al., "Folate-binding protein is a marker for ovarian cancer," *Cancer Res*, 51:5329-5338, 1991.
Cao, "Therapeutic potentials of angiostatin in the treatment of cancer," *Haematologica*, 84:643-650, 1999.
Chakrabarti et al., "Interaction of the antitumor antibiotic chromomycin A3 with glutathione, a sulfhydryl agent, and the effect upon its DNA binding properties," *Biochemical Pharmacology*, 56:1471-1479, 1998.
Chapman et al., "Therapeutic antibody fragments with prolonged in vivo half-lives," *Nature Biotech.*, 17:780-783, 1999.
Chen et al., "Biological and pharmacokinetic evaluation of tc-99m ma2g2-b: a potential renal agent," *J. Nuclear Med.*, 35:263P, Abstract No. 1082, 1994.
Cherif et al., "Rapid synthesis of [18F]Fluoro-1-(2'-Nitro-1'-Imidazolyl)-2-Propanol ([$^{18}$F]Fluoromisonidazole)," *Pharm Res.*, 11:466-469, 1994.
Cleynhens et al., "Synthesis and biological evaluation in mice of a monoamide derivative of tc-99m-l,l-ec," *J. Nuclear Med.*, 38:186P, Abstract No. 799, 1997.
Collier et al. "Immunoscintigraphy performed with In-111-labeled CYT-103 in the management of colorectal cancer: comparison with CT," *Radiology*, 185:179-186, 1992.
Coney et al., "Chimeric murine-human antibodies directed against folate binding receptor are efficient mediators of ovarian carcinoma cell killing," *Cancer Res*, 54:2448-2455, 1994.
Connett et al., "Maximum tolerated dose and large tumor radioimmunotherapy studies of 64Cu-labeled monoclonal antibody 1A3 in a colon cancer model," *Clin. Cancer Res.*, 5(10 Suppl):3207s-3212s, 1999.
Connett et al., "Radioimmunotherapy with a 64Cu-labeled monoclonal antibody: a comparison with 67Cu," *Proc. Natl. Acad. Sci. USA*, 93:6814-6818, 1996.
Connors, "Anticancer drug development: the way forward," *The Oncologist*, 1:180-181, 1996.
Co-Pending U.S. Appl. No. 10/703,405, filed Nov. 7, 2003.
Co-Pending U.S. Appl. No. 10/732,919, filed Dec. 10, 2003.
Corlija et al., "Contribution of radiolytically induced dissociation of 99mtc-d, 1-hmpao in aqueous solutions," *J. Nuclear Med.*, 31:806, Abstract No. 413, 1990.
Craig et al., "Renal outcomes for children on year after urinary tract infection," *J. Nuclear Med.*, 37:46P, Abstract No. 175, 1996.
Culver et al., "In vivo gene transfer with retroviral vector-producer cells for treatment of experimental brain tumors," *Science*, 256:1550-1552, 1992.
Cutler et al., "Dosimetry of copper-64-labeled monoclonal antibody 1A3 as determined by PET imaging of the torso," *J. Nucl. Med.*, 36:2363-2371, 1995.
Dagli et al., "Analysis of the complete dynamic scan data for camera-based determination of renal function," *J. Nuclear Med.*, 37:91P, Abstract No. 354, 1996.
de Klerk et al., "Aspirin versus captopril renography in the diagnosis of renal artery stenosis," *J. Nuclear Med.*, 37:289P, Abstract No. 1291, 1996.
Deguchi et al., "Retention of biologic activity of human epidermal growth factor following conjugation to a blood-brain barrier drug delivery vector via an extended poly(ethylene glycol) linker," *Bioconjugate Chem.*, 10:32-37, 1999.
DeNardo et al., "Pharmacokinetics of chimeric L6 conjugated to indium 111- and yttrium-90-DOTA-peptide in tumor-bearing mice," *J. Nuclear Medicine*, 36:829-836, 1995.
DeNardo et al., "Yttrium-90/indoum-111-DOTA-peptide-chimeric L6: Pharmacokinetics, dosimetry and initial results in patients with incurable breast cancer," *Anticancer Research*, 17(3B):1735-1744, 1997.

Deutsch et al., "Synthesis of congeners and prodrugs, water-soluble prodrugs of taxol with potent antitumor activity," *J. Med. Chem.*, 32:788-792, 1989.
Deveraux and Reed, "IAP family proteins-suppressors of apoptosis," *Genes and Development*, 13:239-252, 1999.
Dewanjee et al., "Labeling antisense oligodeoxynucleotide (on) with tc-99m and hybridization with c-myc oncogene mrna in p388 leukemic cells," *J. Nuclear Med.*, 35:263P, Abstract No. 1081, 1994.
Dezutter et al., "Preparation and biological evaluation of technetium-$^{99m}$-L,L-propylenedicysteine" *J. of Labelled Cpd. Radiopharm.*, 42:553-565 1999.
Diamond et al., "Glycolysis in quiescent cultures of 3T3 cells. Stimulation by serum, epidermal growth factor, and insulin in intact cells and persistence of the stimulation after cell homogenization," *J. Biol. Chem.*, 253:866-871, 1978.
Dische, "A review of hypoxic-cell radiosensitization," *Int J Radiat Oncol Biol Phys*, 20:147-152, 1991.
Divgi et al., "Phase I and imaging trial of indium 111-labeled anti-epidermal growth factor receptor monoclonal antibody 225 in patients with squamous cell lung carcinoma," *J. National Cancer Institute*, 83(2):97-104, 1991.
Drobnik et al., "Soluble synthetic polymers in biological systems," *Adv. Polym. Sci.*, 57:1-50, 1984.
Dunn et al., "Receptor-mediated endocytosis of epidermal growth factor by hepatocytes in the perfused rat liver: ligand and receptor dynamics," *J. Cell Biol.*, 98:2148-2159, 1984.
Eary et al., "Radiochemistry of halogenated antibodies," *Antibodies in Radiodiagnosis and Therapy*, Boca Ratan, Florida, CPC Press, 83-100, 1988.
Eiseman et al., "Plasma pharmacokinetics and tissue distribution of paclitaxel in CD2F1 mice," *Cancer Chemother. Pharmacol.*, 34:465-471, 1994.
Eisenhut et al., "Synthesis and In Vivo Testing of a bromobutyl substituted 1,2-Dithia-5,9-diazacycloundecane: a versatile precursor for new $^{99m}$Tc-bis(aminoethanethiol) complexes," *Nucl. Med. Biol.*, 16:805-811, 1989.
Ennis et al., "Anti-epidermal growth factor receptor antibodies inhibit the autocrine-stimulated growth of MDA-468 human breast cancer cells," *Mol. Endocrinology*, 3(11):1830-1838, 1989.
Eshima et al., "Evaluating the role of protein binding on the renal extraction of tc-99m tubular agents utilizing an isolated perfused rat kidney model," *J. Nuclear Med.*, 37:47P, Abstract No. 178, 1996.
Ethier, "Growth factor synthesis and human breast cancer progression," *J. Natl. Cancer Inst.*, 87(13):964-973, 1995.
Fan et al., "Antitumor effect of anti-epidermal growth factor receptor monoclonal antibodies plus cis-diamminedichloroplatinum on well established A431 cell xenografts," *Cancer Research*, 53:4637-4642, 1993.
Fan et al., "Blockade of epidermal growth factor receptor function by bivalent and monovalent fragments of 225 anti-epidermal growth factor receptor monoclonal antibodies," *Cancer Research*, 53:4322-4328, 1993.
Fanciulli et al., "Glycolysis and growth rate in normal and in hexokinase-transfected NIH-3T3 cells," *Oncology Res.*, 6:405-409, 1994.
Fang et al., "Involvement of p21 Wafl in mediating inhibition of paclitaxel-induced apoptosis by epidermal growth factor in MDA-MB-468 human breast cancer cells," *Anticancer Research*, 20(1A):103-112, 2000.
Fidler et al., "The biology of cancer invasion and metastasis," *Adv. Cancer Res.*, 28:149-250, 1987.
Foa et al., "Taxol (paclitaxel): a novel anti-microtubule agent with remarkable anti-neoplastic activity," *J. Clin. Lab. Res.*, 24:6-14, 1994.
Frankel et al., "Targeted toxins," *Clin. Cancer Res.*, 6:326-334, 2000.
Franklin et al., "New anti-lung-cancer antibody cluster 12 reacts with human folate receptors present on adenocarcinoma," *Int J Cancer-Supplement*, 8:89-95, 1994.
Frisch and Screaton, "Anoikis mechanisms," *Curr. Opin. Cell Biol.*, 13:555-562 2001.
Fuertges et al., "The clinical efficacy of poly(ethylene glycol)-modified poriens," J. Controlled Release, 11:139-148, 1990.

(56) References Cited

OTHER PUBLICATIONS

Fuller et al., "A procedure for the facile synthesis of amino-acid N-carboxyanhydride," *Biopolymers*, 15:1869, 1976.
Gabizon, "Selective tumor localization and improved therapeutic index of anthracyclines encapsulated in long-circulating liposomes," *Cancer Research*, 52:891-896, 1992.
Gambhir et al., "A mutant herpes simplex virus type 1 thymidine kinase reporter gene shows improved sensitivity for imaging reporter gene expression with positron emission tomography," *Proc. Natl. Acad. Sci., USA*, 97(6):2785-2790, 2000.
Gambhir et al., "Imaging adenoviral-directed reporter gene expression in living animals with positron emission tomography," *Proc. Natl. Acad. Sci. USA*, 96:2333-2338, 1999.
Gambhir et al., "Imaging of adenoviral-directed herpes simplex virus type 1 thymidine kinase reporter gene expression in mice with radiolabeled ganciclovir.," *J. Nucl. Med.*, 39:2003-2011, 1998.
Garayoa et al., "Hypoxia-inducible factor-I (HIF-1) up-regulates adrenomedullin expression in human tumor cell lines during oxygen deprivation: a possible promotion mechanism of carcinogenesis," *Molecular Endocrinology*, 14:848-862, 2000.
Gariepy and Kawamura "Vectorial delivery of macromolecules into cells using peptide-based vehicles," *Trends in Biotechnology*, 19(1):21-28 2001.
Ginobbi et al., "Folic acid-polylysine carrier improves efficacy of c-myc antisense oligodeoxynucleotides on human melanoma (M14) cell," *Anticancer Research*, 17:29-36, 1997.
Girard, "Mechanisms by which carbohydrates regulate expression genes for clycolytic and lipogenic enzymes," *Ann. Rev. Nutr.*, 17:325-352, 1997.
Giraud et al., "Application to a cartilage targeting strategy: Synthesis and in vivo biodistribution of $^{14}$C-labelled quaternary ammonium-glucosamine conjugates," *Bioconjug. Chem.*, 11:212-218, 2000.
Goh et al., "Growth hormone promotion of tubulin polymerization stabilizes the microtubule network and protects against colchicine-induced apoptosis," *Endocrinology*, 139:4364-4372, 1998.
Goldenberg et al., "Imaging of human tumor xenografts with and indim-111-labeled anti-epidermal growth factor receptor monoclonal antibody," *J. National Cancer Institute*, 81:1616-1625, 1989.
Goldenberg, "Monoclonal antibodies in cancer detection and therapy," *Am. J. Med.*, 94:297-312, 1993.
Goldsmith et al., "Somatostatin receptor imaging in lymphoma," *Sem Nucl Med*, 25:262-271, 1995.
Goldsmith, "Receptor imaging: Competitive or complementary to antibody imaging,"*Sem Nucl Med.*, 27:85-93, 1997.
Goldspeil, "Pharmaceutical issues: preparation, administration, stability, and compatibility owth other medications," *Ann. Pharocother.*, 28:S23-S26, 1994.
Gonda, "Aerosols for delivery of therapeutic and diagnostic agents to the respiratory tract," *Critical Reviews in Therapeutic Drug Carrier Systems*, 6(4):273-313, 1990.
Green and Evan, "A matter of life and death," *Cancer Cell*, 1:19-30, 2002.
Green and Wuts, Chapter 2, 1999.
Green and Wuts, Chapter 4, 1999.
Green and Wuts, Chapter 5, 1999.
Green and Wuts, Chapter 6, 1999.
Green and Wuts, Chapter 7, 1999.
Greenfield et al., "In vitro evaluation of immunoconjugates prepared by linking mitomycin C to monoclonal antibodies via polyglutamic acid carriers," *Antibody, Immunoconjugates, and Radiopharmaceuticals*, 2(3):201-216, 1989.
Greenwald et al., "Drug delivery systems: water soluble tazol 2'-poly(ethylene glycol) ester prodrugs-design and in vivo effectiveness," *J. Med. Chem.*, 39:424-431, 1996.
Guo and Gallo, "Selective protection of 2', 2'-difluorodeoxcytidine (Gemcitabine),"*J Org Chem*, 64:8319-8322, 1999.
Guozheng and Boli, "A new potential renal imaging agent 99mtcn-ec," *J. Labelled compounds and Radiopharmaceuticals*, XXXVII:797-798, 1995.

Hadley et al.,"Magnetic resonance imaging in acute head injury," *Clin. Rad.*, 39:131-139, 1988.
Halpern et al., "Stability, characterization, and kinetics of In-labeled monoclonal antitumor antibodies in normal animals and nude mouse human tumor models," *Cancer Research*, 43:5347-5355, 1983.
Harada et al., "Insulin-induced egr-1 expression in chinese hamster ovary cells in insulin receptor an dinsulin receptor substrate-1 phosphorylation-independent," *J. Biol Chem.*, 270:26632-26638, 1995.
Hay et al., "Hypoxia-selective antitumor agents. Bis(nitroimidazolyl)alkanecarboxamides: a new class of hypoxia-selective cytotoxins and hypoxic cell radiosensitizers," *J Med. Chem.*, 37:381-391, 1994.
Hermann and Patel, "Adaptive recognition by nucleic acid aptamers," *Science*, 287:820-825, 2000.
Hermanson, "Amine detection reagents," *Bioconjugate Techniques*, San Diego, Academic Press, 112-114, 1996.
Hermanson, "Ellman's assay for the determination of sulfhydryls," *Bioconjugate Techniques*, Sand Diego, Academic Press, 88-90, 1996.
Hibi et al., "PGP9.5 as a candidate tumor marker for non-small-cell lung gancer," *American Journal of Pathology*,155(3):711-715, 1999.
Hirsch et al., "PK11195, a ligand of the mitochondrial benzodiazepine receptor, facilitates the induction of apoptosis and reverses Bcl-2-mediated cytoprotection," *Experimental Cell Research*, 241:426-434, 1998.
Hjarnaa et al., "CHS 828, a novel pyridyl cyanoguanidine with potent antitumor activity in vitro and in vivo," *Cancer Res.*, 59:5751-5757, 1999.
Hnatowich et al., "Radioactive labeling of antibody: a simple and efficient method," *Science*, 220:613-615, 1983.
Hoelscher et al., "Effects of very high antibiotic concentrations on human intervertebral disc cell proliferation, viability, and metabolism in vitro," *Spine*, 25:1871-1877, 2000.
Hoes et al., "Optimization of macromolecular prodrugs of the antitumor antibiotic adriamycin," *J. Controlled Release*, 2:205-213, 1985.
Holm et al., "Folate receptor of human mammary adenocarcinoma," *APMIS*, 102:413-419, 1994.
Holmes et al., "Current status oc clinical trials with paclitaxel and docetael, taxane anticancer agents: basic science and current status," *American Chemical Society*, Washington, DC, 31-57, 1995.
Honess et al., "Preclinical evaluation of the novel hypoxic marker $^{99m}$Tc-HL91 (prognox) in murine and xenograft systems in vivo," *Int. J. Radiation Oncology Biol. Phys.*, 42:731-735, 1998.
Hostetler and Hall, "Inhibition of kidney lysosomal phospholipases A and C by aminoglycoside antibiotics: possible mechanism of aminoglycoside toxicity," *PNAS*, 79:1663-1667, 1982.
Hsueh and Dolnick, "Altered folate-binding protein mRNA stability in KB cells grown in folate-deficient medium," *Biochem. Pharmacol.*, 45:2537-2545, 1993.
Hu, "Neomycin inhibits angiogenin-induced angiogenesis," *Proc. Natl. Acad. Sci. USA*, 95:9791-9795, 1998.
Hudecz et al., "Influence of carrier on biodistibution and in vitro cytotoxicity of methotexate-branched polypeptide conjugates," *Bioconjugate Chemistry*, American Chemical Society, 4(1):25-33, 1993.
Inoue et al., "Evaluation of In-111 DTPA-paclitaxel scintigraphy to predict response on murine tumors to paclitaxel," *Annals of Nuclear Medicine*, 13(3):169-174, 1999.
Inoue et al., "Paclitaxel enhances the effects of the anti-epidermal growth factor receptor monoclona antibody ImClone C225 in mice with metastatic human bladder transitional cell carcinoma," *Clinical Cancer Res.*, 6:4874, 4884, 2000.
Inoue et al., "The prognostic value of angiogenesis factor expression for predicting recurrence and metastasis of bladder cancer after neoadjuvant chemotherapy and radical cystectomy," *Clin. Cancer Res.*, 6:4866-4873, 2000.
Ionov et al., "Mutational inactivation of the proapoptotic gene BAX confers selective advantage during tumor clonal evolution," *Proc. Natl. Acad. Sci., USA*, 97(20):10872-10877, 2000.
Irie and Morton "Regression of cutaneous metastic melanoma by inralesional injection with human monoclonal antibody to ganglioside GD2," *Proc. Natl. Acad. Sci., USA*, 83:8694-8698, 1986.

(56) References Cited

OTHER PUBLICATIONS

Ito et al., "PET and planar imaging of tumor hypoxia with labeled metronidazole," *Acad. Radiol.*, 13:598-609, 2006.
Itoh et al., "Graphic (patlak) method in tc-99m-mag3 renal scintigraphy: noninvasive calculation of extraction fraction (ef) and renal plasma flow (RPF)," *J. Nuclear Med.*, 37:291P, Abstract No. 1300, 1996.
Iyer et al., "8-[18F]Fluoropenciclovir: an improved reporter probe for imaging HSV1-tk reporter gene expression in vivo using PET," *J. Nucl. Med.*, 42(1):96-105, 2001.
Jamar et al., "Clearance of the new tubular agent Tc-99m L,L-ethylenedicysteine: Estimation by a simplified method," *J Nucl Med*, 34:129P, 1993.
Jamar et al., "Clinical evaluation of Tc-99m L,L-ethylenedicysteine, a new renal tracer, in transplanted patients," *J Nucl Med*, 34:(Abstract 514), 1993.
Jeppesen et al., Impact of polymer tether length on multiple ligand-recepotor bond formation, *Science*, 293:465-468, 2001.
Jiang et al., "3-(Iodoacetamido)-benzoylurea: a novel cancericidal tubulin ligand that inhibits microtubule polymerization, phosphorylates bcl-2, and induces apoptosis in tumor cells," *Cancer Res.*, 58:5389-5395, 1998.
Jiang et al., "Antitumor activity of didemnin B in the human tumor stem cell assay," *Cancer Chemother Pharmacol*, 11:1-4, 1983.
John et al., "Tc-99m labeled ethylenediamines: quest for sigma receptor chelates," *J. Nuclear Med.*, 38:186P, Abstract No. 798, 1997.
Jones and Mayer, "Glucose metabolism in the rat small intestine: the effect of glucose analogues on hexokinase activity," *Biochem. J*, 132:125-128, 1973.
Jurisson et al., "Potential technitium small molecule radiopharmaceuticals," *Chem. Rev.*, 99:2205-2218, 1999.
Kabasakal et al., "Clinical comparison of technetium-$^{99m}$-ec, technetium-$^{99m}$-MAG3 and iodine-131-OIH in renal disorders,"*J. Nucl. Med.*, 36(2):224-228, 1995.
Kabasakal et al., "Evaluation of technetium-99m-ethylenedicysteine in renal disorders and determination of extraction ratio, " *J. Nucl. Med.*, 36(8):1398-1403, 1995.
Kabasakal et al., "Prospective validation of single plasma sample $^{99m}$Tc-ethylenedicysteine clearance in adults," *J. Nucl. Med.*, 40:429-431, 1999.
Kabasakal et al., Simplified technetium-$^{99m}$-EC clearance in adults from a single plasma sample, *J. Nuclear Med.*, 38:1784-1786, 1997.
Kabasakal. "Technetium-99m ethylene dicysteine: a new renal tubular function agent," *Eur. J Nucl. Med.* 27:351-357, 2000.
Kanazawa et al., "19F NMR of 2-deoxy-2-fluro-D-glucos for tumor diagnosis in mice. An NDP-bound hexose analog as a new NMR target for imaging," *NMR in Biomed.*, 10:35-41, 1997.
Kanvinde et al., "Technetium-99m-γ-pyrones: a new class of tc-99m cationic complexes," *J. Nuclear Medicine*, 31:908, Abstract, 1990.
Kao et al., "Detection of esophageal carcinoma susing Tc-99m MIBI SPECT imaging," *Clin. Nucl. Med.*, 19(12):1069-1074, 1994.
Kao et al., "Relationship of alveolar permeability and lung inflammation in patients with active diffuse infiltrative lung disease detected by 99Tcm-DTPA radioaerosol inhalation lung scintigraphy and quantitative 67Ga lung scans," *Nucl. Med. Commun.*, 15(10):850-854, 1994.
Kao et al., "Role of radioisotope penile plethysmigraphy in the evaluation of penile hemodynamic of impotent patients," *J. Nuclear Med.*, 37:292P, Abstract No. 1304, 1996.
Kao et al., "Tc-99m MIBI uptake in breast carcinoma and axillary lymph node metastases," *Clin. Nuc. Med.*, 19(10):898-900, 1994.
Kato and Sugiyama, "Targeted delivery of peptides, proteins, and genes by receptor-mediated endocytosis," *Critical Reviews in Therapeutic Drug Carrier Systems*, 14(3):287-331, 1997.
Kato et al., "A novel method of conjugation of daunomycin with antibody with a poly-L-glutamic acid-a-fetoprotien antibody-daynomycin conjugate," *J. Med. Chem.*, 27:1602-1607, 1984.
Kengen, "Good results of tc-99m-mag3 clearance measurements with a dual headed gamma camera without plasma sampler," *J. Nuclear Med.*, 37:91P, Abstract No. 353, 1996.

Kikukawa et al., "Early and delayed Tc-99m ECD brain SPECT in SLE patients with CNS involvement," *Ann Nucl Med.* 14:25-32, 2000.
Kim et al., "Synthesis, biodistribution and imaging of mammary tumors using 99mtc-ec-polyglutamate; a glutamate receptor peptide," *J. Nuclear Medicine*, 41:231P Abstract 2000.
King et al., "Imaging of bone infection with labelled white bloo cells: role of contemporaneous bone marrow imaging," *European Journal of Nuclear Medicine*, 17:18-151, 1990.
Kitamura et al., "Chemical engineering of the monoclonal antibody A7 by polyethylene clycol for targeting cancer chemotherapy," *Cancer Research*, 51:4310-4315, 1991.
Klok et al., "Star-shaped fluorescent polypeptides," *Journal of Polymer Science*, 39(10):1572-1582, 2001.
Knight et al., "Radiolabeling of fibrinogen using the lodogen technique," *Throm. Res. Cen. Dept. Biochem.*, pp. 593-596, 1982.
Knight et al, "Thrombus imaging with technetium—99m synthetic peptides based upon the binding domain of a monoclonal antibody to activated platelets," *J. Nucl. Med.*, 35:282-288, 1991.
Koh et al., "Imaging of hypoxia in human tumors with [F-18]fluoromisonidazole,"*Int J Radiat Oncol Biol Phys*, 22:199-212, 1992.
Kopecek et al. "Targetable polymeric prodrugs," *J. Control. Release*, 6:315-327, 1987.
Kopecek and Kopeckova, "Targetable water-soluble polymeric antcancer drugs: achievements and unsolved problems," *Proc. Intern. Symp. Conol. Rel. Bioact. Mater.*, 20:190-191, 1993.
Kopecek, "The potential of water-soluble polymeric carriers in targeted and site-specific drug delivery," *Journal of Controlled Release*, 11:279-290, 1990.
Kranz et al., "Conjugates of folate and anti-T-cell-receptor antibodies specifically target folate-receptor-positive tumor cells for lysis," *Proc Natl Acad Sci*, 92:9057-9061, 1995.
Kung et al., "Synthesis of new bis(aminoethanethiol) (BAT) derivatives: possible ligands for 99mTc brain imaging agents," *J. Med. Chem.*, 28:1280-1284, 1985.
Lamberts et al., "Somatostatin receptor imaging in vivo localization of tumors with a radiolabeled somatostatin analog," *J. Steoid Biochem Mol Biol*, 37:1079-1082, 1990.
Lamki, "Radioimmunoscintigraphy of cancer: problems, pitfalls and prospects," *Nuclear Medicine Annual 1990*, New York, Raven Press Ltd., 113-150, 1990.
Larson et al., "Overview of clinical radioimmunodetection of human tumors," *Cancer*, 73(supp):832-835, 1994.
Leamon and Low, "Cytotoxicity of momordin-folate conjugates in cultured human cells," *J Biol Chem*, 267:24966-24971, 1992.
Leamon and Low, "Delivery of macromolecules into living cells: a method that exploits folate receptor endocytosis," *Proc Natl Acad Sci*, 88:5572-5576, 1991.
Leamon et al., "Cytotoxicity of folate-pseudomonas exotoxin conjugates toward tumor cells," *J Biol Chem*, 268:24847-24854, 1993.
LeClerc and Cedergren, "Modeling RNA-ligand interactions: the rev-binding element RNA-aminoglycoside complex," *J Med Chem*, 41:175-182, 1998.
Lee and Low, "Delivery of liposomes into cultured KB cells via folate receptor-mediated endocytosis," *J Biol Chem*, 269:3198-3204, 1994.
Li et al., "Antitumor activity of poly (L-glutamic acid)-paclitaxel on syngeneic and xenografter tumors," *Clinical Cancer Res.*, 5:891-897, 1999.
Li et al., "Complete regression of well-established tumors using a novel water-soluble poly(L-glutamic acid)-paclitaxel conjugate," *Cancer Res.*, 58:2404-2409, 1998.
Li et al., "Poly(L-glutamic acid)-anticancer drug conjugates," *Advanced Drug Delivery Rev.*, 54:695-713, 2002.
Li et al., "Synthesis and evaluation of water-soluble polyethylene glycol paclitaxel conjugate as a paclitaxel prodrug," *Anticancer Drugs*, 7(5):642-648, 1996.
Li et al., "Synthesis, metal chelate stability studies, and enzyme digestion of a peptide-linked DOTA derivative and its corresponding radiolabeled immunoconjugates," *Bioconjugate Chem.*, 4:275-283, 1993.
Liang et al., "The use of diaminodithiol for labeling small molecules with technetium-99m," *Nucl. Med. Biol.*, 14:63-67, 1987.

(56) References Cited

OTHER PUBLICATIONS

Lin et al., "The role of Tc-99m MDP and Ga-67 imaging in the clinical evaluation of malignant fibrous histiocytoma," *Clin. Nucl. Med.*, 19(11):996-1000, 1994.
Liu et al., "99mTc-labeled small peptides as diagnostic radiopharmaceuticals," *Chem. Rev.*, 99:2235-2268, 1999.
Liu et al., "Apoptotic signals delivered through the T-cell receptor of a T-cell hybrid require the immediate-early gene nur77," *Nature*, 367(6460):281-284, 1994.
Liu et al., "Bifunctional chelators for herapeutic lanthanide radiopharmaceuticals," *Bioconjugate Chemistry*, 12:7-34, 2001.
Liu et al., "Detection of anaerobic odontogenic infections by fluorine-18 fluoromisonidazole," *Eur. J. Nucl. Med.*, 23(10):1384-1387, 1996.
Liu et al., "Induction of apoptosis and activation of the capase cascade by anti-EGF receptor monoclonal antibodies in DiFI human colon cancer cells do not involve the C-jun N-terminal kinase activity," *British Journal of Cancer*, 82(12):1991-1999, 2000.
Lu et al., "Polymerizable fab' antibody fragments for targeting of anticancer drugs," *Nat. Biotech.*, 17:1101-1104, 1999.
Lu, "Antimitotic agents," In: Foye, WO. Ed., "Cancer chemotherapeutic agents," Washington, DC: American Chemical Society, 345-368, 1995.
Lundberg et al., "Conjugation of an anti-B-cell lymphoma monoclonal antibody LL2, to long-circulating drug-carrier lipid emulsions," *J Pharm Pharmacol*, 51:1099-1105, 1999.
Macapinlac et al., "Gallium-67-citrate imaging in nuclear oncology," Nucl. Med. Biol., 21(5):731-738, 1994.
Maeda et al., "Tumoritropic and lymphotropic principles of macromolecular drugs," *Crit. Rev. Ther. Drug Carrier Syst.*, 6(3):193-210, 1989.
Maeda, "SMANCS and polymer-conjugated macromolecular drugs: advantages in cancer chemotherapy," *Adv. Drug Delivery Rev.*, 6(2):181-202, 1991.
Makin and Hickman, "Apoptosis and cancer chemotherapy," *Cell Tissue Res.*, 301:143-152, 2000.
Mang'era and Verbruggen, "Synthesis and evaluation of beta-homocysteine derivatives of 99mtc-1,1-ec and 99mtc-1,1-ecd," *J. of Labelled Compounds and Radiopharmaceuticals*, 42:683-699, 1999.
Mann et al., "Molecular amplifiers: synthesis and functionalization of a poly(aminopropyl dextran bearing a uniquely reactive terminus for univalent attachment to biomolecules," *Bioconjugate Chemistry*, 3:154-159, 1992.
Marti and Risau, "Systematic hypoxia changes the organ-specific distribution of vascular endothelial growth factor and its receptors," *Proc. Natl. Acad. Sci., USA*, 95:15809-15814, 1998.
Martin et al., "Enhanced binding of the hypoxic cell marker [$^3$H]fluoromisonidazole in ischemic myocardium," *J Nucl Med*, 30:194-201, 1989.
Martin et al., "Noninvasive detection of hypoxic myocardium using fluorine-18 fluoromisonidazole and positron emission tomography," *J. Nucl. Med.*, 33(12):2202-2208, 1992.
Mason et al., "99mtc-desferoxamine: production, stability and solute clearance measurements after aerosolization," *J. Nuclear Med.*, 31:908, Abstract No. 865, 1990.
Masui et al., "Growth inhibition of human tumor cells in athymic mice by anti-epidermal growth factor receptor monoclonal antibodies," *Cancer Research*, 44:1002-1007, 1984.
Mather et al., "Tumour cell uptake of technetium dithiocarbamate complexes," *J. Nuclear Med.*, 38:186P, Abstract No. 797, 1997.
Mathew et al., "Synthesis and evaluation of some water-soluble prodrugs and derivatives of taxol with antitumor activity," *J. Med. Chem.*, 35:145-151, 1992.
McGahon et al., "Chemotherapeutic drug-induced apoptosis in human leukaemic cells is intependent of the Fas (APO-1/CD95) receptor/ligand system," *British Journal of Haematology*, 101:539-547, 1998.
Meares et al., "Macrocyclic chelates of radiometals for diagnosis and therapy," *British J. Cancer*, 62:21-26, 1990.

Mease et al., "Comparison of renal agents for detecting unilateral acute ischemic/reperfusion renal injury in rats," *J. Nuclear Med.*, 36:231P, Abstract No. 1033, 1995.
Mendelsohn et al., "Anti-epidermal growth factor recepotr monoclonal antibodies may inhibit A431 tumor cell proliferation by blocking autocrine pathway," *Trans. Assoc. Am. Phys.*, 100:173-178, 1987.
Mendelsohn, "Epidermal growth factor receptor inhibition by a monoclonal antibody as anticancer therapy," *Clinical Cancer Research*, 3:2703-2707, 1997.
Meredith et al., "Treatment of metastatic prostate carcinoma with radiolabeled antibody CC49," J. Nucl. Med., 35(6):1017-1022, 1994.
Meyer et al., "Tryptophan hydrolase antibodies used in the diagnosis of carcinoid," *Hepato-Gastroenterology*, 45:1522-1526, 1998.
Michalik et al., "Effect of various aminoglycoside antibiotics on glucose formation in isolated rabbit kidney-cortex tubules ," *Pharmacol. Res.*, 21:405-414, 1989.
Michiels et al., "Simultaneous estimation of effective renal plasma flow and glomerular filtration rate using tc-99m-ec.," *J. Nuclear Med.*, 37:91P, Abstract No. 355, 1996.
Milross et al., "Relationship of mitotic arrest and apoptosis to anti-tumor effect of paclitaxel," *J. National Cancer Institute*, 88(18):1308-1314, 1996.
Mitchell et al., "Active-specific immunotherapy for melanoma," *J. Clin. Oncol.*, 8(5):856-869, 1990.
Mochizuki et al., "Synthesis of poly-L-glutamates containing 5-substituted uracil moieties," *Nucleic Acids Symp. Ser.*, 16:121-124, 1985.
Modjahedi et al., "The receptor for EGF and its ligands: expression prognostic value and target for therapy in cancer (review)," *Int. J. Oncology*, 4(2):277-296, 1994.
Moller et al., "Biologic activities of naturally occurring human insulin receptor mutations," *J. Biol. Chem.*, 266:10995-11001, 1991.
Moran, "Technetium-$^{99m}$-EC and other potential new agents in renal nuclear medicine," *Seminars in Nucl. Med.*, 29: 91-101, 1999.
Morton et al., "Comparison of 2-point postural drainage with diuresis renography in the assessment hydronephrosis," *J. Nuclear Med.*, 37:46P, Abstract No. 174, 1996.
Morton et al., "Prolongation of survival in metastatic melanoma after active specific immunotherapy with a new polyvalent melanoma vaccine," *Ann. Surg.*, 216(4):463-482, 1992.
Mosmann, "Rapid colorimetic assay for cellular growth and survival: application to proliferation ans cytotoxicity assay,"*J. Immunol. Methods*, 65:55-63, 1983.
Mrhac et al., "Abnormal first-pass flow through the azygos vein from valsalva maneuver," *Clinical Nucl. Med.*, 21:331-332, 1996.
Murakami et al., "Calcium hydroxide ameliorates tobramycin toxicity in cultured chick tibiae," *Bone*, 21:411-418, 1997.
Murakami et al., "Interaction of tobramycin and pH in cultured chick tibiae," *J. Orthop. Res.*, 14:742-748, 1996.
Murray et al., "Matrix metalloproteinase-1 is associated with poor prognosis in oesophageal cancer," *Journal of Pathology*, 185:256-261, 1998.
Myszka et al., "Synthesis and induction of apoptosis in B cell chronic leukemia by diosgenyl 2-amino-2-deoxy-beta-D-glucopyranoside hydrochloride and its derivatives," *Carb. Res.*, 338:133-141, 2003.
Nakae and Nakae, "Diffusion of aminoglycoside antibiotics across the outer membrane of *Escherichia coli*," *Antimicrobial Agents and Chem.*, 22:554-559, 1982.
Namavari et al., "Synthesis of 8-[18F]Fluoroguanin derivatives: in vivo probes for imaging gene expression with positron emission tomography," *Nucl. Med. Biol.*, 27:157-162, 2000.
Nicolaou et al., "Design, synthesis, and biological activity of protaxols," *Nature*, 364:464-466, 1993.
Nordsmark et al., "Pretreatment oxygenation predicts radiation response in advanced squamous cell carcinoma of the head and neck," *Radiotherapy and Oncology*, 41:31-39, 1996.
Nosco et al., "Development of a kit formulation for 99mtcmag3 of very high purity and very high stability," *J. Nuclear Med.*, 31:908, Abstract No. 863, 1990.
Offield et al., "PDX-1 is required for pancreatic outgrowth and differentiation of the rostral duodenum," *Development*, 122:983-995, 1996.

(56) References Cited

OTHER PUBLICATIONS

Oldham et al., "Comparison of action of paclitaxel and poly (L-glutamic acid)-paclitaxel conjugate in human breast cacner cells," *Int. J. Oncol.*, 16(1):125-132, 2000.

Omelyanenko et al., "HPMA copolymer-anticancer drug-OV-TL16 antibody conjugates: influence of synthesis on the binding affinity to OVCAR-3 ovarian carcinoma cells in vitro," *J. Drug Targeting*, 3:357-373, 1996.

Omelyanenko et al., "HPMA copolymer-anticancer drug-OV-TL16 antibody conjugates II. Processing in epithelial ovarian carcinoma cells in vitro," *International Journal of Cancer*, 75(4):600-608, 1998.

Orr et al., "Similarity of folate receptor expression in UMSCC 38 cells to squamous cell carcinoma differentiation markers," *Natl. Cancer Inst.*, 87:299-303, 1995.

Ozanne et al., "Over-expression EGF receptor is a hallmark of squamous cell carcinomas," *J. Pathol.*, 149:9-14, 1986.

Ozker et al., "Technetium-$^{99m}$-N,N-ethylenedicysteine-a comparative study of renal scintigraphy with technetium-$^{99m}$-MAG3 and iodine-131-OIH in patients with obstructive renal disease," *J. Nucl. Med.*, 35:840-845, 1994.

Ozmen et al., "Effects of some antibiotics on activity of glucose-6-phosphate dehydrogenase from human erythrocytes in vitro and effect of isepamicin sulfate on activities of antioxidant enzymes in rat erythrocytes," *Drug Chem. Toxicol.*, 28:433-445, 2005.

Palyi et al., "Effects of methylacetylenic putrescine, and ornithine decarboxylase inhibitor and potential novel anticancer agent, on human and mouse cancer cell lines," *Anti-Cancer Drugs*, 10:103-111, 1999.

Pavicevic et al., "Serum tumor marker CYFRA 21-1 in the diagnostics of NSCLC lung cancer," *Coll Antropol*, 22(2):629-635, 1998.

Pavlik et al., "Properties of anticancer agents relevant to in vitro determinations of human tumor cell sensitivity," *Cancer Chemother Pharmacol*, 11:8-15, 1983.

Pedley et al., "The potential for enhanced tumour localisation by poly(ethylene glycol) modification of anti-CEA antibody," *British J. Cancer*, 70:1126-1130, 1994.

Petrak et al., "Transport of macromolecules across the capillary walls," *Adv. Drug Deliv. Review*, 3:191-214, 1989.

Phillips-Hughes et al., "Restenosis: pathophysiology and preventive strategies," *JVIR*, 7:321-333, 1996.

Philpott et al., "RadioimmunoPET: detection of colorectal carcinoma with positron-emitting copper-64-labeled monoclonal antibody," *J. Nucl. Med.*, 36:1818-1824, 1995.

Pietersz et al., "Specific in vitro anti-tumor activity of methotrexate-monoclonal antibody conjugates prepared using human serum albumin as an intermediary," *Immunol. Cell Biol.*, 66:43-49, 1988.

Pimm et al., "Differences in tumor and normal tissue concentrations of iodine and indium labeled monoclonal antibody II: biodistribution studies in mice with human tumor xenografts," *Dur. J. Nucl. Med.*, 11:300-304, 1985.

Pimm et al., "Strategies for labelling branched polypeptides with a poly (L-Lysine) backbone with radioiodines 123I, 125I, 131I) and radiometals (111In, 51Cr) for biodistribution studies wnad radiopharmaceutical development," *Journal of Labelled Compunds and Radiopharmaceuticals*, 36(2):157-172, 1995.

Piper et al.,"A synthetic approach to poly($\gamma$-glutamyl) conjugates of methotrexate," *J. Med. Chem.*, 26:291-294, 1983.

Pirmettis et al., "Synthesis and characterization of the tcd(ec) complex, a renal imaging agent," *J. Nuclear Med.*, 35:263P, Abstract No. 1079, 1994.

Popovici et al., "The influence of some antibiotics on hexokinase and pyruvate-kinase activity in the rat liver and kidney," *Arch. int. Pharmacodyn*, 193:80-86, 1971.

Potamianos et al., "Radioimmunoscintigraphy and radioimmunotherapy in cancer: principles and application," *Anticancer Research*, 20(2A):925-948, 2000.

Prvulovich et al., "Clinical evaluation of technetium-$^{99m}$-L,L-ethylenedicysteine in patients with chronic renal failure," *J. Nucl. Med.*, 38:809-814, 1997.

Putnam and Kopecek, "Polymer conjugates with anticancer activity," *Polymer Science*, 122:55-123, 1995.

Quadri et al., "Effects of linker chemistry on the pharmacokinetics of radioimmunoconjugates," *Quart. J. Nucl., Med.*, 42:250-261, 1998.

Raffauf et al., "Colchicine. Derivatives of trimethylcolchicinic acid," *J. Am Chem Soc*, 75:5292-5294, 1953.

Rasey et al., "Characterization of the binding of labeled fluoromisonidazole in cells in vitro," *Radiat Res*, 122:301-308, 1990.

Rasey et al., "Radiolabeled fluoromisonidazole as an imaging agent for tumor hypoxia," *Int. J. Radiat Oncol. Biol Phys*, 17:985-991, 1989.

Ratner and Clarke, "The action of formaldehyde upon cysteine," *J. Am Chem. Soc.*, 59:200-206, 1937.

Ravindranath et al., "Quantitation of the density of cell surface carbohydrate antigens on cancer cells with a sensitive cell-suspension ELISA," *J. Immunol. Methods*, 16(197):51-67, 1996.

Reed, "Apoptosis-targeted therapies for cancer," *Cancer Cell*, 3:17-22, 2003.

Reilly et al., "A comparison of EGF and Mab 528 labeled within for imaging human breast cancer," *J. Nucl. Med.*, 41:903-911, 2000.

Remington's Pharmaceutical Sciences, 19$^{th}$ Ed., Mach Printing Company, 1990, Smith and Rutlage, 1975.

Reutelingsperger and van Heerde, "Annexin V, the regulator of phosphatidylserine-catalyzed inflammation and coagulation during apoptosis," *Cell Mol Life Sci*, 53:527-532, 1997.

Rihova et al., "Antiproliferative effect of a lectin- and anti-thy-1.2 antibody-targeted HPMA copolymer-bound doxorubicin on primary and metastatic human colorectal carcinoma and on human colorectal carcinoma transfected with the mouse thy-1.2 gene," *Bioconjugate Chemistry*, 11(5):664-673, 2000.

Rihova, "Receptor-mediated targeted drug or toxin delivery," *Adv. Drug Deliv. Rev.*, 29:273-289, 1998.

Rogers et al., "Neomycin effects on glucose transport by rat small intestine," *Digestion*, 1:159-164, 1968.

Rosenberg et al., "Experience with the use of high-dose interleukin-2 in the treatment of 652 cancer patients," *Ann. Surg.*, 210(4):474-548, 1989.

Ross et al., "Differential regulation of folate receptor isoforms in normal and malignant tissue in vivo and in established cell lines," *Cancer*, 73:2432-2443, 1994.

Roth et al., "Gene therapy for cancer: what have the inventors done and where are the inventors going?" *J. Natl. Can. Inst.*, 89(1):21-39, 1997.

Rowinsky and Donehower, "Paclitaxel (taxol)," *New England Journal of Medicine*, 332:1004-1014, 1995.

Rowinsky et al., "Phase I and pharmacologic study of paclitaxel and cisplatin with granulocyte colony-stimulating factor: neuromuscular toxicity is dose-limiting,"*J. Clin. Oncol.*, 11(10):2010-2020, 1993.

Rowland et al., "Suppression of tumor growth in mice by drug-antibody conjugate using a novel approach to linkage," *Nature*, 255:487-488, 1975.

Sabbantini et al., "Early findings in a phase I study of PG-Paclitaxel (CT2103 in recurrent ovarian or primary peritoneal cancer," *Proc. AACR-NCI-EORTC Int. Conference on Molecule Targets and Cancer Therapeutics*, Abs, 470-96, 2001.

Sasaki et al., "Assessment of antioxidative ability in brain: imaging of glutathione localization with technetium-99m meso-hexamethyl propyleneamine," *J. Nuclear Med.*, 35:263P; Abstract No. 1083, 1994.

Sato et al., "Simple estimation of fractional renal uptake of tc-99m mag3 using graphical analysis without syringe counting and renal depth correction," *J. Nuclear Med.*, 37:292P, Abstract No. 1303, 1996.

Schechter et al., "Radiation dosimetry of 99mTc-labeled C225 in patients with squamous cell carcinoma of the head and neck," *J. Nucl. Med.*, 45:1683-1687.

Seabold et al., "Comparison of $^{99m}$Tc-Methoxyisobutyl Isonitrile and $^{201}$Tl Scintigraphy for Detection of Residual Thyroid Cancer After $^{131}$I Ablative Therapy," *J. Nucl. Med.*, 40(9):1434-1440 1999.

Semenza, "Regulation of mammalian O2 homeostasis by hypoxia-inducible factor 1," *Ann. Rev. Cell Dev. Biol.*, 15:551-578, 1999.

(56) References Cited

OTHER PUBLICATIONS

Serruys et al., "A comparison of balloon-expandable-stent implantation with balloon angioplasty in patients with cornonary artery disease," *New England J. Medicine*, 331(8):489-495 1994.
Seymour et al., "Synthetic polymers conjugated to monoclonal antibodies: vehicles for tumor-targeted drug delivery," *Select. Cancer Therapeut.*, 7(2):59-73, 1991.
Shankar et al., "Glucosamine infusion in rats mimics the beta-cell dysfunction of non-insulin-dependent diabetes mellitus," *Metabolism*, 47:573-577, 1998.
Shattuck et al., "Validation of the two sample technique for measuring gfr in renal transplant patients," *J. Nuclear Med.*, 36:231P, Abstract No. 1036, 1995.
Shih et al., "Anthracycline immunoconjugates prepared by a site-specific linkage via an amino-dextran intermediate carrier," *Cancer Res.*, 54:4192-4198 1991.
Shimada et al., "Biodistribution of liposomes containing synthetic galactose-terminated diacylglyceryl-poly(ethylen glycol)s," *Biochimica et Biophysica Acta*, 1326:329-341, 1997.
Shuke et al., "Modified renal counting method for estimation of tc-99m mag3 renal clearance," *J. Nuclear Med.*, 37:291P, Abstract No. 1301, 1996.
Silverman et al., "Evaluating tumor biology and oncological disease with positron-emission tomography," *Seminars in Radiation Oncology*, 8:183-196, 1998.
Skrzypczak-Jankun et al, "Structure of the hirugen and hirulog 1 complexes of α-thrombin," *J. Mol. Biol.*, 221:1379-1393, 1991.
Smalley et al., "Localization of fluorescent compounds in the firefly light organ," *J. Histochem. Cytochem.*, 28(4):323-329, 1980.
Smith et al., "Prognostic significance of vascular endothelial growth factor protein levels in oral and oropharyngeal squamous cell carcinoma," *J. Clin. Oncol.*, 18(10):2046-2052, 2000.
Stoffel et al., Evaluation of technetium-99m-L,1-ec in renal transplant recipients: a comparative study with technetium-$^{99m}$-MAG3 and iodine-125-0IH, *J. Nucl. Med.*, 35:1951-1958, 1994.
Subramanian et al., "Transchelation reactions in labeling ecd with tc-99m," *J. Nuclear Med.*, 31:908, Abstract No. 867, 1990.
Sudimack et al., "Targeted delivery via folate receptor," *Adv. Drug Deliv. Rev.*, 41:147-162, 2000.
Sun et al., "Idium(III) and Gallium(III) Complexes of Bis(aminoethanethiol) Ligands with Different Denticities: Stabilties, Molecular Modeling, and in Vivo Behavior," *Journal of Medicinal Chemistry*, 39(2):458, 1996.
Surwit et al., "Clinical assessmento f In-CYT-103 immunoscintigraphy in ovarian cancer," *Gynecol. Oncol.*, 48:285-292, 1993.
Suruki et al., "A modified graphic method for estimation of glomerular filtration index using dynamic renal images with tc-99m dtpa," *J. Nuclear Med.*, 36:231P, Abstract No. 1035, 1995.
Tachibana et al., "Inhibitory effects of kanamycin on glycolysis in cochlea and kidney-possible involvement in the formation of oto- and nephrotoxicities," *Biochem. Pharmacol.*, 25:2297-2301, 1976.
Taggart et al., "Novel mutations associated with carnitine palmitoyltransferase II deficiency," *Human Mutation*, 13(3):210-220, 1999.
Tait and Smith, "Site-specific mutagenesis of annexin V: role of residues from Arg-200 to Lys-207 in phospholipid binding," *Arch Biochem Biophys*, 288:141-144, 1991.
Takamizawa et al., "Differential apoptosis gene expression in pediatric tumors of the kidney," *J. Ped. Surg.*, 35(2):390-395, 2000.
Takashina et al., "Comparative pharmacokinetic properties of murine monoclonal antibody A7 modified with neocarzinostatin, dextran and polyethylene glycol," *Jpn. J. Cancer Res.*, 82:1145-1150, 1991.
Tam, "Synthetic peptide vaccine design: synthesis and properties of a high-density multiple antigenic peptide system," *Proc. Natl. Acad. Sci., USA*, 85:5409-5413, 1988.
Taylor et al., "Comparison of tc-99m0(n,n1-ethylenedicysteine isomers in rats and in normal volunteers," *J. Nuclear Med.*, 37:46P-47P, Abstract No. 177, 1996.

Taylor et al., "Comparison of technetium-$^{99m}$-LL-EC isomers in rats and humans," *J. Nucl. Med.*, 38:821-826, 1997.
Thompson, "Apoptosis in the pathogenesis and treatment of disease," *Science*, 267:1456-1462, 1995.
Tjuvajev et al., "Comparison of radiolabeled nucleoside probes (FIAU, FHGB and FHPG) for PET imaging of HSVI-tk gene expression," *J. Nucl. Med.*, 43:1072-1083, 2002.
Tod et al., "Clinical pharmacokinetics and pharmacodynamics of isepamicin," *Clin. Pharmacokinet.*, 38:205-223, 2000.
Tolomeo et al., "The CD95/CD95 ligand system is not the major effector in anticancer drug-mediated apoptosis," *Cell Death and Differentiation*, 5:735-742, 1998.
Tomalia et al., "Starburst dendrimers: molecular-level control of size, shape, surface chemistry, topology and flexibility from atoms to macroscopic matter," *Agnew. Chem. Int. Ed. Engl.*, 29:138-175, 1990.
Torchilin et al., "Chelating polymer modified monoclonal antibodies for radioimmunodiagnostics and radioimmunotherapy," *J. Controlled Release*, 24:111-118, 1993.
Tschopp et al., "Apoptosis: silencing the death receptors," *Curr. Biol.*, 9:R381-R384, 1999.
Tsukamoto et al., "The quantitation of absolute tc-99m-dmsa renal uptake in children from planar posterior-view method," *J. Nuclear Med.*, 37:291P, Abstract No. 1299, 1996.
Tubis and Endow, "The preparation of $^{99m}$technetium-labelled cystine, methionine and synthetic polypetide and their distribution in mice," *Int;. Journ. Appl. Rad. Isotop.*, 19:835-840, 1968.
Tuli et al., "Comparison of a simplified quantitation of tc-99m mag-3 renogram to core needle biopsy the diagnosis of renal transplant rejection," *J. Nuclear Med.*, 37:289P, Abstract No. 1290, 1996.
Ugur et al., "Renovascular hypertension due to takayasu's arteritis demonstrated by Tc-$^{99m}$ ethylenedicysteine captopril scintigraphy," *Clinical Nuclear Medicine*, 21:714-716, 1996.
Ugur et al., "Technetium-$^{99m}$-ethylenedicysteine in the diagnosis and follow-up of renovascular hypertension," *Investigative Radiology*, 31:378-381, 1996.
Ugur et al., "Technetium-$^{99m}$ ethylenedicysteine: an alternative agent to detect renovascular hypertension," *J. of Nuclear Med.*, 38:1662-1664, 1997.
Ugur et al., "The diagnosis of renovascular hypertension with tc-99m ethylenedicysteine captopril scintigraphy," *J. Nuclear Med.*,37:291P, Abstract No. 1302, 1996.
Ugur et al., "The diagnosis of renovascular hypertension with technetium-99m-ethylenedicysteine captopril scintigraphy," *Investigative Radiology*, 31:497-501, 1996.
Ugurel et al., "Increased serum concentration of angiogenic factors in malignant melanoma patients correlates with tumor progression and survival," *J. Clin. Oncol.*, 19(2):577-583, 2001.
Valk et al., "Hypoxia in human gliomas: Demonstration by PET with [$^{18}$F]fluoromisonidazole," *J Nucl Med*, 33:2133-2137, 1992.
Van den Eijnde et al., "In situ detection of apoptosis during embryogenesis with annexin V: from whole mount to ultrastructure," *Cytometry*, 29:313-320, 1997.
Van Heeswijk et al., "The synthesis and characterization of polypeptide-adriamycin conjugates and its complexes with adiramycin Part 1," *J. Controlled Release*, 1:301-315, 1985.
Van Nerom et al., "Comparison of renal excretion ocharacteristics of isomers l,l and d,d of tc-99m ethylenedicysteine," *J. Nuclear Med.*, 31:806, Abstract No. 412, 1990.
Van Nerom et al., "Optimalization of the labelling of ethylenedicysteine (ec) with technetium-99m," *J. Labelled Compounds and Radiopharmaceuticals*, XXX:37-39, 1991.
Van Schepdael et al., "Capillary electrophoretic analysis of ethylene dicysteine, a precursor of the radiopharmaceutical $^{99m}$Tc ethylene dicysteine," *J. Chromatography B*, 697:251-254, 1997.
Vega et al., "Targeting adriamycin to EGF receptors by site-specific conjugation of monoclonal antibody to poly(L-glutamic acid)," Division of Deagnostic Imaging and Departmetn of Experimental Therapeutics, U.T. M.D. Anderson Cancer Center, 1515 Holcombe Blvd., Houston, TX, USA.

(56) References Cited

OTHER PUBLICATIONS

Verbruggen et al., "Is syn or anti orientation of the oxotechnetium and carboxyl group in tc-99m renal function agents affecting the renal excretion rate?" *J. Labelled Compounds and Radiopharmaceuticals*, XXX:86-88, 1991.

Verbruggen et al., "Tc-99m 1,1-ethylenedicysteine, a potential alternative to tc-99m mag3," *J. Nuclear Med.*, 31:908, Abstract No. 864, 1990.

Villevalois-Cam et al., "Insulin-induced redistribution of the insulin-like growth factor II/mannose 6-phosphate receptor in intact rat liver," *J. Cell. Biochem.*, 77:310-322, 2000.

Vyas et al., "Phosphatase-activated prodrugs of paclitaxel," Taxane Anticancer Agents: Basic Science and Current Status, *American Chemical Society*, Washington, DC, 124-137, 1995.

Wahl et al., "Loss of normal p53 function conferes sensation to taxol by increasing g2/m arrest and apoptosis," *Nat. Med.*, 2(1):72-79, 1996.

Wahl, "Monoclonal antibodies in nucear medicine," *Nuclear Medicine Annual 1992*, New York, Raven Press Ltd., 91-103, 1992.

Walsh et al., "Noninvasive estimation of regional myocardial oxygen consumption by positron emission tomography with carbon-11 acetate in patients with myocardial infaction," *J. Nucl. Med.*, 30:1798-1808, 1989.

Wang et al., "Design and synthesis of [$^{111}$In]DTPA-folate for use as a tumor-targeted radiopharmaceutical," *Bioconjugate Chem*, 8:673-679, 1997.

Wang et al., "Synthesis, purification, and tumor cell uptake of Ga-67 deferoxamine-folate, a potential radiopharmaceutical for tumor imaging," *Bioconjugate Chem*, 7:56-62, 1996.

Wang et al., "Microtubule-interfering agents activate c-Jun N-terminal kinase/stress-activated protein kinase through both Ras and apoptosis signal-regulating kinase pathways," *J. Bio. Chem.*, 273:4928-4936, 1998.

Washburn et al., "Reliable kit preparation of tc99m pentavalent dimercaptosuccinic acid [tc-99m (v) dmsa]," *J. Nuclear Med.*, 35:263P, Abstract No. 1080, 1994.

Weir et al, "Prognostic value of single-photon emission tomography in acute ischaemic strike," *Eur. Journ. Nuc. Med.*, 24:21-26, 1989.

Weiss et al., "Hypersensitivity reaction from taxol," *J. Clin. Oncol.*, 8(7):1263-1268, 1990.

Weitman et al., "Cellular localization of the folate receptor: potential role in drug toxicity and folate homeostasis," *Cancer Res*, 52:6708-6711, 1992.

Weitman et al., "The folate receptor in central nervous system malignancies of childhood," *J Neuro-Oncology*, 21:107-112, 1994.

Weitman et al., "Distribution of the folate receptor GP38 in normal and malignant cell lines and tissues," *Cancer Research*, 52:3396-3401, 1992.

Wells et al., "Glycosylation of nucleocytoplasmic proteins: signal transduction and )-glcNAc," *Science*, 291:2376-2378, 2001.

Wen et al., "Conjugation with 111In-DTPA-poly(ethylene glycol) improves imaging of anti-EGF receptor antibody C225," *J. Nuclear Medicine*, 42(10):1530-1537, 2001.

Wen et al., "Improved radiolabeling of PEFylated protein: PEGylated annexin V for noninvasive imaging of tumor apoptosis," *Bioconjugate Chemistry*, 2002.

Wen et al., "Poly(ethylene glucol) conjugated anti-EGF receptor antibody C225 with radiometal chelator attached to the termini of polymer chains," *Bioconjugate Chem.*, 12:545-553, 2001.

Wester et al., "Synthesis and radiopharmacology of O-(2-[18F]fluoroethyl)-L-tyrosine for tumor imaging," *J. Nucl. Med.*, 40:205-212, 1999.

Westerhof et al., "Membrane transport of natural folates and antifolate compounds in murine L1210 leukemia cells: role of carrier- and receptor-mediated transport systems," *Cancer Res.*, 51:5507-5513, 1991.

Wright et al., "Aminoglycoside antibiotics: structures, functions, and resistance," In: *Resolving the Antibiotic Paradox*, Rosen and Mobashery eds, Kluwer Academic/Plenum Pub NY, 1998.

Wu et al., "Apoptosis induced by and anti-epidermal growth factor receptor monoclonal antibody in a human colorectal carcinoma cell line and its delay by insulin," *J. Clin. Invest.*, 95:1897-1905, 1995.

Yaghoubi et al., "Human pharacokinetic and dosimetry studies of {189F FHBG: a reporter probe for imaging herpes simplex virus type-1 thymidine kinase reporter gene expression," *J. Nucl. Med.*, 42:1225-1234, 2001.

Yamori et al., Potent antitumor activity of MS-247, a novel DNA minor groove binder, evaluated by an in vitro and in vivo human cancer cell line panel., *Cancer Res.*, 59:4042-4049, 1999.

Yanai et al., "Amplification of the entire kanamycin biosynthetic gene cluster during empirical strain improvement of *Streptomyces kanamyceticus*," *Proc. Natl. Acad. Sci. USA*, 103:9661-9666, 2006.

Yang and Kim, "Tracer development and hybrid imaging," *Eur. J. Nucl. Med. Mol. Imaging*, 32:1001-1002, 2005.

Yang et al., "Development of F-18-labeled fluoroerythronitroimidazole as a PET agent for imaging tumor hypoxia," *Radiology*, 194:795-800, 1995.

Yang et al., "(99m)Tc-EC-guanine: synthesis, biodistribution, and tumor imaging in animals," *Pharm. Res.*, 22:1471-1479, 2005.

Yang et al., "99mtc-ec-deoxyglucose: synthesis, cellular uptake, biodistribution an dscintigraphic imaging," *J. Labelled Cpd. Radiopharm.*, 44:S513-S514, Abstract, 2001.

Yang et al., "Assessment of cyclooxsense-2 expression with 99mTc-labeled celebrex," *Anticancer drugs*, 15:255-263, 2004.

Yang et al., "Imaging tumor folate receptors using 99mtc-ethylenedicysteine-folate," *Proceedings of the American Association for Cancer Research*, 40:259, Abstract #1720, 1999.

Yang et al., "Imaging tumor folate receptors using radiolabeled folate and methotrexate," *J. Labelled Cpd. Radiopharm.*, 42:S696-S697, 1999.

Yang et al., "Metabolic pathways that mediate inhibition of hypothalamic neurons by glucose," *Diabetes*, 53:67-73, 2004.

Yang et al., "Molecular imaging using 99m-tc-ec-nitroimidazole, and 99mtc-ec-annexin v in tumor-bearing rodents," *Proceedings of the American Association for Cancer Research Annual Meeting*, 41:766, Abstract, 2000.

Yasui et al., "Expression of epidermal growth factor receptor in human gastric and colonic carcinomas," *Cancer Res.*, 48:137-141, 1995.

Ye et al., TRAF family proteins interact with the common neurotrophin receptor and modulate apoptosis induction, *J. Biol. Chem.*, 274(42):30202-30208, 1999.

Yeh et al., "Fluorine-18 fluoromisonidazole tumour to muscle retention ratio for the detection of hypoxia in nasopharyngeal carcinoma," *Eur. J. Nucl. Med.*, 23(10):1378-1383, 1996.

Yen et al., "A comparative study of evaluating renal scars by 99mTc-DSMA planar and SPECT renal scans, intravenous urography, and ultrasonography," *Ann. Nucl. Med.*, 8(2):147-152, 1994.

Yen et al., "Technetium-99m-DMSA renal SPECT in diagnosing and monitoring pediatric acute pyelonephritis," *J. Nucl. Med.*, 37(8):1349-1353, 1996.

Yen et al., "The role of technetium-99m sestamibi whole-body scans in diagnosing metastatic Hurthle cell carcinoma of the thyroid gland after total thyroidectomy: a comparison with iodine-131 and thallium-201 whole-body scans," Eur. J. Nucl. Med., 21(9):980-983, 1994.

Yokoyama et al., "Polymer micelles as novel drug carrier: adriamycin-conjugated poly(ethylen glycol)-poly(aspartic acid) block copolymer," *J. Controlled Release*, 11:269-278, 1990.

Yokoyama et al., "Preparation of micelle-formin polymer-drug conjugates," *Bioconjugate Chem.*, 3:295-301, 1992.

Yoshinari et al., "Mode of action of a new indolocarbazole anticancer agent, J-107088, targeting topoisomerase I," *Cancer Res.*, 59:4271-4275, 1999.

Yoshino et al., "Differential effects of troglitazone and D-chiroinositol on glucosamine-induced insulin resistance in vivo in rats," *Metabolism.* 48:1418-23, 1999.

Young et al., "Influence of immunoglobulin heavy and light-chain expression on B-cell differentiation," *Genes Develop.*, 8:1043-1057, 1994.

Zakko et al., "Biliary excretion of Tc-$^{99m}$ ec in renal studies," *Clinical Nuclear Medicine*, 23:417-419, 1998.

(56) References Cited

OTHER PUBLICATIONS

Office Action issued in Japanese Application 2004-552132 (related to U.S. Appl. No. 11/770,395) dated Mar. 17, 2009 (English Translation).
Office Action, issued in U.S. Appl. No. 11/627,299, mail date May 29, 2008.
Office Action, issued in U.S. Appl. No. 11/627,299, mail date Feb. 25, 2009.
Office Action, issued in U.S. Appl. No. 11/760,456, mail date Jul. 8, 2008.
Office Action, issued in U.S. Appl. No. 11/760,456, mail date Nov. 1, 2008.
Office Action, issued in U.S. Appl. No. 11/405,334, mail date Mar. 27, 2008.
Office Action, issued in U.S. Appl. No. 11/405,334, mail date Dec. 11, 2008.
Office Action, issued in U.S. Appl. No. 11/405,334, mail date Mar. 18, 2009.
Office Action, issued in U.S. Appl. No. 10/732,919, mail date Jan. 4, 2007.
Office Action, issued in U.S. Appl. No. 10/732,919, mail date Nov. 5 2007.
Office Action, issued in U.S. Appl. No. 10/732,919, mail date Oct. 2, 2008.
Office Action, issued in U.S. Appl. No. 10/732,919, mail date Apr. 8, 2009.
Office Action, issued in U.S. Appl. No. 10/732,919, mail date Dec. 4, 2009.
Qu et al., "Technetium-99m labeling on monoclonal antibodies via N,N'-ethylen-bis-L-cysteine," *Radiochimica Acta*, 63:209-212, 1993.
Sumita, "Evaluation of left ventricular function using 99mTc-diethylenetriamine-pentaacetic acid-human serum albumin (DTPA-HSA)," *Radioisotopes*, 37:502-8, 1988, Abstract.
Yang et al., "Molecular targets for cancer imaging and therapy applications," *Ann. Nucl. Med. Sci.*, 13:19-36, 2000.
Extended European Search Report issued in Application No. 06769952, dated Nov. 12, 2010.
Li et al., "A Calcium-Sensitive Magnetic Resonance Imaging Contrast Agent," *Journal of the American Chemical Society*, 121(6): 1413-1414, 1999.
Office Action issued in Korean Application No. 10-2008-7028323, and English language translation thereof, mailed Feb. 15, 2013.
Result of Consultation issued in European Application No. 06 769 952.0, mailed Mar. 1, 2013.
Yang et al., "Targeting EGFR-TK with radiolabeled cyclam-tyrosine," *Proc Amer Assoc Cancer Res*, Abstract #2394, 47:566, 2006.
Office Action issued in Canadian Application No. 2,649,869, mailed Dec. 18, 2013.

* cited by examiner 10, 60, and 120 Min $^{99m}$Tc-N4-DG (cyclam) Imaging in rats with and without tumor 60, and 120 Min comparison of $^{99m}$Tc-N4-DG (cyclam) & $^{99m}$Tc-EC-DG image of breast tumor cell line bearing rats.

Comparison of $^{99m}$Tc-N4 & $^{99m}$Tc-N4-AMT (cyclam)
Imaging in Rabbit Immediate, 1 HR, and 3 HR after injection

$^{68}$Ga Micro-PET Imaging
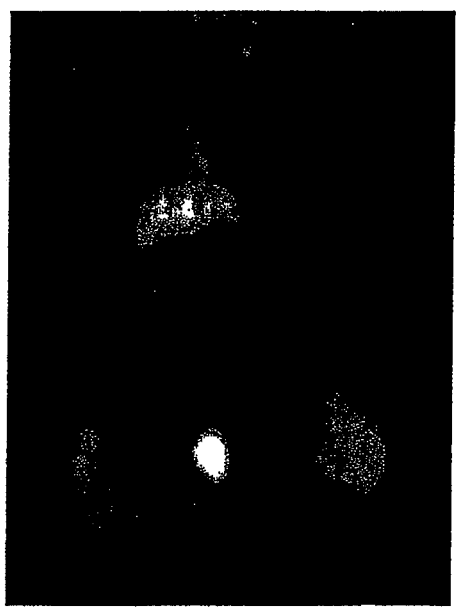 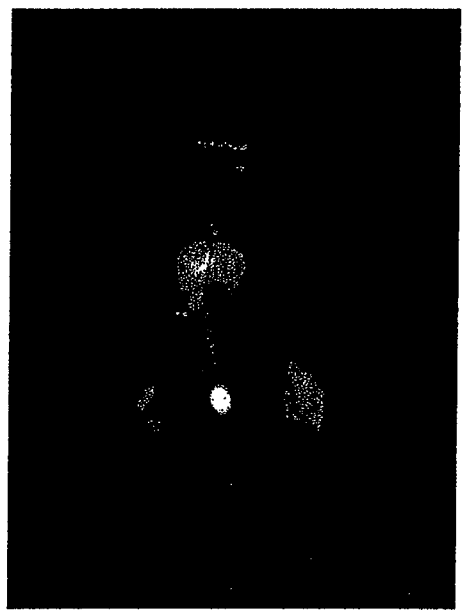
$^{68}$Ga-N4-AMT         $^{68}$Ga-N4-AMT
FIG. 10

Triprotection of Cyclam

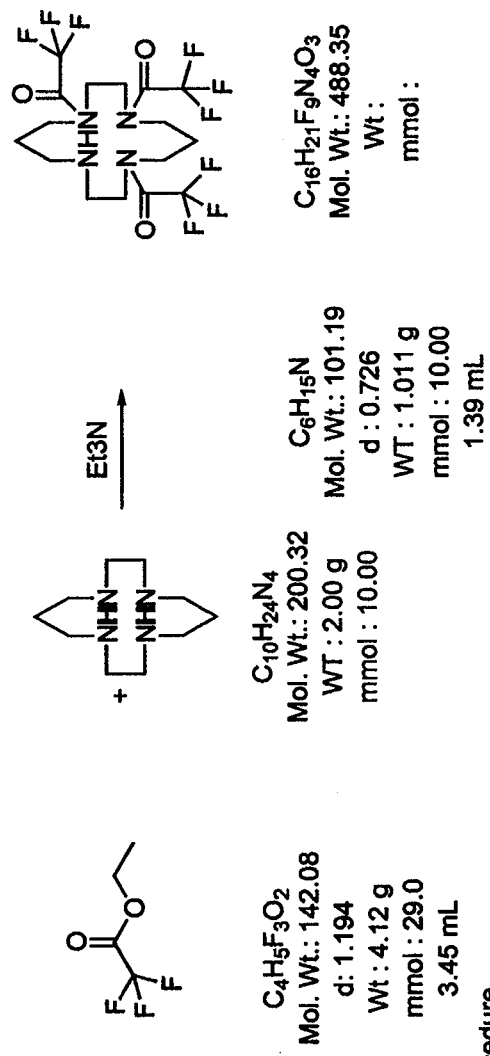

Porcedure
1) 2.0 g of N4 is added to 15 mL of methanol (anhydrous) under nitrogen atmosphere with stirring at room temperature
2) 1.39 mL of triethylamine was added to a reaction mixture
3) 3.45 mL of Ethyl trifluoroacetate was added dropwise to upper solution over a period of 5 minutes while stirring.
4) The addition continued over a period of 5 minutes.
5) The homogeneous reaction mixture was cooled with an ice-water bath to control the mild exothermic
6) Stirring was continued under $N_2$ for 5 Hours.
7) Volatiles were removed in vacuo.
8) The crude product was purified by coulmn chromatography using ethylacetate:hexane (8:2)

FIG. 18 de-*t*-butoxycarboxylation

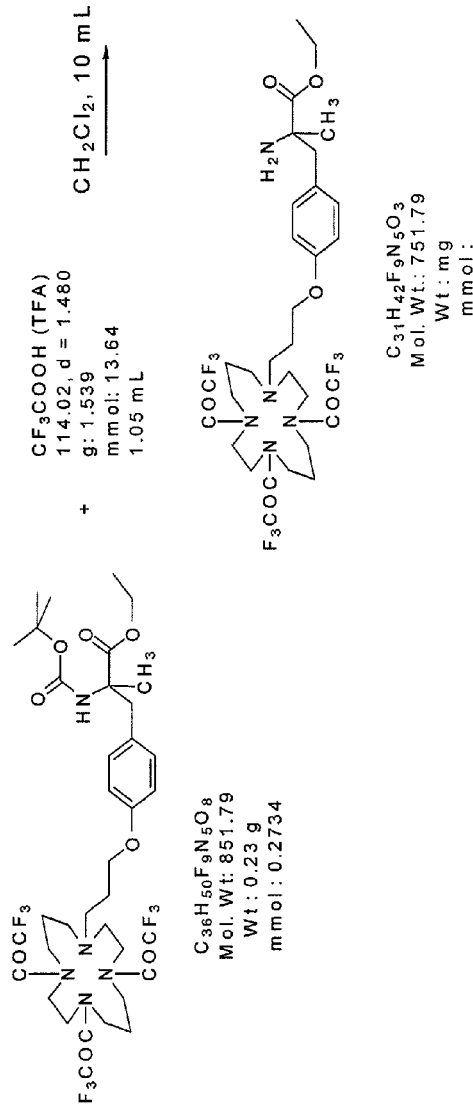

Porcedure: Exposure of AMTCylam to trifloroacetetic acid caused quantitative de-*t*-butoxycarboxylation.

1) 0.23 g (mmol: 0.2734) of AMTCyclam was added to 10.0 mL of $CH_2Cl_2$ add 1.00 mL of TFA was added at 0 °C to the solution and stirred for 4 h.
2) Check the TLC in $CHCl_3$:$CH_3OH$ (9:1). If the reaction is not complete add 1.00 mL of TFA and continue stirring for another 4 h.
3) Excess of TFA and volatiles were removed in vacuo.
4) Solubility of the product was checked. It was soluble in water and chloroform.
5) The compound was dissolved in 30 mLCHCl$_3$, dried in $MgSO_4$ (anhydrous), filtered, and evaporated to dryness in vacuo.
6) Pale yellow liquid was obtained.
7) Check the TLC $CH_3Cl_3$:$CH_3OH$ (9:1).
8) $^1$H NMR showed the collapse of *t*-boc peak at 1.5 ppm.

FIG. 21

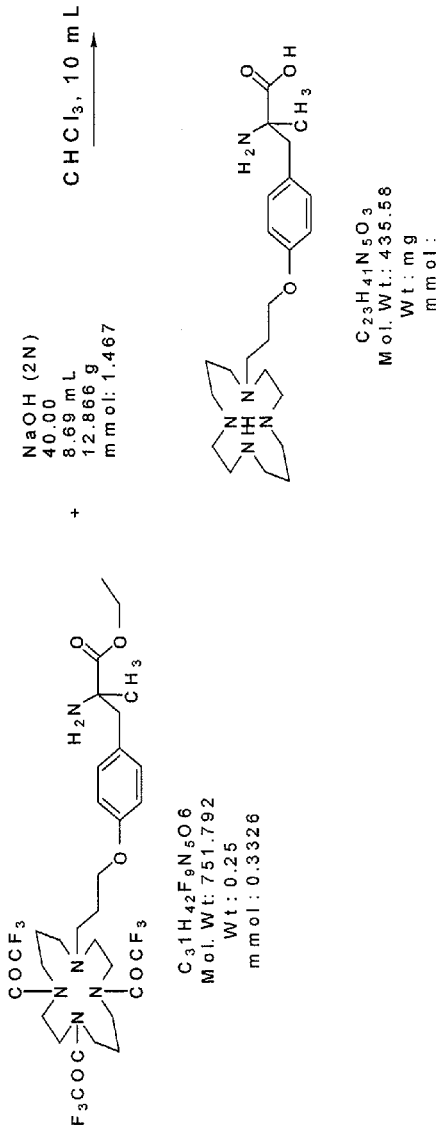

Porcedure:
1) 0.25 g (mmol: 0.3326) of de-boc-AMTCyclam was slurried in 5.0 mL of 2M NaOH and warmed in 10 mL of CHCl₃ at 60 °C over night.
2) The compound was extrated from aquous layer with CH₃OH:CHCl₃ mixture (1:3), three times and the organic layers was combined.
3) Organic layer was dried in MgSO₄ anhydrous, filtered and dried in vacuo.
4) In a seperate vessel in 10 g of MgSO₄ anhydrous 50 mL of ether was added, and 5 mL HCl was added to this mixture.
5) The compound was dissolve in ether (5 mL), and to this HCl/ether solution was added drop by drop untill a whit ppt is formed.
6) The solved was evaporated, and dried in vauo. white solid was obtained.
7) The crude compound was dissolved in 5 mL of water and washed several times with CHCl₃.
8) Then the compound was lyophilized. TLC CHCl₃:CH₃OH (9:1).

FIG. 22

Effect of N4-Glucosamine on cell cycle uptake in breast cancer cells (13762, 2hr incubation)

13762 cells (20 M) were incubated with Hoechst dye for 1 hour at 37oC. A cell sorter was used to sort cell cycles. 50,000 cells were plated in each well and incubated with 4uCi of tracers. High S-phase uptake was noted in N4-G.

$^{68}$Ga-N4-TML PET Imaging 30 minutes PET coronal imaging (dorsal to ventral order) of Ga-N4-TML;
07/20/2006
45 minutes after injection of 0.66 mCi of the compound

COMPOSITIONS AND METHODS FOR CELLULAR IMAGING AND THERAPY

This application claims the benefit of the filing date of U.S. Provisional Patent Application Ser. No. 60/745,148, filed Apr. 19, 2006, the entire contents of which are hereby incorporated by reference.

BACKGROUND OF THE INVENTION

1. Field of the Invention

The present invention relates generally to the fields of chemistry and radionuclide imaging. More particularly, it concerns compositions and methods involving $N_4$ compounds.

2. Description of Related Art

Radionuclide imaging modalities (e.g., Positron Emission Tomography, PET; Single Photon Emission Computed Tomography, SPECT) map the location and concentration of radionuclide-labeled compounds. To improve the diagnosis, prognosis, planning and monitoring of tissue specific disease treatment, characterization of disease tissue is extensively determined by development of more disease specific pharmaceuticals. PET $^{18}$F-fluorodeoxyglucose (FDG) has been used to diagnose and evaluate tumors, myocardial infarctions and neurological diseases. Although tumor metabolic imaging using $^{18}$F-FDG has been studied in the last two decades, its clinical practice is still limited by the factors such as easy access, availability and isotope cost. In addition, $^{18}$F chemistry is complex and requires longer synthesis times (e.g., $^{18}$F-FDG, 40-75 min), and it is difficult to produce multiple agents simultaneously. Thus, it would be desirable to develop a simple chelation technique for labeling agents using metallic isotopes for tissue specific targeted radioimaging and radiotherapy.

Improvement of scintigraphic tumor imaging will benefit from the development of more tumor specific radiopharmaceuticals. Due to greater tumor specificity, radiolabeled ligands as well as radiolabeled antibodies have opened a new era in scintigraphic detection of tumors and have undergone extensive preclinical development and evaluation (Mathias et al., 1996, 1997a, 1997b). Radionuclide imaging modalities (e.g., PET, SPECT) are diagnostic cross-sectional imaging techniques that map the location and concentration of radionuclide-labeled radiotracers. Although CT and MRI provide considerable anatomic information about the location and the extent of tumors, these imaging modalities typically cannot adequately differentiate invasive lesions from edema, radiation necrosis, grading, or gliosis. PET and SPECT can be used to localize and characterize tumors by measuring metabolic activity. Thus, methods that allow for more specific imaging of tumors is desirable.

One approach for producing novel compounds for imaging has involved the use of ethylenedicysteine (EC) derivatives, which are distinct from the compositions of the present invention. Several compounds have been labeled with $^{99m}$Tc using nitrogen and sulfur chelates (Blondeau et al., 1967; Davison et al., 1980). Bis-aminoethanethiol tetradentate ligands, also called diaminodithiol compounds, are known to form very stable Tc(V)O complexes on the basis of efficient binding of the oxotechnetium group to two thiol sulfur and two amine nitrogen atoms. Radiometal complexes of 2-pyrrolthiones labeled with $^{99m}$Tc have been developed for use as radiopharmaceuticals for imaging and therapy (WO 0180906A2). $^{99m}$Tc-L,L-ethylenedicysteine ($^{99m}$Tc-EC) is a recent and successful example of $N_2S_2$ chelates. EC can be labeled with $^{99m}$Tc easily and efficiently with high radiochemical purity and stability, and is excreted through the kidney by active tubular transport (Surma et al., 1994; Van Nerom et al., 1990, 1993; Verbruggen et al., 1990, 1992). Furthermore, $^{99m}$Tc chelated with ethylenedicysteine (EC) and conjugated with a variety of ligands has been developed for use as an imaging agent for tissue-specific diseases, as a prognostic tool, and as a tool to deliver therapeutics to specific sites within a mammalian body (WO 0191807A2, AU 0175210A5). $^{99m}$Tc-EC-chelates have been developed for renal imaging and examination of renal function (U.S. Pat. Nos. 5,986,074 and 5,955,053). A method of preparing $^{99m}$Tc-EC complexes and a kit for performing said method have also been developed (U.S. Pat. No. 5,268,163 and WO 9116076A1). U.S. Pat. No. 6,692,724 discloses ethylenedicysteine drug conjugates and is incorporated by reference herein in its entirety.

SUMMARY OF THE INVENTION

The present invention is based on the identification of certain novel $N_4$ compounds, and the finding that these compounds can be applied in the imaging of a site in a subject, and in the diagnosis and treatment of disease in a subject.

In certain embodiments, the present invention generally pertains to a compound of formula (I):

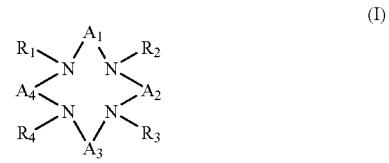

wherein $A_1$, $A_2$, $A_3$, and $A_4$ are each independently alkyl or substituted alkyl; and $R_1$, $R_2$, $R_3$, $R_4$ are each independently H, alkyl, substituted alkyl, -alkyl-COOH, a protecting group, a functional group, a targeting ligand, a linker, or any combination of one or more of these groups.

In some embodiments regarding the compound of formula (I), none of $R_1$, $R_2$, $R_3$, or $R_4$ are H. In some embodiments, $R_1$, $R_2$, $R_3$, and $R_4$ are not all H. In some embodiments, $R_1$, $R_2$, $R_3$, and $R_4$ are not all alkyl. In some embodiments, $R_1$, $R_2$, $R_3$, and $R_4$ are not all the same alkyl radical (e.g., $R_1$, $R_2$, $R_3$, or $R_4$ are not all methyl, ethyl, etc.). In some embodiments, $R_1$, $R_2$, $R_3$, and $R_4$ are not all $CH_2COOH$. In certain embodiments, at least one of $R_1$, $R_2$, $R_3$, or $R_4$ is a targeting ligand. In certain embodiments, only one of $R_1$, $R_2$, $R_3$, or $R_4$ is a targeting ligand. In certain embodiments, only two of $R_1$, $R_2$, $R_3$, or $R_4$ are targeting ligands. In certain embodiments, only three of $R_1$, $R_2$, $R_3$, or $R_4$ are targeting ligands. In certain embodiments, each of $R_1$, $R_2$, $R_3$, and $R_4$ is a targeting ligand. If the compound includes more than one targeting ligand, the targeting ligands may be identical or distinct types of targeting ligands. Examples of types of targeting ligands are discussed in greater detail in the specification below.

In certain embodiments, the compound of formula (I) comprises a linker, as described herein. In certain embodiments, $R_1$, $R_2$, $R_3$, and/or $R_4$ is a linker-targeting ligand. That is, $R_1$, $R_2$, $R_3$, and/or $R_4$ is a substituent having a linker group that links a targeting ligand to an annular nitrogen of the compound of formula (I). In some embodiments, the linker is selected from the group consisting of a peptide, glutamic acid, aspartic acid, bromo ethylacetate, ethylene diamine, lysine and any combination of one or more of these groups.

In particular embodiments, at least one of $R_1$, $R_2$, $R_3$, and $R_4$ is a targeting ligand. In still further embodiments, $A_1$, $A_2$, $A_3$, and $A_4$ are each independently —$(CH_2)_x$—, wherein x=2-4; and $R_1$, $R_2$, $R_3$, $R_4$ are each independently H, alkyl, substituted alkyl, -alkyl-COOH, a protecting group, a targeting ligand, or a linker-targeting ligand, wherein if $A_1$=—$(CH_2)_2$— and $A_3$=—$(CH_2)_2$—, and either $A_2$ and $A_4$=—$(CH_2)_2$—, or $A_2$ and $A_4$=—$(CH_2)_3$—, then at least one of $R_1$, $R_2$, $R_3$, and $R_4$ is a targeting ligand.

In certain embodiments of the compound of formula (I), if $A_1$=—$(CH_2)_2$— and $A_3$=—$(CH_2)_2$—, and either $A_2$ and $A_4$=—$(CH_2)_2$—, or $A_2$ and $A_4$=—$(CH_2)_3$—, then at least one of $R_1$, $R_2$, $R_3$, and $R_4$ is a targeting ligand that is a cardiovascular drug, an antimicrobial, an antifungal, a DNA topoisomerase inhibitor, a DNA intercalator, an antimetabolite, a disease cell cycle targeting compound, an epidermal growth factor receptor ligand, an angiogenesis targeting ligand, a tumor marker, a folate receptor targeting ligand, an apoptotic cell targeting ligand, a hypoxia targeting ligand, an androgen, luteinizing hormone, luteinizing hormone releasing hormone (LHRH), transferrin, a progestin, tetraacetate mannose, α-β-tyrosine, tyrosine, a tyrosine derivative, estrone, tamoxifen, or α-methyltyrosine, a receptor marker, a peptide, a nucleotide, diatrizoate, a gadolinium chelate, sodium fluorescein, an antisense molecule, a siRNA, glutamate pentepeptide, an agent that mimics glucose, amifostine, angiostatin, monoclonal antibody C225, monoclonal antibody CD31, monoclonal antibody CD40, capecitabine, deoxycytidine, fullerene, herceptin, human serum albumin, lactose, quinazoline, thalidomide, transferrin, trimethyl lysine, tamoxifen, topotecan, LHRH, podophyllotoxin, colchicine, endostatin, tomudex, thiotepa, cyclophosphamide, busulfan, improsulfan, piposulfan, benzodopa, carboquone, meturedopa, uredopa, altretamine, triethylenemelamine, triethylenephosphoramide, triethylenethiophosphoramide, trimethylolomelamine, bullatacin, bullatacinone, bryostatin, callystatin, CC-1065, adozelesin, carzelesin, bizelesin, cryptophycin 1, cryptophycin 8, dolastatin, duocarmycin, KW-2189, CB1-TM1, eleutherobin, pancratistatin, a sarcodictyin, spongistatin, chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, and ranimnustine, calicheamicin, dynemicin, clodronate, an esperamicin, neocarzinostatin chromophore, an aclacinomysin, actinomycin, authramycin, azaserine, a bleomycin, cactinomycin, carabicin, caminomycin, carzinophilin, a chromomycin, dactinomycin, daunorubicin, detorubicin, 6-diazo-5-oxo-L-norleucine, epirubicin, esorubicin, idarubicin, marcellomycin, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, 5-fluorouracil (5-FU), denopterin, methotrexate, pteropterin, trimetrexate, 6-mercaptopurine, thiamiprine, thioguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, folinic acid, aceglatone, aldophosphamide glycoside, aminolevulinic acid, eniluracil, amsacrine, bestrabucil, bisantrene, edatraxate, defofamine, demecolcine, diaziquone, elformithine, elliptinium acetate, an epothilone, etoglucid, gallium nitrate, hydroxyurea, lentinan, lonidainine, a maytansinoid, mitoguazone, mopidanmol, nitraerine, pentostatin; phenamet; pirarubicin; losoxantrone; podophyllinic acid; 2-ethylhydrazide; procarbazine, PSK-polysaccharide complex, razoxane, rhizoxin, sizofuran, spirogermanium, tenuazonic acid, triaziquone, 2,2',2"-trichlorotriethylamine, a trichothecene, urethan, vindesine, dacarbazine, mannomustine, mitobronitol, mitolactol, pipobroman, gacytosine, arabinoside ("Ara-C"), cyclophosphamide, thiotepa, doxetaxel, chlorambucil, 6-thioguanine, mercaptopurine, methotrexate, cisplatin, oxaliplatin, carboplatin, vinblastine, platinum, ifosfamide, mitoxantrone, vincristine, vinorelbine, novantrone, teniposide, edatrexate, daunomycin, aminopterin, xeloda, ibandronate, irinotecan, RFS 2000, difluoromethylomithine (DMFO), retinoic acid, a topoisomerase I (ST1968) inhibitor, a MEK inhibitor, an akt inhibitor, a VEGF receptor tyrosine kinase inhibitor, or capecitabine.

A "targeting ligand" is defined herein to be a molecule or part of a molecule that binds with specificity to another molecule. One of ordinary skill in the art would be familiar with the numerous agents that can be employed as targeting ligands in the context of the present invention. The targeting ligand can be any such molecule known to those of ordinary skill in the art. Non-limiting examples of targeting ligands include a tissue-specific ligand, an antimicrobial, an antifungal, or an imaging agent.

In some embodiments, the targeting ligand is a "tissue-specific ligand." A "tissue-specific ligand" is defined herein to refer to a molecule or a part of a molecule that can bind or attach to one or more tissues. The binding may be by any mechanism of binding known to those of ordinary skill in the art.

Non-limiting examples of tissue-specific ligands include a drug, a DNA topoisomerase inhibitor, a DNA intercalator, an antimetabolite, a disease cell cycle targeting compound, a gene expression marker, an angiogenesis targeting ligand, a tumor marker, a folate receptor targeting ligand, an apoptotic cell targeting ligand, a hypoxia targeting ligand, a disease receptor targeting ligand, a receptor marker, a peptide, a nucleotide, an antibody, an antisense molecule, a siRNA, glutamate pentepeptide, an agent that mimics glucose, amifostine, angiostatin, monoclonal antibody C225, monoclonal antibody CD31, monoclonal antibody CD40, capecitabine, deoxycytidine, fullerene, herceptin, human serum albumin, lactose, quinazoline, thalidomide, transferrin, and trimethyl lysine.

In some embodiments, the tissue-specific ligand may be a drug, such as an anticancer agent. Non-limiting examples of anti-cancer agents include tamoxifen, topotecan, LHRH, podophyllotoxin, colchicine, endostatin, tomudex, thiotepa, cyclophosphamide, busulfan, improsulfan, piposulfan, benzodopa, carboquone, meturedopa, uredopa, altretamine, triethylenemelamine, trietylenephosphoramide, triethiylenethiophosphoramide, trimethylolomelamine, bullatacin, bullatacinone, bryostatin, callystatin, CC-1065, adozelesin, carzelesin, bizelesin, cryptophycin 1, cryptophycin 8, dolastatin, duocarmycin, KW-2189, CB1-TM1, eleutherobin, pancratistatin, a sarcodictyin, spongistatin, chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, and ranimnustine, calicheamicin, dynemicin, clodronate, an esperamicin, neocarzinostatin chromophore, an aclacinomysin, actinomycin, authramycin, azaserine, a bleomycin, cactinomycin, carabicin, caminomycin, carzinophilin, a chromomycini, dactinomycin, daunorubicin, detorubicin, 6-diazo-5-oxo-L-norleucine, epirubicin, esorubicin, idarubicin, marcellomycin, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, 5-fluorouracil (5-FU), denopterin, methotrexate, pteropterin, trimetrexate, 6-mercaptopurine, thiamiprine, thioguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, folinic acid, aceglatone, aldophosphamide glycoside, aminolevulinic acid, eniluracil, amsacrine, bestrabucil, bisantrene, edatraxate, defofamine, demecolcine, diaziquone, elformithine, elliptinium acetate, an epothilone, etoglucid, gallium nitrate, hydroxyurea, lentinan, lonidainine, a maytansinoid, mitoguazone, mopidanmol, nitraerine, pentostatin; phenamet; pirarubicin; losoxantrone; podophyllinic acid; 2-ethylhydrazide; procarbazine, PSK polysaccharide complex, razoxane, rhizoxin, sizofuran, spirogermanium, tenuazonic acid, triaziquone, 2,2',2"-trichlorotriethylamine, a trichothecene, urethan, vindesine, dacarbazine, mannomustine, mitobronitol, mitolactol, pipobroman, gacytosine, arabinoside ("Ara-C"), cyclophosphamide, thiotepa, doxetaxel, chlorambucil, 6-thioguanine, mercaptopurine, methotrexate, cisplatin, oxaliplatin, carboplatin, vinblastine, platinum, ifosfamide, mitoxantrone, vincristine, vinorelbine, novantrone, teniposide, edatrexate, daunomycin, aminopterin, xeloda, ibandronate, irinotecan, RFS 2000, difluoromethylomithine (DMFO), retinoic acid, and capecitabine.

Other examples of drugs include cardiovascular drugs. Non-limiting examples of such drugs include an antihyperlipoproteinemic agent, an antiarteriosclerotic agent, an antithrombotic agent, a fibrinolytic agent, an antiplatelet agent, a blood coagulant, a thrombolytic agent, an antiarrythmic agent, an antihypertensive agent, a vasopressor, an anti-angiotension II agent, an afterload-preload reduction agent, a diuretic, and an inotropic agent. Examples of cardiovascular drugs are discussed in greater detail below. Some examples include mexiletine, tocamide, moricizine, procainamide, disopyramide, quinidine, popafenone, flecamide, encamide, bepridil, verapamil, diltiazem, bretylium, sotalol, amiodarone, ibutilide, propranolol and atropine.

In some embodiments, the targeting ligand is a DNA topoisomerase inhibitor. Non-limiting examples include a fluoroquinolone antibiotic, irinotecan, topotecan, etoposide, teniposide, lurtotecan, exatecan and rubitecan. Non-limiting examples of DNA intercalators include 7-aminoactinomycin, etihidium, proflavin, daunomycin, doxorubicin, and thalidomide.

In some embodiments, the targeting ligand is an antimetabolite. Non-limiting examples include azathioprine, a mercaptopurine, a pyrimidine, a sulfanilamide drug, methotrexate, tetrahydrofolate, folic acid, pemetrexed, raltitrexed, thioguanine, fludarabine, pentostatin, cladribine, fluorouracil, floxuridine, and gemcitabine.

The targeting ligand may be a disease cell cycle targeting ligand. Non-limiting examples include adenosine, FIAU, FIRU, IVFRU, GCV, PCV, FGCV, FPCV, FHPG, FHBG, and guanine.

In some embodiments, the targeting ligand is a gene expression marker. For example, the gene expression marker may be an epidermal growth factor receptor ligand (e.g., 68Ga—N4-Tyrosine). In further embodiments, the targeting ligand is an angiogenesis targeting ligand. Non-limiting examples include a COX-2 inhibitor, anti-EGF receptor, herceptin, angiostatin, or thalidomide. Examples of COX-2 inhibitors include celecoxib, rofecoxib, and etoricoxib.

Other examples of targeting ligands include tumor markers. Non-limiting examples of tumor markers include PSA, ER, PR, CA-125, CA-199, CEA, AFP, an interferon, BRCA1, HER-2/neu, cytoxan, p53 and endostatin. The targeting ligand may also be a folate receptor targeting ligand. Examples include folate, methotrexate and tomudex.

The targeting ligand may also be an apoptotic cell targeting ligand. For example, the apoptotic cell targeting ligand may further be defined as a tumor apoptotic cell targeting ligand. Non-limiting examples include a TRAIL monoclonal antibody, a substrate of caspase-3, and a Bcl family member. Examples of a substrate of caspase-3 include a peptide or polypeptide comprising the amino acid sequence aspartic acid-glutamic acid-valine-aspartic acid. Examples of Bcl family members include Bax, Bcl-xL, Bid, Bad, Bak, and Bcl-2

In some embodiments, the targeting ligand is a hypoxia targeting ligand. For example, the hypoxia targeting ligand may be a tumor hypoxia targeting ligand, a cardiac ischemia marker, a cardiac viability tissue marker, a congestive heart failure marker, or a rest/stress cardiac tissue marker. Non-limiting examples of tumor hypoxia targeting ligands include annexin V, colchicine, a nitroimidazole, mitomycin, metronidazole, 99 mTc-HL91, and Cu-ATSM. Non-limiting examples of cardiac ischemia markers include interleukin-6, tumor necrosis factor alpha, matrix metalloproteinase 9, myeloperoxidase, intercellular and vascular adhesion molecules, soluble CD40 ligand, placenta growth factor, high sensitivity C-reactive protein (hs-CRP), ischemia modified albumin (IMA), free fatty acids, and choline. Non-limiting examples of cardiac viability tissue markers include phospholipase C, myosin light-chain phosphatase, nitric oxide, prostacyclin, endothelin, thromboxane, L-arginine and L-citrulline. Non-limiting examples of congestive heart failure markers include interleukin-1, cardiotrophin-1, insulin-like growth factor, epidermal growth factor, tyrosine kinase receptor, angiotensin II, and metronidazole. Non-limiting examples of rest/stress cardiac tissue markers include a mitogen-activated protein kinase, cyclic adenosine monophosphate, phospholipase C, phosphatidylinositol bisphosphate, isositol trisphosphate, diacylglycerol, a tyrosine kinase, and metronidazole.

Non-limiting examples of peptides contempated as targeting ligands include neuropeptide Y, calcitonin gene-related peptide, substance P, and vasoactive intestinal peptide. Non-limiting examples of nucleotides contemplated as targeting ligands include adenine, thymine, guanine, cytosine, and uracil. Non-limiting examples of antibodies contemplated as targeting ligands include an antibody that binds to a troponin, tropomyosin, a sarcolemmal, a collagen, a matrix metalloproteinase, or a tissue inhibitor of a matrix metalloproteinase.

In some embodiments, the targeting ligand is an antisense molecule or an siRNA, or any small molecule that can inhibit RNA translation. The targeting ligand may also be glutamate pentapeptide.

In particular embodiments, the targeting ligand is an agent that mimics glucose. Non-limiting examples of agents that mimic glucose include deoxyglucose, glucosamine, tetraacetylated glucosamine, neomycin, kanamycin, gentamycin, paromycin, amikacin, tobramycin, netilmicin, ribostamycin, sisomicin, micromicin, lividomycin, dibekacin, isepamicin, astromicin and aminoglycoside. In particular embodiments, the agent that mimics glucose is glucosamine.

In further embodiments, the targeting ligand is a disease receptor targeting ligand. Non-limiting examples of disease receptor targeting ligands include an estrogen, an androgen, luteinizing hormone, luteinizing hormone releasing hormone (LHRH), transferrin, a progestin, tetraacetate mannose, α-β-tyrosine, tyrosine, a tyrosine derivative, estrone, tamoxifen, and α-methyltyrosine.

Regarding compound (I), In certain embodiments, $A_1$=—$(CH_2)_3$—, $A_3$=—$(CH_2)_2$—, $A_2$=—$(CH_2)_2$—, and $A_4$=—$(CH_2)_2$—. In certain embodiments, $A_1$=—$(CH_2)_2$—, $A_3$=—$(CH_2)_2$—, $A_2$=—$(CH_2)_3$—, and $A_4$=—$(CH_2)_3$—. In certain embodiments, $A_1$=—$(CH_2)_2$—, $A_3$=—$(CH_2)_3$—, $A_2$=—$(CH_2)_3$—, and $A_4$=—$(CH_2)_3$—. In certain embodiments, $A_1$=—$(CH_2)_3$—, $A_3$=—$(CH_2)_3$—, $A_2$=—$(CH_2)_3$—, and $A_4$=—$(CH_2)_3$—. In certain embodiments, $A_1$=—$(CH_2)_4$—, $A_3$=—$(CH_2)_3$—, $A_2$=—$(CH_2)_3$—, and $A_4$=—$(CH_2)_3$—. In certain embodiments, $A_1$=—$(CH_2)_4$—, $A_3$=—$(CH_2)_3$—, $A_2$=—$(CH_2)_4$—, and $A_4$=—$(CH_2)_3$—. In certain embodiments, $A_1$=—$(CH_2)_3$—, $A_3$=—$(CH_2)_3$—, $A_2$=—$(CH_2)_4$—, and $A_4$=—$(CH_2)_4$—. In certain embodiments, $A_1$=—$(CH_2)_3$—, $A_3$=—$(CH_2)_4$—, $A_2$=—$(CH_2)_4$—, and $A_4$=—$(CH_2)_4$—. In certain embodiments, $A_1$=—$(CH_2)_4$—, $A_3$=—$(CH_2)_4$—, $A_2$=—$(CH_2)_4$—, and $A_4$=—$(CH_2)_4$—. In certain embodiments that include a targeting ligand, if $A_1$=—$(CH_2)_2$—, $A_3$=—$(CH_2)_2$—, $A_2$=—$(CH_2)_3$—, and if $A_4$ is not —$(CH_2)_3$—; or if $A_1$=—$(CH_2)_2$—, $A_3$=—$(CH_2)_2$—, $A_2$=—$(CH_2)_2$—, and $A_4$ is not —$(CH_2)_2$; then said targeting ligand may be chosen from the group consisting of a disease receptor targeting ligand, a disease cell cycle ligand, an angiogenesis targeting ligand, and an apoptosis targeting ligand.

In particular embodiments, $A_1$=—$(CH_2)_2$—, $A_2$=—$(CH_2)_3$—, $A_3$=—$(CH_2)_2$—, and $A_4$=—$(CH_2)_3$—, and at least one of $R_1$, $R_2$, $R_3$, and $R_4$ is a targeting ligand. In other embodiments, $A_1$=—$(CH_2)_2$—, $A_3$=—$(CH_2)_2$—, $A_2$=—$(CH_2)_3$—, and $A_4$=—$(CH_2)_3$—, and at least one of $R_1$, $R_2$, $R_3$, and $R_4$ is a protecting group. Protecting groups are discussed in greater detail in the specification below. For example, the protecting group may be ethyl trifluoroacetate. Examples of amine protecting groups include benzylchloroformate, p-nitro-chlorobenzylformate, ethylchloroformate, di-tert-butyldicarbonate, triphenylmethyl chloride and methoxytriphenylmethyl chloride.

In still further embodiments, $A_1$=—$(CH_2)_2$—, $A_2$=—$(CH_2)_2$—, $A_3$=—$(CH_2)_2$—, and $A_4$=—$(CH_2)_2$—, and at least one of $R_1$, $R_2$, $R_3$, and $R_4$ is a targeting ligand. In further embodiments, $A_1$=—$(CH_2)_2$—, $A_2$=—$(CH_2)_2$—, $A_3$=—$(CH_2)_2$—, and $A_4$=—$(CH_2)_2$—, and at least one of $R_1$, $R_2$, $R_3$, and $R_4$ is a protecting group. In other embodiments, $A_1$=—$(CH_2)_2$—, $A_2$=—$(CH_2)_2$—, $A_3$=—$(CH_2)_2$—, and $A_4$=—$(CH_2)_2$—. In further embodiments, $A_1$=—$(CH_2)_2$—, $A_2$=—$(CH_2)_3$—, $A_3$=—$(CH_2)_2$—, and $A_4$=—$(CH_2)_3$—. In still further embodiments, $A_1$=—$(CH_2)_2$—, $A_2$=—$(CH_2)_3$—, $A_3$=—$(CH_2)_3$—, and $A_4$=—$(CH_2)_3$—. In further embodiments, $A_1$=—$(CH_2)_3$—, $A_2$=—$(CH_2)_3$—, $A_3$=—$(CH_2)_3$—, and $A_4$=—$(CH_2)_3$—. In other embodiments, $A_1$=—$(CH_2)_4$—, $A_2$=—$(CH_2)_3$—, $A_3$=—$(CH_2)_3$—, and $A_4$=—$(CH_2)_3$—.

In particular embodiments, $A_1$=—$(CH_2)_4$—, $A_2$=—$(CH_2)_4$—, $A_3$=—$(CH_2)_3$—, and $A_4$=—$(CH_2)_3$—. In other particular embodiments, $A_1$=—$(CH_2)_3$—, $A_2$=—$(CH_2)_4$—, $A_3$=—$(CH_2)_3$—, and $A_4$=—$(CH_2)_4$—. In further embodiments, $A_1$=—$(CH_2)_3$—, $A_2$=—$(CH_2)_4$—, $A_3$=—$(CH_2)_4$—, and $A_4$=—$(CH_2)_4$—. In still further embodiments, $A_1$=—$(CH_2)_4$—, $A_2$=—$(CH_2)_4$—, $A_3$=—$(CH_2)_4$—, and $A_4$=—$(CH_2)_4$—. In further embodiments, $A_1$=—$(CH_2)_2$—, $A_2$=—$(CH_2)_3$—, and $A_3$=—$(CH_2)_2$, then $A_4$ is not —$(CH_2)_3$—. In other embodiments, if $A_1$=—$(CH_2)_2$—, $A_2$=—$(CH_2)_2$—, and $A_3$=—$(CH_2)_2$—, then $A_4$ is not —$(CH_2)_2$.

In particular embodiments, the compound is of formula (I), wherein $A_1$, $A_2$, $A_3$, and $A_4$, are each independently —$(CH_2)_x$—, wherein x=2-4; and $R_1$, $R_2$, and $R_3$ are each independently hydrogen,

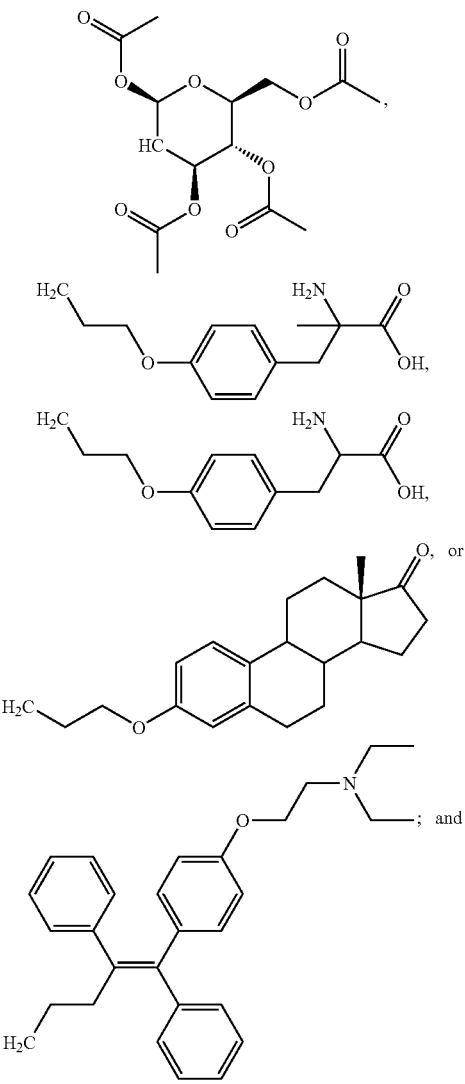

$R_4$ is chosen from the group consisting of:

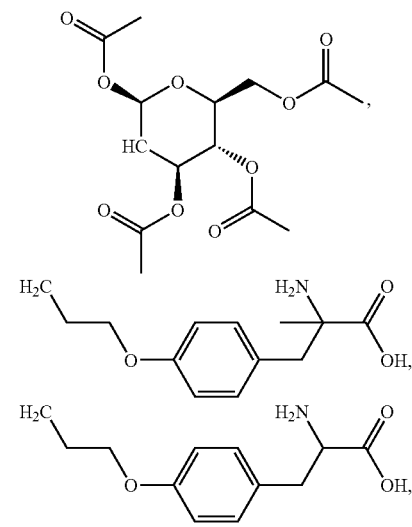

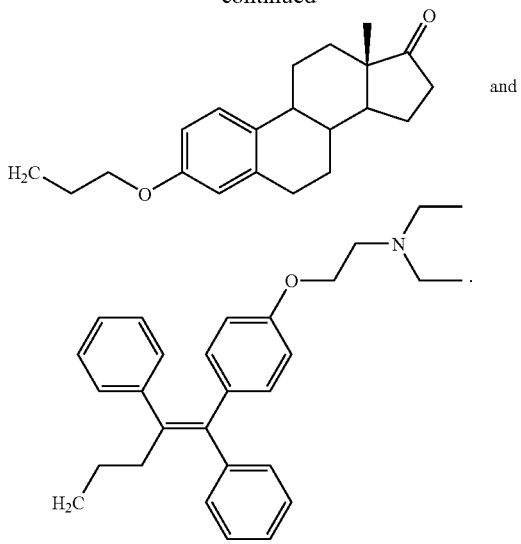

and

In certain particular embodiments, the compound is chelated to a metal ion. Non-limiting examples of metal ions include a technetium ion, a copper ion, an indium ion, a thallium ion, a gallium ion, an arsenic ion, a rhenium ion, a holmium ion, a yttrium ion, a samarium ion, a selenium ion, a strontium ion, a gadolinium ion, a bismuth ion, an iron ion, a manganese ion, a lutecium ion, a cobalt ion, a platinum ion, a calcium ion, and a rhodium ion. In particular embodiments, the metal ion is selected from the group consisting of Tc-99m, Cu-60, Cu-61, Cu-62, Cu-64, Cu-67, In-111, Tl-201, Ga-67, Ga-68, As-72, Re-186, Re-187, Re-188, Ho-166, Y-90, Sm-153, Sr-89, Gd-157, Gd-183, Bi-212, Bi-213, Fe-56, Fe-59, Ac-225, At-211, Ti-45, Mn-55, Lu-177, an iron ion, a manganese ion, a cobalt ion, a platinum ion and a rhodium ion. In particular embodiments, the metal ion is Re-187.

The metal ion may or may not be a radionuclide. Examples of radionuclides include $^{99m}Tc$, $^{188}Re$, $^{186}Re$, $^{153}Sm$, $^{166}Ho$, $^{90}Y$, $^{89}Sr$, $^{67}Ga$, $^{68}Ga$, $^{111}In$, $183Gd$, $^{59}Fe$, $^{225}Ac$, $^{212}Bi$, $^{211}At$, $^{45}Ti$, $^{60}Cu$, $^{61}Cu$, $^{67}Cu$. In particular embodiments, the radionuclide is $^{99m}Tc$. In further particular embodiments, the radionuclide is $^{188}Re$.

In some embodiments, the invention generally pertains to a composition comprising the compound of formula (I) and a pharmaceutically acceptable carrier. In particular embodiments, the composition further comprises a metal ion chelated to the compound of formula (I).

The present invention also pertains to methods of synthesizing $N_4$ compounds of the present invention, methods of synthesizing $N_4$ conjugates of the present invention, and methods of synthesizing metal ion-labeled $N_4$ conjugates of the present invention. Organic (solvent) synthetic methods are described, and can be used to synthesize compounds of high purity.

In general, methods of synthesis the present invention take place in an organic medium. As used herein, "organic medium" refers to solutions and purification methods comprising one or more organic solvents. Solvent choices for the methods of the present invention will be known to one of ordinary skill in the art. Solvent choices may depend, for example, on which one(s) will facilitate the solubilizing of all the reagents, or, for example, which one(s) will best facilitate the desired reaction (particularly if the mechanism of the reaction is known). Solvents may include, for example, polar solvents and/or non-polar solvents. Solvents choices include, but are not limited to, dimethylformamide, dimethylsulfoxide, dioxane, methanol, ethanol, hexane, methylene chloride and/or acetonitrile. In some embodiments, solvents include ethanol, dimethylformamide and/or dioxane. More than one solvent may be chosen for any particular reaction or purification procedure. Water may also be admixed into any solvent choice; this can be done to enhance the solubility of one or more reactants, for example.

Both the targeting ligand and the $N_4$ compound will typically have one or more functional groups. Functional groups and protecting agents are described herein. Persons of skill in the art will understand that any functional group may be protected using a protecting agent as necessary, as described herein. Typically, as is known to those of skill in the art, protecting groups are utilized in organic syntheses and not aqueous syntheses.

In certain embodiments, the targeting ligand comprises a leaving group. The term "leaving group" generally refers to groups readily displaceable by a nucleophile, such as an amine, an alcohol or a thiol nucleophile. Such leaving groups are well known and include, for example, carboxylates, N-hydroxysuccinimide, N-hydroxybenzotriazole, halides, triflates, tosylates, mesylates, alkoxys, thioalkoxys, sulfonyls and the like.

Conjugation between the $N_4$ compound and a targeting ligand may take place via any method and chemical linkage known to those of skill in the art. That is, the targeting ligand may be conjugated or bound to one or more $N_4$ compound in any manner known to those of ordinary skill in the art. In certain embodiments, conjugation between the $N_4$ compound and the targeting ligand takes place in a single step (i.e., a "one-pot" reaction). As is known by those of skill in the art, such one-step reactions are desirable as they save time, help minimize waste reagents and minimize loss of product. Typically, conjugation occurs prior to chelation.

In some embodiments, only the conjugation between an $N_4$ compound and a targeting ligand takes place via organic synthesis (that is, in organic media). In some embodiments, only the synthesis of an $N_4$ compound takes place via organic synthesis. In some embodiments, only the chelation of a valent metal ion takes place via organic synthesis. In certain embodiments, any one or more of these steps take place via organic synthesis.

The N4 compounds, conjugates, and metal ion-labeled N4 conjugates may be prepared via organic synthesis that typically enjoy purities higher than those achieved via aqueous preparations. For example, in some embodiments of the present invention, the compounds and conjugates generated via organic means are between about 90% and about 99.9% pure, compared to between about 50% and about 70% pure for the aqueous product. In certain embodiments, the synthesized compounds and conjugates set forth herein are about or at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9% pure, or higher, or any range derivable therein.

The present invention also generally pertains to methods of imaging, diagnosing, or treating a subject, involving administering to a subject a pharmaceutically effective amount of a metal ion-labeled chelator-targeting ligand conjugate, wherein the chelator-targeting ligand conjugate is any of the compounds discussed above, and wherein the subject is imaged, diagnosed, or treated.

The subject can be any subject, such as a mammal. In particular embodiments, the subject is a human. The metal ion can be any of those metal ions discussed above. In particular embodiments, the chelator-targeting ligand conjugate is chelated to $^{99m}$Tc.

In some embodiments, the method is further defined as a method of treating a subject with a hyperproliferative disease. In particular embodiments, the hyperproliferative disease is cancer. For example, the cancer may be breast cancer, lung cancer, prostate cancer, ovarian cancer, brain cancer, liver cancer, cervical cancer, colon cancer, renal cancer, skin cancer, head and neck cancer, bone cancer, a esophageal cancer, bladder cancer, uterine cancer, lymphatic cancer, stomach cancer, pancreatic cancer, testicular cancer, lymphoma, or leukemia.

In other embodiments, the method is further defined as a method for performing dual radio/chemotherapy. These methods are discussed in greater detail in the specification below.

In some embodiments, the method may involve administering one or more secondary forms of therapy of a hyperproliferative disease. Examples of such therapy include chemotherapy, radiation therapy, surgical therapy, immunotherapy, gene therapy, and hormonal therapy. These are discussed in greater detail in the specification below.

In particular embodiments, the method is further defined as a method for performing dual imaging and chemotherapy in a subject with a hyperproliferative disease. In further embodiments, the method is further defined as a method of diagnosing and assessing efficacy of treatment for a patient with a cardiovascular disease. The cardiovascular disease types may include: peripheral vascular disease, myocardial infarction, cardiovascular ischemia, cardiac or peripheral vascular disease; cardiotoxicity; cardiomyopathy, arrhythmias, valvular disease; right or left congestive heart failure with or without systolic or diastolic dysfunction, and congenital heart disease. In particular embodiments, the cardiovascular disease is a myocardial infarction, myocardial ischemia, peripheral vascular ischemia, or angina pectoris and the method further comprises imaging the heart of the subject with the use of SPECT, PET, SPECT/CT, MRI, SPECT/MRI, PET/CT and PET/MRI. Any part of the cardiovascular system may be imaged such as the myocardium, areas of ischemia in the myocardium or the Peripheral Vascular System, and so forth. Imaging may be by any method or modality known to those of ordinary skill in the art, such as PET, SPECT, or other nuclear medicine-based imaging. In particular embodiments, method of treating a subject involve revascularization techniques such as CABG, PTCA, Stents or a combination of these methods, administration of a metal ion labeled chelator-targeting ligand conjugate that is $^{99m}$Tc-EC-glucosamine or the use of angiogenisis agents such as VEGF or Fibroblast Growth Factors.

In some embodiments, the present invention contemplates a method of imaging to diagnose presence of Cardiovascular Disease or assess efficacy of treatment comprising administering to the subject a pharmaceutically effective amount of any composition as described herein. The subject may be a mammal, such as a human.

The present invention also pertains to a kit that includes any of the compounds discussed above and one or more sealed containers. The compound may be included in the one or more sealed containers. For example, there may be 2, 3, 4, 5, 6, 7, 8, 9, 10, or more sealed containers in each kit. In some embodiments, the kit further includes a reducing agent. Non-limiting examples of reducing agents include tin (II) chloride, triphenylphosphine, or SnCl$_2$. In some embodiments, the kit further includes a metal ion. The metal ion may or may not be in a sealed container that includes the compound discussed above. The metal ion can be any of those metal ions discussed above. Examples include Tc-99m, Cu-60, Cu-61, Cu-62, Cu-64, Cu-67, In-111, Tl-201, Ga-67, Ga-68, As-72, Re-186, Re-187, Re-188, Ho-166, Y-90, Sm-153, Sr-89, Gd-157, Gd-183, Bi-212, Bi-213, Fe-56, Fe-59, Ac-225, At-211, Ti-45, Mn-55, Lu-177, an iron ion, a manganese ion, a cobalt ion, a platinum ion, or a rhodium ion.

Embodiments of the present invention also generally pertain to methods of diagnosis, assessing efficacy of treatment, or imaging in a subject with known or suspected Cardiovascular disease. The subject can be any subject, such as a mammal or animal models used to assess the presence of Cardiovascular disease. The mammal, for example, may be a human or member of the monkey species. Animal models include dogs, cats, rats, mice or rabbits. In preferred embodiments, the subject is a human with known or suspected cardiovascular disease.

The cardiovascular disease can be any disease of the heart or tissue nourished by the vascular system. The vascular system includes coronary arteries, and all peripheral arteries supplying nourishment to the peripheral vascular system and the brain. The vascular system includes arteries, veins, arterioles, venules, and capillaries. Examples of cardiovascular diseases include diseases of the heart, such as myocardial infarction, myocardial ischemia, angina pectoris, congestive heart failure, cardiomyopathy (congenital or acquired), arrhythmia, or valvular heart disease. In particular embodiments, the subject is known or suspected to have myocardial ischemia.

The subject, for example, may be a patient who presents to a clinic with signs or symptoms suggestive of myocardial ischemia or myocardial infarction. Imaging of the heart of the subject to diagnose disease may involve administering to the subject a pharmaceutically effective amount of a metal ion labeled chelator-targeting ligand conjugate synthesized using any of the methods set forth herein. Imaging can be performed using any imaging modality known to those of ordinary skill in the art. In particular embodiments, imaging involves use radionuclide-based imaging technology, such as PET or SPECT. In particular embodiments, the metal ion-labeled radionuclide-targeting ligand conjugate is 99m-Tc-EC-glucosamine. Glucosamine is not actively taken up by viable myocardial tissue but rather is target specific for regions of Ischemia Severity of ischemia can be visually assessed or graded depending on magnitude of the signal that is measured using any method known to those of ordinary skill in the art. In some embodiments, imaging using any of the conjugates set forth herein is performed before, during, or after imaging of the heart using a second imaging agent. For example, the second imaging agent may be thallium imaged by scintigraphy to would define the region of normal myocardial perfusion (non-ischemic tissue).

Myocardial perfusion SPECT (MPS) consist of a combination of a stress modality (exercise or pharmacologic) with rest and stress administration and imaging of radiopharmaceuticals. Thallium has excellent physiologic properties for myocardial perfusion imaging. Being highly extracted during the first pass through the coronary circulation, a linear relationship between blood flow to viable myocardium and thallium uptake has been shown during exercise; however, at very high levels of flow, a "roll-off" in uptake occurs. As an unbound potassium analogue, thallium redistributes over time. Its initial distribution is proportional to regional myocardial perfusion and at equilibrium, the distribution of thallium is proportional to the regional potassium pool, reflecting viable myocardium. The mechanisms of thallium redistribution are differential washout rates between hypoperfused but viable myocardium and normal zones and wash-in to initially hypoperfused zones. The washout rate of thallium is the concentration gradient between the myocardial cell and the blood. There is slower blood clearance of thallium following resting or low-level exercise injection. Diffuse slow washout rates, mimicking diffuse ischemia, may be observed in normal patients who do not achieve adequate levels of stress. Hyperinsulinemic states slow redistribution, leading to an underestimation of viable myocardium; thus fasting is recommended prior to and for 4 hrs following thallium injection. This is why if EC-G is used as an viable agent in combination with thallium it will target the precise area of interest which would be the Ischemic but viable area (see Angello et al., 1987; Gutman et al., 1983; Pohost et al., 1977).

Imaging using any of the metal ion-labeled chelator-targeting ligand conjugates of the present invention may also be performed in conjunction with other diagnostic methods, such as measurement of cardiac isozymes, or cardiac catheterization. The imaging may be performed at various intervals following onset of symptoms, or can be performed to assess for changes in myocardial perfusion over time.

In certain embodiments, the methods involve methods of dual radioisotope imaging and delivery of a therapeutic agent to the heart. For example, the therapeutic agent could be fibroblast growth factor which uses the ECG images for image guidance to create angiogenesis in the viable but ischemic region of the myocardium Other examples of such therapeutic agents include other angiogenisis cardiovascular drugs set forth elsewhere in this specification.

In further embodiments, the kit further includes an antioxidant. Non-limiting examples of antioxidants include vitamin C, tocopherol, pyridoxine, thiamine, and rutin. In some embodiments, the kit includes a transition chelator. Non-limiting examples of transition chelators include glucoheptonate, gluconate, glucarate, citrate, and tartarate.

The present invention also concerns a reagent for preparing an imaging agent, a chemotherapeutic agent or a radio/chemotherapeutic agent, comprising a metal ion-labeled chelator-targeting ligand conjugate, wherein the chelator-targeting ligand conjugate is any of the compounds discussed above. In some embodiments, the metal ion-labeled chelator-targeting ligand conjugate is at least about 70% pure, at least about 75% pure, at least about 80% pure, at least about 85% pure, at least about 90% pure, at least about 95% pure, or at least about 99% pure. In some embodiments, the metal ion-labeled chelator-targeting ligand conjugate is between about 90% and about 99.9% pure.

Another aspect of the present invention relates to a method for the treatment of cancer comprising administering to a subject a compound of the present invention. The subject may be a mammal, such as a human. The compound may be chelated to $^{99m}$Tc, $^{188}$Re, $^{187}$Re, $^{183}$Sm, $^{166}$Ho, $^{90}$Y, $^{89}$Sr, $^{67}$Ga, $^{68}$Ga, $^{111}$In, $^{183}$Gd, $^{59}$Fe, $^{225}$Ac, $^{212}$Bi, $^{211}$At, $^{45}$Ti, $^{60}$Cu, $^{61}$Cu, $^{67}$Cu, $^{64}$Cu, or $^{62}$Cu. The compound may be administered in combination with a second anti-cancer compound, a radiation therapy, or surgery.

Another aspect of the present invention relates to a method for imaging comprising administering to a subject one or more of the compounds of the present invention. The subject may be a mammal, such as a human. The compound may be chelated to $^{99m}$Tc, $^{188}$Re, $^{187}$Re, $^{186}$Re, $^{183}$Sm, $^{166}$Ho, $^{90}$Y, $^{89}$Sr, $^{67}$Ga, $^{68}$Ga, $^{111}$In, $^{83}$Gd, $^{59}$Fe, $^{225}$Ac, $^{212}$Bi, $^{211}$At, $^{45}$Ti, $^{60}$Cu, $^{61}$Cu, $^{67}$Cu, $^{64}$Cu, $^{64}$Cu or $^{62}$Cu. Said imaging may comprise PET imaging or SPET imaging.

The present invention also generally pertains to methods for imaging the brain or spinal cord (neuroendocrine system) of a subject, comprising administering to a subject one or more of the conjugates of the present invention. In some embodiments, for example, the $N_4$ compound is conjugated to a targeting ligand that is capable of crossing the blood-brain barrier of a subject. A non-limiting example of such a targeting ligand is an amino acid, such as tyrosine or an analog of tyrosine such as alpha-methyl tyrosine. Other examples include somatostatin, octreotide, and tryptophan.

The present invention also generally pertains methods of treating a subject with a disorder of the central nervous system of a subject. The disorder of the central nervous system may be, for example, a neurodegenerative disease such as Parkinson's disease, Huntington's disease, amyotrophic lateral sclerosis, Alzheimer disease, or a neuroendocrine tumor. Examples of neuroendocrine tumors include primary and metastatic brain tumors. Examples of primary brain tumors include astrocytomas, glioblastomas, oligodendrogliomas, ependymomas, mixed gliomas, mixed glio-neuronal tumors (tumors displaying a neuronal, as well as a glial component, e.g. gangliogliomas, disembryoplastic neuroepithelial tumors) and tumors originating from neuronal cells (e.g. gangliocytoma, central gangliocytoma). The tumor may be a metastatic tumor. In some embodiments, the disorder of the central nervous system is an inflammatory disease. For example, the disease may be an infectious disease, or an immune disease. In some embodiments, the method of treating the subject with a disorder of the central nervous system is further defined as a method of As used herein, "alkyl" or "alk" refers to a straight, branched or cyclic carbon-carbon or hydrocarbon chain, optionally including alkene or alkyne bonding, containing 1-12 carbons. In some embodiments, lower alkyls are preferred. "Lower alkyl" refers to alkyl radicals comprising 1-4 carbons. Non-limiting examples of lower alkyls include methyl, ethyl, propyl, cyclopropyl, butyl and isopropyl. In certain embodiments, a lower alkyl group may be selected from the group consisting of —$CH_2$—$CH_2$—, —$CH_2$—$CH_2$—$CH_2$— and —$CH_2$—$CH_2$—$CH_2$—$CH_2$—. "Substituted alkyl" refers to an alkyl radical substituted with at least one atom known to those of skill in the art. In certain embodiments, one or more substituents may be selected from the group consisting of hydrogen, halogen, oxo (e.g., ether), hydroxy, alkoxy, silyloxy, cycloalkyl, acyl, aryl, acetyl, carbonyl, thiocarbonyl, cyano, amido, aminocarbonyl, amino, —NH-alkyl, —N(alkyl)$_2$, —NH-cycloalkyl, —N(cycloalkyl)$_2$, —NH-aryl, —N(aryl)$_2$, trialkylsilyloxy, acyloxy, acylamino, bis-acylamino, ester, NO, $NO_2$ and sulfo (e.g., thioether, thioester, sulfonamido, sulfonyl), or any combination thereof. The term "alkyl-COOH" refers to an alkyl radical comprising a carboxylic acid moiety.

As used herein the term "cycloalkyl" refers to carbocycles of three or more atoms, wherein the ring atoms of which may comprise one or more functional group as substituents. Substituents may be selected, in some embodiments, from the group consisting of hydrogen, alkyl, halogen, oxo (e.g., ether), hydroxy, alkoxy, silyloxy, cycloalkyl, acyl, aryl, acetyl, carbonyl, thiocarbonyl, cyano, amido, aminocarbonyl, amino, —NH-alkyl, —N(alkyl)$_2$, —NH-cycloalkyl, —N(cycloalkyl)$_2$, —NH-aryl, —N(aryl)$_2$, trialkylsilyloxy, acyloxy, acylamino, bis-acylamino, ester, NO, $NO_2$ and sulfo (e.g., thioether, thioester, sulfonamido, sulfonyl). In certain embodiments, a cycloalkyl group may comprise one or more heteroatoms; such a heterocyclic non-aromatic cycloalkyl group includes substituents such as piperidinyl, tetrahydropyranyl and tetrahydrothiophenyl.

The term "aryl" refers to a carbocyclic aromatic group, including but not limited to those selected from the group consisting of phenyl, naphthyl, indenyl, indanyl, azulenyl, fluorenyl, and anthracenyl; or a heterocyclic aromatic group, including but not limited to those selected from the group consisting of furyl, furanyl, thienyl, pyridyl, pyrrolyl, oxazolyl, thiazolyl, imidazolyl, pyrazolyl, pyrazolinyl, pyrazolidinyl, isoxazolyl, isothiazolyl, oxadiazolyl, triazolyl, thiadiazolyl, pyridazinyl, pyrimidinyl, pyrazinyl, triazinyl, trithianyl, indolizinyl, indolyl, isoindolyl, indolinyl, thiophenyl, indazolyl, benzimidazolyl, benzthiazolyl, purinyl, quinolizinyl, quinolinyl, isoquinolinyl, innolinyl, phthalazinyl, quinazolinyl, quinoxalinyl, naphthyridinyl, pteridinyl carbazolyl, acridinyl, phenazinyl, phenothiazonyl, phenoxazinyl and any combination or derivative of one or more of these groups.

"Aryl" groups, as defined in this application may independently contain one or more functional groups as substituents. In certain embodiments, substituents may be selected from the group consisting of hydrogen, alkyl, halogen, oxo (e.g., ether), hydroxy, alkoxy, silyloxy, cycloalkyl, acyl, aryl, acetyl, carbonyl, thiocarbonyl, cyano, amido, aminocarbonyl, amino, —NH-alkyl, —N(alkyl)$_2$, —NH-cycloalkyl, —N(cycloalkyl)$_2$, —NH-aryl, —N(aryl)$_2$, trialkylsilyloxy, acyloxy, acylamino, bis-acylamino, ester, NO, NO$_2$ and sulfo (e.g., thioether, thioester, sulfonamido, sulfonyl). Further, any of these substituents may be further substituted with substituents as just described.

The term "amino acid" refers to any of the naturally occurring amino acids, as well as synthetic analogs (e.g., D-stereoisomers of the naturally occurring amino acids, such as D-threonine) and derivatives thereof. α-Amino acids comprise a carbon atom to which is bonded an amino group, a carboxyl group, a hydrogen atom, and a distinctive group referred to as a "side chain." Amino acids comprising an additional methylene group in their backbone are often called β-amino acids. The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine). Unnatural amino acids are also known in the art, as set forth in, for example, Williams (1989); Evans et al. (1990); Pu et al. (1991); Williams at al (1991); and all references cited therein. The present invention includes the side chains of unnatural amino acids as well.

The term "functional group" generally refers to how persons of skill in the art classify chemically reactive groups. Examples of functional groups include hydroxyl, amine, sulfhydryl, amide, carboxyls, carbonyls, etc.

As used herein, "protecting group" refers to a moiety attached to a functional group to prevent an otherwise unwanted reaction of that functional group. Protecting groups are well-known to those of skill in the art. Non-limiting exemplary protecting groups fall into categories such as hydroxy protecting groups, amino protecting groups, sulfhydryl protecting groups and carbonyl protecting groups. Such protecting groups may be found in Greene and Wuts, 1999.

The word "conjugate" and "conjugated" is defined herein as chemically joining within the same molecule. For example, two or more molecules and/or atoms may be conjugated together via a covalent bond, forming a single molecule. The two molecules may be conjugated to each other via a direct connection (e.g., where the compounds are directly attached via a covalent bond) or the compounds may be conjugated via an indirect connection (e.g., where the two compounds are covalently bonded to one or more linkers, forming a single molecule). In other instances, a metal atom may be conjugated to a molecule via a chelation interaction.

The term "N$_4$ conjugate" is defined herein as an N$_4$ compound that has been conjugated to at least one other molecule or atom. The N$_4$ conjugate may comprise a N$_4$ compound that is conjugated to a targeting ligand (e.g., via a covalent bond) and/or a linker (e.g., via a covalent bond) and/or a metal chelate (e.g., via a chelation interaction). The term "N$_4$ conjugate" is used interchangeably herein with "chelator."

As used herein, a "linker-targeting ligand" refers to a compound in which a linker group, such as those described herein, binds the targeting ligand to an annular nitrogen of the compound of formula (I), such that the linker is positioned between the ligand and the annular nitrogen.

As used herein the term "radionuclide" is defined as a radioactive nuclide (a species of atom able to exist for a measurable lifetime and distinguished by its charge, mass, number, and quantum state of the nucleus) which, in specific embodiments, disintegrates with emission of corpuscular or electromagnetic radiation. The term may be used interchangeably with the term "radioisotope."

Compounds as described herein may contain one or more asymmetric centers and thus can occur as racemates and racemic mixtures, single enantiomers, diastereomeric mixtures and individual diastereomers. All possible stereoisomers of the all the compounds described herein, unless otherwise noted, are contemplated as being within the scope of the present invention. The chiral centers of the compounds of the present invention can have the S- or the R-configuration, as defined by the IUPAC 1974 Recommendations. The present invention is meant to comprehend all such isomeric forms of the compounds of the invention.

The claimed invention is also intended to encompass salts of any of the synthesized compounds of the present invention. The term "salt(s)" as used herein, is understood as being acidic and/or basic salts formed with inorganic and/or organic acids and bases. Zwitterions (internal or inner salts) are understood as being included within the term "salt(s)" as used herein, as are quaternary ammonium salts such as alkylammonium salts. Nontoxic, pharmaceutically acceptable salts are preferred as described below, although other salts may be useful, as for example in isolation or purification steps.

Non-limiting examples of acid addition salts include but are not limited to acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pectinate, persulfate, 3-phenylpropionate, picrate, pivalate, propionate, succinate, tartrate, thiocyanate, tosylate and undecanoate.

Non-limiting examples of basic salts include but are not limited to ammonium salts; alkali metal salts such as sodium, lithium, and potassium salts; alkaline earth metal salts such as calcium and magnesium salts; salts comprising organic bases such as amines (e.g., dicyclohexylamine, alkylamines such as t-butylamine and t-amylamine, substituted alkylamines, arylalkylamines such as benzylamine, dialkylamines, substituted dialkylamines such as N-methyl glucamine, trialkylamines, and substituted trialkylamines); and salts comprising amino acids such as arginine, lysine and so forth. The basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myrtistyl and stearyl chlorides, bromides and iodides), arylalkyl halides (e.g., benzyl and phenethyl bromides) and others known in the art.

The term "effective," as that term is used in the specification and/or claims (e.g., "an effective amount," means adequate to accomplish a desired, expected, or intended result.

The term "therapeutic agent" as used herein is defined as an agent which provides treatment for a disease or medical condition. The agent in a specific embodiment improves at least one symptom or parameter of the disease or medical condition. For instance, in tumor therapy, the therapeutic agent reduces the size of the tumor, inhibits or prevents growth or metastases of the tumor, or eliminates the tumor. Examples include a drug, such as an anticancer drug, a gene therapy composition, a radionuclide, a hormone, a nutriceutical, or a combination thereof.

The term "tumor" as used herein is defined as an uncontrolled and progressive growth of cells in a tissue. A skilled artisan is aware other synonymous terms exist, such as neoplasm or malignancy. In a specific embodiment, the tumor is a solid tumor. In other specific embodiments, the tumor derives, either primarily or as a metastatic form, from cancers such as of the liver, prostate, pancreas, head and neck, breast, brain, colon, adenoid, oral, skin, lung, testes, ovaries, cervix, endometrium, bladder, stomach and epithelium.

The term "drug" as used herein is defined as a compound which aids in the treatment of disease or medical condition or which controls or improves any physiological or pathological condition associated with the disease or medical condition.

The term "anticancer drug" as used herein is defined as a drug for the treatment of cancer, such as for a solid tumor. The anticancer drug preferably reduces the size of the tumor, inhibits or prevents growth or metastases of the tumor, and/or eliminates the tumor. The terms "anticancer drug," "anticancer drug," and "anti-cancer compound" are used interchangeably herein.

A person of ordinary skill in the art will recognize that chemical modifications can be made to the compounds of the present invention, as well as compounds employed in the method of the present invention, without departing from the spirit and scope of the present invention. Substitutes, derivatives, or equivalents can also be used, all of which are contemplated as being part of the present invention.

The use of the word "a" or "an" when used in conjunction with the term "comprising" in the claims and/or the specification may mean "one," but it is also consistent with the meaning of "one or more," "at least one," and "one or more than one." As used herein "another" may mean at least a second or more.

It is contemplated that any embodiment discussed in this specification can be implemented with respect to any method or composition of the invention, and vice versa. Furthermore, compositions of the invention can be used to achieve the methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4A: Cellular uptake of $^{68}Ga$—$N_4$-DG2 (cyclam) in rat mammary tumor cells. In vitro cellular uptake using 13762 cells showed increased uptake of $^{68}Ga$—$N_4$-DG whereas $^{68}Ga$—$N_4$ showed poor uptake. FIG. 4B: Cellular uptake study of $^{99m}Tc$—$N_4$-DG (cyclal). 50,000 cells/well were plated and allowed to reach 70-80% confluency. Tracers were administered at 4 µCi/well and incubated at 37° C. for 0.5-2 hrs. Cells were then harvested and radioactivity was counted and quantified. FIG. 4C: In vitro study of $^{99m}Tc$-labeled $N_4$, Biotin, AMT and DOTA compounds in 13762 breast cancer cell line. 50,000 cells/well were plated and allowed to reach 70-80% confluency. Tracers were administered at 4 µMC1/well and incubated at 37° C. for 0.5-1.5 hrs.

FIG. 5A: $^{68}Ga$—$N_4$-DG vs $^{18}F$-FDG (pPET). A similar distribution pattern was observed between $^{68}Ga$—$N_4$-DG (cyclam) and $^{18}F$-FDG. FIG. 5B: pPET images of $^{68}Ga$—$N_4$. Mammary tumor-bearing rats injected with 400 µCi $^{68}Ga$—$N_4$. Selected images were shown at 2 hours post-injection.

FIG. 10. $^{68}$Ga pPET imaging. Mammary tumor-bearing rats injected with 400 μCi $^{68}$Ga—N$_4$-AMT. Whole body images showed that tumor (right leg) could be imaged at 2 hours post-injection.

FIG. 18. Triprotection of cyclam.

FIG. 21. de-t-butoxycarboxylation

FIG. 22. de-trifloroacetylation

DESCRIPTION OF ILLUSTRATIVE EMBODIMENTS

Figure 1:
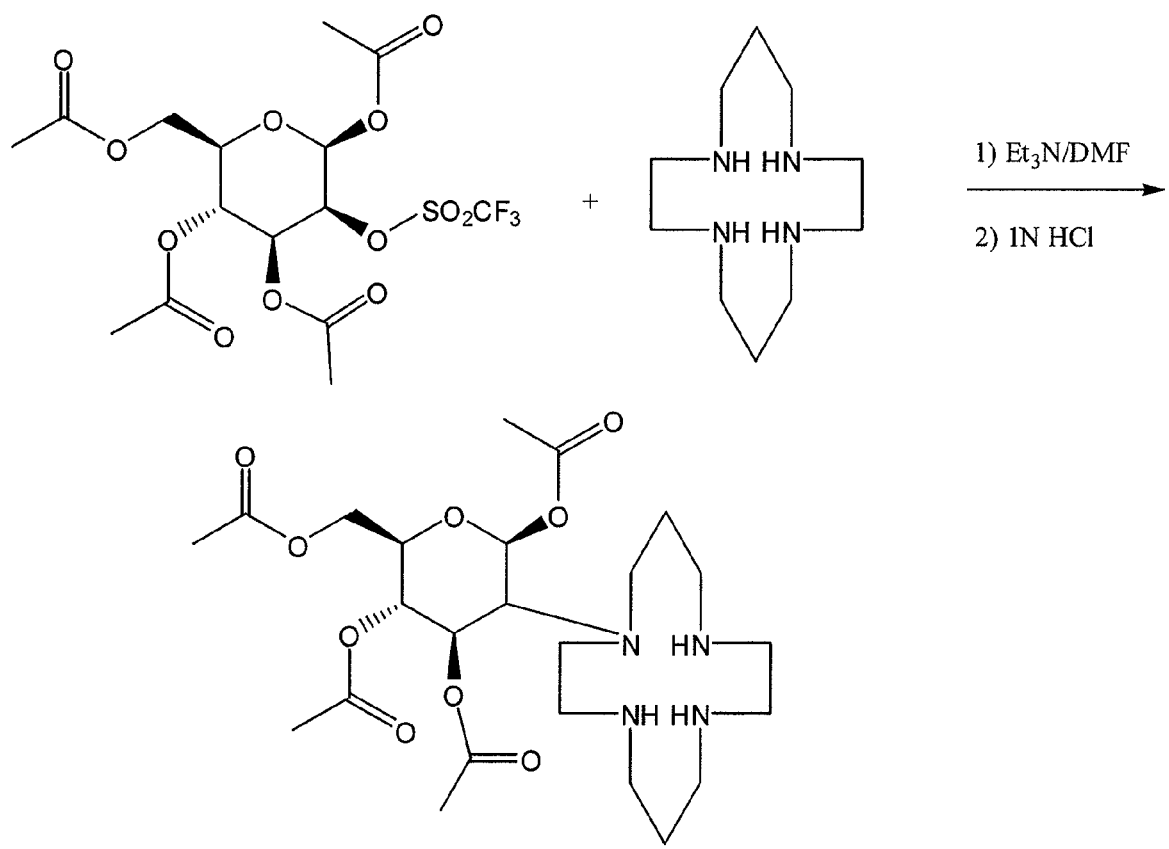
FIG. 1. Synthesis of $N_4$-DG.

The present invention is based on the finding of certain novel N$_4$ compounds, and the finding that these compounds can be applied in the diagnosis and treatment of a disease in a subject, in the imaging of a site of interest in the subject, and/or in dual imaging/therapy of a subject.

I. N$_4$ Compounds

The present invention provides a method by which N$_4$ compounds, which are typically hydrophobic chelators, may be conjugated to hydrophobic molecules to produce novel compounds that may be used for purposes including imaging and radiotherapy. Certain N$_4$ compounds may be obtained from commercial sources such as Sigma-Aldrich Chemical Co. (Milwaukee, Wis.). U.S. Pat. No. 5,880,281 describes a method for producing certain N$_4$ compounds.

In certain embodiments, an N$_4$ compound is a compound of formula (I),

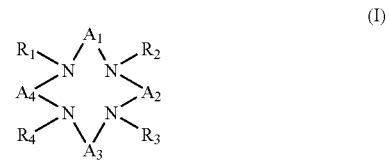

wherein A$_1$, A$_2$, A$_3$, and A$_4$ are alkyl, and R$_1$, R$_2$, R$_3$, and R$_4$ are hydrogen. Several non-limiting N$_4$ compounds are shown below.

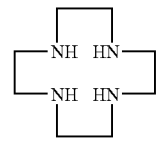 [SMILES: C1CNCCNCCNCCN1]

Registry Number: 294-90-6
CA Index Name: 1,4,7,10-Tetraazacyclododecane (6CI,8CI, 9CI)
Other Names Cyclen; NSC 629374; Tetraaza-12-crown-4

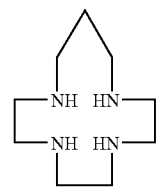

Registry Number: 295-14-7
CA Index Name: 1,4,7,10-Tetraazacyclotridecane (6CI,8CI, 9CI)
Other Names Cyclam 13

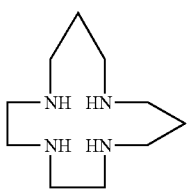 [SMILES: C1CNCCCNCCNCCNC1]

Registry Number: 52877-36-8
CA Index Name: 1,4,7,11-Tetraazacyclotetradecane (9CI)
Other Names Isocyclam

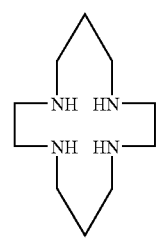

Registry Number: 295-37-4
CA Index Name: 1,4,8,11-Tetraazacyclotetradecane (6CI, 7CI,8CI,9CI)
Other Names Cyclam; JM 1498; NSC 180811

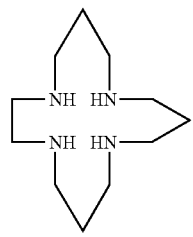 [SMILES: C1CNCCCNCCNCCCNC1]

Registry Number: 15439-16-4
CA Index Name: 1,4,8,12-Tetraazacyclopentadecane (8CI, 9CI)
Other Names Cyclal

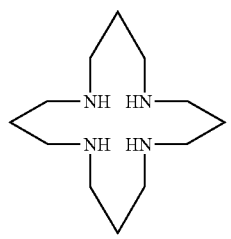 [SMILES: C1CNCCCNCCCNCCCNC1]

Registry Number: 24772-41-6
CA Index Name: 1,5,9,13-Tetraazacyclohexadecane (8CI, 9CI)

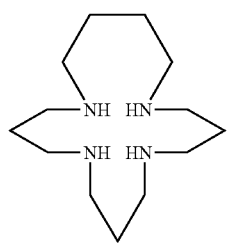 [SMILES: C1CCNCCCNCCCNCCCNC1]

Registry Number: 43031-32-9
CA Index Name: 1,5,9,13-Tetraazacycloheptadecane (9CI)

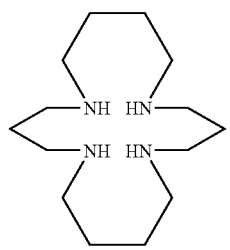 [SMILES: C1CCNCCCNCCCCNCCCNC1]

Registry Number: 68966-28-9
CA Index Name: 1,5,10,14-Tetraazacyclooctadecane (9CI)

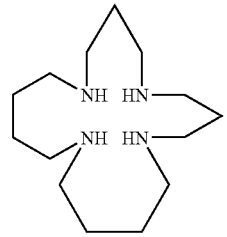 [SMILES: C1CCNCCCNCCCNCCCCNC1]

Name: 1,5,9,14-Tetraazacyclooctadecane

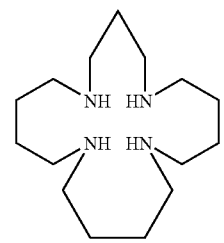 [SMILES: C1CCNCCCCNCCCNCCCCNC1]

Name: 1,5,10,15-Tetraazacyclononadecane

Registry Number: 3713-77-7
CA Index Name: 1,6,11,16-Tetraazacycloeicosane (8CI,9CI)

$N_4$ compounds can be used as chelators. For example, cyclam and other $N_4$ compounds were tested for their ability to alleviate acute cadmium poisoning (Srivastava et al., 1996). U.S. Pat. No. 4,141,654 describes certain compounds with structural similarity to $N_4$ compounds that may be used to chelate actinide ions. U.S. Pat. No. 5,648,063 discloses compounds with structural similarity to $N_4$ compounds which can chelate metal ions and may also be used in certain NMR diagnostic procedures. U.S. Pat. No. 6,071,490 utilizes a modified cyclen for PET imaging. U.S. Pat. No. 6,613,305 discloses vitamin $B_{12}$ attached to various $N_4$ compounds. In certain embodiments an $N_4$ compound that is not conjugated to a targeting ligand may be used for imaging and therapy. Any discussion or embodiment herein comprising an $N_4$ conjugate is specifically contemplated to alternatively comprise an $N_4$ compound that is not conjugated to a targeting ligand.

The term "$N_4$ conjugate" is defined herein as an $N_4$ compound that has been conjugated to at least one other molecule or atom. The $N_4$ conjugate may comprise a $N_4$ compound that is conjugated to a targeting ligand (e.g., via a covalent bond) and/or a linker (e.g., via a covalent bond) and/or a metal chelate (e.g., via a chelation interaction).

Certain embodiments of the present invention relate to $N_4$ conjugates, methods for producing $N_4$ conjugates, and uses of $N_4$ conjugates. In certain embodiments, an $N_4$ conjugate is a compound of formula (I):

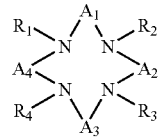

(I)

wherein $A_1$, $A_2$, $A_3$, and $A_4$, are alkyl or substituted alkyl; and $R_1$, $R_2$, $R_3$, and $R_4$ are each independently H, alkyl, substituted alkyl, a funtional group, a targeting ligand, or any combination of one or more of these groups. In certain embodiments, the targeting ligand is a disease receptor targeting ligand, a disease cell cycle targeting ligand, a disease cell glycolysis targeting ligand, a tumor angiogenesis targeting ligand, a tumor apoptosis targeting ligand, a tumor targeting ligand, an angiogenesis/antiangiogenesis targeting ligand, a gene expression marker, an antimicrobial, an antisense molecule, a sugar, an agent that mimics glucose, an EGF receptor ligand, a COX-2 inhibitor, an amino acid, an amino acid derivative, a peptide, a nucleotide, an antibody, a DNA topoisomerase inhibitor, a glycolysis marker, an antimetabolite ligand, a hypoxia targeting ligand, an apoptosis targeting ligand, a DNA intercalator, a receptor marker, an organ specific ligand, an anti-cancer drug, a chemotherapeutic agent, a cardiovascular drug, an imaging moiety, a drug-based ligand, a protecting group,

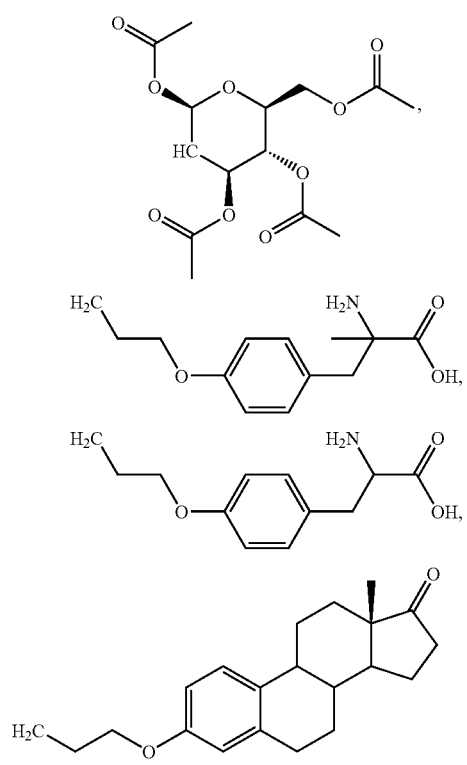

and

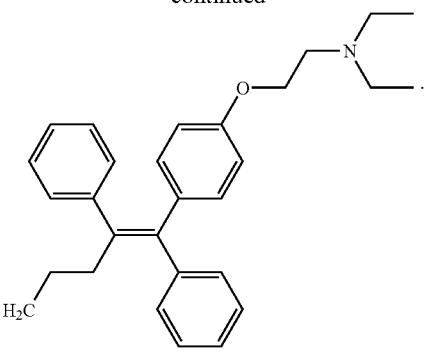

In particular embodiments, $R_4$ is selected from the group consisting of:

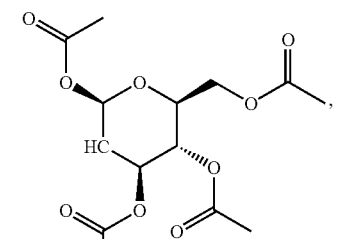

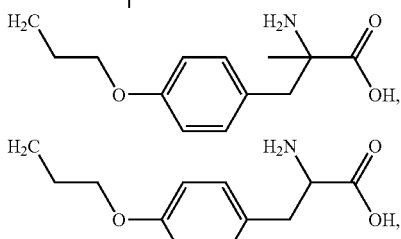

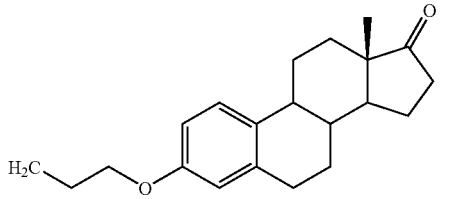

and

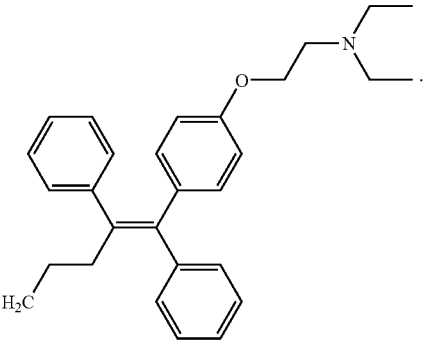

In certain embodiments, the inclusion of any particular $A_1$, $A_2$, $A_3$, $A_4$, $R_1$, $R_2$, $R_3$ or $R_4$ group specifically contemplates the exclusion of that particular group.

The $N_4$ conjugate may have a metal ion chelated to it. The metal atom may be radioactive or non-radioactive.

II. Targeting Ligands

A "targeting ligand" is defined herein to be a molecule or part of a molecule that binds with specificity to another molecule. Those of ordinary skill in the art are familiar with the numerous agents that can be employed as targeting ligands in the context of the present invention. Non-limiting examples of targeting ligands are discussed above. There may be overlap among targeting ligand groups: for example, a particular compound may be both an an agent that mimics glucose and a receptor marker.

In some embodiments of the compositions of the present invention, a targeting ligand is a therapeutic ligand or drug. A "therapeutic ligand" is defined herein to refer to any therapeutic agent, or drug. A "therapeutic agent" or "drug" is defined herein to include any molecule or substance that can be administered to a subject, or contacted with a cell or tissue, for the purpose of treating a disease or disorder, or preventing a disease or disorder, or treating or preventing an alteration or disruption of a normal physiologic process. For example, a therapeutic ligand may be an anti-cancer moiety, such as a chemotherapeutic agent.

Examples of certain targeting ligands which may be used the present invention can be found in Table 1. In certain embodiments, an anti-cancer drug may be used as a targeting ligand. Anti-cancer drugs are well known in the art (e.g., Connors, 1996). Table 2 in U.S. Pat. No. 6,692,724, which is incorporated herein by reference in its entirety, lists several examples of anti-cancer drugs which may be used as targeting ligands in various embodiments of the present invention.

TABLE 1

| Targets for $N_4$ conjugates | Examples of Targeting Ligands |
| --- | --- |
| Tumor Angiogenesis | Celecoxib, C225, angiostatin |
| Disease Receptor | tamoxifen, α-β tyrosine, tyrosine, α-methyltyrosine, luteinizing hormone, transferrin, somatostatin, androgen, estrogen, estrone, progesterone, tetraacetate mannose, |
| Disease Cell Cycle | adenosine, penciclovir |
| Pharmaceutical Agent Assessment | carnitine, puromycin |
| Apoptosis Targeting | TRAIL monoclonal antibody, caspase-3 substrate, Bcl family member |

Additional details regarding certain targeting ligands are set forth below.

A. Chemotherapeutic Agents as Targeting Ligands

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of anti-cancer ligands include any chemotherapeutic agent known to those of ordinary skill in the art. Examples of such chemotherapeutic agents include, but are not limited to, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristin, vinblastin and methotrexate, or any analog or derivative variant of the foregoing. In certain particular embodiments, the anti-cancer ligand is methotrexate.

Other examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authramycin, azaserine, bleomycins, cactinomycin, carabicin, canninomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene; aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor and a HER2 expression inhibitor; vaccines such as gene therapy vaccines and pharmaceutically acceptable salts, acids or derivatives of any of the above.

Additional examples of anti-cancer agents include those drugs of choice for cancer chemotherapy listed in Table 2:

TABLE 2

Cancer Chemotherapy Drugs
The table that follows lists drugs used for treatment of cancer in the USA and Canada and their major adverse effects. The Drugs of Choice listing based on the opinions of Medical Letter consultants. Some drugs are listed for indications for which they have not been approved by the U.S. Food and Drug Administration. Anti-cancer drugs and their adverse effects follow. For purposes of the present invention, these lists are meant to be exemplary and not exhaustive.

DRUGS OF CHOICE

| Cancer | Drugs of Choice | Some alternatives |
|---|---|---|
| Adrenocortical** | Mitotane | Doxorubicin, streptozocin, |
|  | Cisplatin | etoposide |
| Bladder* | Local: Instillation of BCG | Instillation of mitomycin, |
|  | Systemic: Methotrexate + vinblastine + doxorubicin + claplatin (MVAC) | doxorubicin or thiotape |
|  |  | Pecitaxel, substitution of |
|  | Claplatin + Methotrexate + vinblastine (CMV) | carboplatin for claplatin in combinations |
| Brain |  |  |
| Anaplastic astrocytoma* | Procarbazine + lamuatine + vincristine | Carmustine, Claplatin |
| Anaplastic oligodendro-Giloma* | Procarbazine + lamustine + vincristine | Carmustine, Claplatin |
| Gilabiastome** | Carmustine or lamustine | Procarbazine, claplatin |
| Medulloblastoma | Vincristine + carmustine ± mechiorethamine ± methotrexate | Etoposide |
|  | Mechiorethamine + vincristine + procarbazine + prednisone (MOPP) |  |
|  | Vincristine + claplatin ± cyclophosphamide |  |
| Primary central nervous system lymphoma | Methotrexate (high dose Intravenous and/or Intrathecal) ± cytarabine (Intravenous and/or Intrathecal) |  |
|  | Cyclophosphamide + Doxorubicin + vincristine + prednisone (CHOP) |  |
| Breast | Adjuvant[1]: Cyclophosphamide + methotrexate + fluorouracil (CMF); | Paclitaxel; thiotepa + Doxorubicin + vinblastine; mitomycin + vinblastine; |
|  | Cyclophosphamide + Doxorubicin ± fluorouracil (AC or CAF); Tamoxifen | mitomycin + methotrexate + mitoxantrone; fluorouracil |
|  | Metastatic: Cyclophosphamide + methotrexate + fluorouracil (CMF) or | by continuous infusion; Bone marrow transplant[3] |
|  | Cyclophosphamide + duxorubicin ± fluorouracil (AC or CAF) for receptor-negative and/or hormone-refractory; |  |
|  | Tamoxifen for receptor-positive and/or hormone-sensitive[2] |  |
| Cervix** | Claplatin | Chlorambucil, vincristine, |
|  | Ifosfamide with means | fluorouracil, Doxorubicin, |
|  | Bleomycin + ifosfamide with means + claplatin | methotrexate, altretamine |
| Chorlocarcinoma | Methotrexate ± leucovorin | Methotrexate + dactinomycin + cyclophosphamide (MAC) |
|  | Dactinomycin |  |
|  |  | Etoposide + methotrexate + dactinomycin + cyclophosphamide + vincristine |
| Colorectal* | Adjuvant colon[4]: Fluorouracil + levam-isole; | Hepatic metastases: |
|  | fluorouracil + leucovorin | Intrahepatic-arterial |
|  | Metastatic: fluorouracil + leucovorin | floxuridine |
|  |  | Mitomycin |
| Embryonal rhabdomyosar-coma[5] | Vincristine + dectinomycin ± cyclophasphamide | Same + Doxorubicin |
|  | Vincristine + ifosfamide with means + etoposide |  |

TABLE 2-continued

Cancer Chemotherapy Drugs
The table that follows lists drugs used for treatment of cancer in the USA and
Canada and their major adverse effects. The Drugs of Choice listing based on the
opinions of Medical Letter consultants. Some drugs are listed for indications for which
they have not been approved by the U.S. Food and Drug Administration. Anti-cancer
drugs and their adverse effects follow. For purposes of the present invention, these lists
are meant to be exemplary and not exhaustive.

DRUGS OF CHOICE

| Cancer | Drugs of Choice | Some alternatives |
|---|---|---|
| Endometrial** | Megastrol or another progestin | fluorouracil, tamoxifen, altretamine |
| | Doxorubicin + claplatin ± cyclophosphamide | |
| Esophageal* | Claplatin + fluorouracil | Doxorubicin, methotraxate, mitomycin |
| Ewing's sarcoma[5] | Cyclophosphamide (or ifosfamide with means) + Doxorubicin + vincristine (CAV) ± dactinomycin | CAV + etoposide |
| Gastric** | Fluorouracil ± leucavorin | Claplatin Doxorubicin, etoposide, methotrexate + leucovorin, mitomycin |
| Head and neck squambus cell*[6] | Claplatin + fluorouracil | Blomycin, carboplatin, paclitaxel |
| | Methotrexate | |
| Islet cell** | Streptozocin + Doxorubicin | Streptozocin + fluorouracil; chlorozotocint[†]; octreotide |
| Kaposi's sarcoma* (Aids-related) | Etoposide or interferon alfa or vinblastine | Vincristine, Doxorubicin, bleomycin |
| | Doxorubicin + bleomycin + vincristine or vinbiastine (ABV) | |
| Leukemia | | |
| Acute lymphocytic leukemia (ALL)[7] | Induction: Vincristine + prednisone + asparaginase ± daunorubicin CNS prophylaxis: Intrathecal methotrexate ± systemic high-dose methotrexate with leutovorin ± Intrathecal cytarabine ± Intrathecal hydrocortisone Maintenance: Methotrexate + mercaptopurine Bone marrow transplant.[3 8] | Induction: same ± high-dose methotrexate ± cyterabine; pegaspargase instead of asparaginese Teniposide or etoposide High-dose cytarabine Maintenance: same + periodic vincristine + prednisone |
| Acute myeloid leukemia (AML)[9] | Induction. Cytsrahine + either daunorubicin or idaruhicin Post Induction: High-dose cytarahine ± other drugs such as etoposide Bone marrow transplant[3]. | Cytarahine + mitoxentrone High-dose cyterabine |
| Chronic lymphocytic leukemia (CLL) | Chloranibucil ± prednisone Fludarabin | Cladribine, cyclophosphamide, pentostatin, vincristine, Doxorubicin |
| Chronic myeloid leukemia (CML)[10] | | |
| Chronic phase | Bone marrow transplant[3] Interferon alfa Hydroxyures | Busulfan |
| Accelerated[11] | Bone marrow transplant[3] | Hydroxyures, busulfen |
| Blast crisis[11] | Lymphoid: Vincristine + prednisone + L-separaginess + intrathecal methotrexate (±maintenance with methotrexate + 8-marcaptopurine) | Tretinoln[†] Amsecrine,[†] azacitidine Vincristine ± plicamycin |
| Hairy cell Leukemia | Pentostatin or cladribine | Interferon alfa, chlorambucil, fludarabin |
| Liver** | Doxorubicin Fluorouracil | Intrahepatic-arterial floxuridine or claplatin |
| Lung, small cell (cat cell) | Claplatin + etoposide (PE) Cyclophosphamide + doxorubicin + vincristine (CAV) PE alternated with CAV Cyclophosphamide + etoposide + claplatin (CEP) Duxorubicin + cyclophosphamide + etoposide (ACE) | Ifosfamide with means + carboplatin + etoposide (ICE) Daily oral etoposide Etoposide + ifosfamide with means + claplatin (VIP Paclitaxel |
| Lung (non-small cell)** | Claplatin + etoposide Claplatin + Vinblastine ± mitomycin Claplatin + vincrisine | Claplatin + fluorouracil + leucovorin Carboplatin + paclitaxel |
| Lymphomas | | |
| Hodgkin's[12] | Doxorubicin + bleomycin + vinblastine + dacarbazine (ABVD) ABVD alternated with MOPP Mechlorethamine + vincristine + procarbazine | Mechlorethamine + vincristine + procarbazine + prednisone (MOPP) Chlorambusil + vinblastine + procarbazine + prednisone ± carmustine |

TABLE 2-continued

Cancer Chemotherapy Drugs
The table that follows lists drugs used for treatment of cancer in the USA and
Canada and their major adverse effects. The Drugs of Choice listing based on the
opinions of Medical Letter consultants. Some drugs are listed for indications for which
they have not been approved by the U.S. Food and Drug Administration. Anti-cancer
drugs and their adverse effects follow. For purposes of the present invention, these lists
are meant to be exemplary and not exhaustive.

DRUGS OF CHOICE

| Cancer | Drugs of Choice | Some alternatives |
|---|---|---|
| Non-Hodgkin's | (±prednisone) + doxorubicin + bleomycin + vinblastine (MOP[P]-ABV) | Etoposide + vinbiastine + doxorubicin<br>Bone marrow transplant[3] |
| Burkitt's lymphoma | Cyclophosphamide + vincristine + methotrexate<br>Cyclophosphamide + high-dose cytarabine ± methotrexate with leutovorin<br>Intrathecal methotrexate or cytarabine | Ifosfamide with means<br>Cyclophosphamide + doxombicin + vincrletine + prednisone (CHOP) |
| Diffuse large-cell lymphoma | Cyclophosphamide + doxorubicin + vincristine + prednisone (CHOP) | Dexamethasone sometimes substituted for prednisone<br>Other combination regimens, which may include methotrexate, etoposide, cytarabine, bleomycin, procarbazine, ifosfamide and mitoxantrone<br>Bone marrow transplant[3] |
| Follicular lymphoma | Cyclophosphamide or chlorambusil | Same ± vincristine and prednisone, ± etoposide<br>Interferon alpha, cladribine, fludarabin<br>Bone marrow transplant[3]<br>Cyclophosphamide + doxorubicin + vincristine + prednisone (CHOP) |
| Melanoma** | Interferon Alfa<br>Dacarbazine | Carmustine, lomustine, cisplatin<br>Dacarbazine + clapletin + carmustine + tamoxifen<br>Aldesleukin |
| Mycosis fungoides* | PUVA (psoralen + ultraviolet A)<br>Mechlorethamine (topical)<br>Interferon alfa<br>Electron beam radiotherapy<br>Methotrexate | Isotretinoin, topical carmustine, pentosistin, fludarabin, cladribine, photopheresis (extra-corporeal photochemitherapy), chemotherapy as in non-Hodgkin's lymphoma |
| Myloma* | Melphelan (or cyclophosphamide) + prednisons<br>Melphalan ± carmustine + cyclophosphamide + prednisons + vincristine<br>Dexamethasone + doxorubicin + vincristine (VAD)<br>Vincristine + carmustine + doxorubicin + prednisons (VBAP) | Interferon alfa<br>Bone marrow transplant[3]<br>High-dose dexamethasons |
| Neuroblastoma* | Doxorubicin + cyclophosphamide + claplatin + teniposide or etoposide<br>doxorubicin + cyclophosphamide<br>Claplatin + cyclophosphamide | Carboplatin, etoposide<br>Bone marrow transplant[3] |
| Osteogenic sarcoma[5] | Doxorubicin + claplatin ± etopside ± ifosfamide | Ifosfamide with means, etoposide, carboplatin, high-dose methotrexate with leucovorin<br>Cyclophosphamide + etoposide |
| Ovary | Claplatin (or carboplatin) + paclitaxel<br>Claplatin (or carboplatin) + cyclophosphamide (CP) ± doxorubicin (CAP) | Ifosfamide with means, paclitaxel, tamoxifen, melphalan, altretamine |
| Pancreatic** | Fluorouracil ± leucovorin | Gemoltabinet |
| Prostate | Leuprolide (or goserelln) + flutamide | Estramustine + vinblastine, aminoglutethimide + hydrocortleone, estramustine + etoposide, diethylstllbestrol, nilutamide |
| Renal** | Aldesleukin<br>Inteferon alfa | Vinblastine, floxuridine |
| Retinoblestoma[5]* | Doxorubicin + cyclophosphamide + claplatin + etoposide + vincristina | Carboplatin, etoposide, Ifosfamide with means |

TABLE 2-continued

Cancer Chemotherapy Drugs
The table that follows lists drugs used for treatment of cancer in the USA and
Canada and their major adverse effects. The Drugs of Choice listing based on the
opinions of Medical Letter consultants. Some drugs are listed for indications for which
they have not been approved by the U.S. Food and Drug Administration. Anti-cancer
drugs and their adverse effects follow. For purposes of the present invention, these lists
are meant to be exemplary and not exhaustive.

DRUGS OF CHOICE

| Cancer | Drugs of Choice | Some alternatives |
|---|---|---|
| Sarcomas, soft tissue, adult* | Doxorubicin + decarbazine + cyclophosphamide + Ifosfamide with means | Mitornyeln + doxorubicin + claplatin Vincristina, etoposide |
| Testicular | Claplatin + etoposide + bleomycin (PEB) | Vinbiestine (or etoposide) + Ifosfamide with means + claplatin (VIP) Bone marrow transplant[3] |
| Wilms' tumor[5] | Dectinomycln + vincriatine + doxorubicin + cyclophosphamide | Ifosfamide with means, etoposide, carboplatin |

\*Chemotherapy has only moderate activity.
\*\*Chemotherapy has only minor activity.
[1]Tamoxifen with or without chemotherapy is generally recommended for postmenopausal estrogen-receptor-positive, mode-positive patients and chemotherapy with or without tamoxifen for premenopausal mode-positive patients. Adjuvant treatment with chemotherapy and/or tamoxifen is recommended formode-negative patients with larger tumors or other adverse prognostic indicators.
[2]Megastrol and other hormonal agents may be effective in some patients with tamoxifen fails.
[3]After high-dose chemotherapy (Medical Letter, 34:79, 1982).
[4]For rectal cancer, postoperative adjuvant treatment with fluorouracil plus radiation, preceded and followed by treatment with fluorouracil alone.
[5]Drugs have major activity only when combined with surgical resection, radiotherapy or both.
[6]The vitamin A analog lactratinoln (Acgutana) can control pre-neoplastic lesions (leukoplakia) and decreases the rate of second primary tumors (Banner et al, 1994).
[†]Available in the USA only for investigational use.
[7]High-risk patients (e.g., high counts, cytogenetic abnormalities, adults) may require additional drugs for induction, maintenance and "Intensificiation" (use of additional drugs after achievement of remission). Additional drugs include cyclophosphamida, mitoxantrone and thioguanine. The results of one largecontrolled trial in the United Kingdom suggest that Intensificiation may improve survival in all children with ALL (Chasselle et al, 1995).
[8]Patients with a poor prognosis initially or those who relapse after remission.
[9]Some patients with acute promyelocytic leukemia have had complete responses to tratinoin. Such treatment can cause a toxic syndrome characterized primarily by fever and respiratory distress (Warrell, Jr et al, 1993).
[10]Allogeheic HLA-identical sibling bone marrow transplantation can cure 40% to 70% of patients with CML in chronic phase, 18% to 28% of patients with accelerated phase CML, and <15% patients in blast crisis. Disease-free survival after bone marrow transplantations adversely influenced by age >50 years, duration of disease >3 years from diagnosis, and use of one-antigen-mismatched or matched-unrelateddonor marrow. Interferon also may be curative in patients with chronic phase CML who achieve a complete cytogenetic response (about 10%); it is the treatment of choice for patents >80 years old with newly diagnosed chronic phase CML and for all patients who are not candidates for an allgensic bone marrow transplant. Chemotherapy alone is palliative.
[11]If a second chronic phase is achieved with any of these combinations, allogeneic bone marrow transplant should be considered. Bone marrow transplant in second chronic phase may be curative for 30% to 35% of patients with CML.
[12]Limited-stage Hodgkin's disease (stages 1 and 2) is curable by radiotherapy. Disseminated disease (stages 3b and 4) require chemotherapy. Some intermediate stages and selected clinical situations may benefit from both.
+ Available in the USA only for investigational use.

B. DNA Intercalators as Targeting Ligands

DNA intercalating agents are one of the most widely used classes of cancer chemotherapeutic agents currently employed for the management of human cancers. These agents, which are typically polycyclic, aromatic and planar, stack between base pairs of DNA and induce local structural changes, such as the unwinding of the double helix and lengthening of the DNA strand. These structure modifications lead to functional changes, often the inhibition of transcription and replication processes. As such, DNA intercalators are typically mutagens and are often carcinogenic (e.g., benzopyrene diol epoxide, bisbenzimide, aflatoxin and ethidium bromide).

In some embodiments of the present invention, the targeting ligand is a DNA intercalator. Non-limiting examples of DNA intercalators include those selected from the group consisting of 7-aminoactinomycin, etihidium, proflavin, daunomycin, doxorubicin and thalidomide.

C. Cardiovascular Drugs as Targeting Ligands

A "cardiovascular drug" is defined herein to refer to any therapeutic agent that can be applied in the treatment or prevention of a disease of the heart and/or blood vessels.

Non-limiting examples of cardiovascular drugs contemplated as targeting ligands in the present invention include antihyperlipoproteinemic agents, antiarteriosclerotic agents, antithrombotic agents, fibrinolytic agents, antiplatelet agents, blood coagulants, thrombolytic agents, antiarrhythmic agents, antihypertensive agents, vasopressors, anti-angiotension II agents, afterload-preload reduction agents, diuretics and inotropic agents.

In certain embodiments, the cardiovascular drug is an agent that lowers the concentration of one of more blood lipids and/or lipoproteins, known herein as an "antihyperlipoproteinemic," which can be applied in the treatment of athersclerosis and thickenings or blockages of vascular tissues. Examples include an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof. Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate. Non-limiting examples of resins/bile acid sequesterants include cholestyramine (cholybar, questran), colestipol (colestid) and polidexide. Non-limiting examples of HMG CoA reductase inhibitors include lovastatin (mevacor), pravastatin (pravochol) or simvastatin (zocor). Non-limiting examples of nicotinic acid derivatives include nicotinate, acepimox, niceritrol, nicoclonate, nicomol and oxiniacic acid. Non-limiting examples of thyroid hormones and analogs thereof include etoroxate, thyropropic acid and thyroxine. Non-limiting examples of miscellaneous antihyperlipoproteinemics include acifran, azacosterol, benfluorex, β-benzalbutyramide, carnitine, chondroitin sulfate, clomestrone, detaxtran, dextran sulfate sodium, 5,8,11,14,17-eicosapentaenoic acid, eritadenine, furazabol, meglutol, melinamide, mytatrienediol, ornithine, γ-oryzanol, pantethine, pentaerythritol tetraacetate, α-phenylbutyramide, pirozadil, probucol (lorelco), β-sitosterol, sultosilic acid-piperazine salt, tiadenol, triparanol and xenbucin. A non-limiting example of an antiarteriosclerotic includes pyridinol carbamate.

In certain embodiments, the cardiovascular drug is an agent that aids in the removal or prevention of blood clots. Non-limiting examples of antithrombotic and/or fibrinolytic agents include anticoagulants, anticoagulant antagonists, antiplatelet agents, thrombolytic agents, thrombolytic agent antagonists or combinations thereof. Examples of antithrombotic agents include aspirin and wafarin (coumadin). Examples of anticoagulants include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin. Non-limiting examples of antiplatelet agents include aspirin, a dextran, dipyridamole (persantin), heparin, sulfinpyranone (anturane) and ticlopidine (ticlid). Non-limiting examples of thrombolytic agents include tissue plaminogen activator (activase), plasmin, pro-urokinase, urokinase (abbokinase) streptokinase (streptase) and anistreplase/APSAC (eminase).

In some embodiments, the cardiovascular drug is a blood coagulant. Non-limiting examples of a blood coagulation promoting agents include thrombolytic antagonists and anticoagulant antagonists. Non-limiting examples of anticoagulant antagonists include protamine and vitamin K1.

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

The cardiovascular drug may be an antiarrhythmic agent. Non-limiting examples of antiarrhythmic agents include Class I antiarrhythmic agents (sodium channel blockers), Class II antiarrhythmic agents (beta-adrenergic blockers), Class II antiarrhythmic agents (repolarization prolonging drugs), Class IV antiarrhythmic agents (calcium channel blockers) and miscellaneous antiarrhythmic agents. Non-limiting examples of sodium channel blockers include Class IA, Class IB and Class IC antiarrhythmic agents. Non-limiting examples of Class IA antiarrhythmic agents include disppyramide (norpace), procainamide (pronestyl) and quinidine (quinidex). Non-limiting examples of Class IB antiarrhythmic agents include lidocaine (xylocalne), tocamide (tonocard) and mexiletine (mexitil). Non-limiting examples of Class IC antiarrhythmic agents include encamide (enkaid) and flecamide (tambocor). Non-limiting examples of a β-blocker, otherwise known as a α-adrenergic blocker, a β-adrenergic antagonist or a Class II antiarrhythmic agent, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain aspects, the β-blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol. Non-limiting examples of an agent that prolong repolarization, also known as a Class III antiarrhythmic agent, include amiodarone (cordarone) and sotalol (betapace). Non-limiting examples of a calcium channel blocker, otherwise known as a Class IV antiarrhythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a miscellaneous calcium channel blocker such as bencyclane, etafenone, magnesium, mibefradil, or perhexyline. In certain embodiments a calcium channel blocker comprises a long-acting dihydropyridine (nifedipine-type) calcium antagonist. Non-limiting examples of miscellaneous antiarrhythmic agents include adenosine (adenocard), digoxin (lanoxin), acecamide, ajmaline, amoproxan, aprindine, bretylium tosylate, bunaftine, butobendine, capobenic acid, cifenline, disopyranide, hydroquinidine, indecamide, ipatropium bromide, lidocaine, lorajmine, lorcamide, meobentine, moricizine, pirmenol, prajmaline, propafenone, pyrinoline, quinidine polygalacturonate, quinidine sulfate and viquidil.

Other examples of cardiovascular drugs include antihypertensive agents. Non-limiting examples of antihypertensive agents include sympatholytic, α/β-blockers, α-blockers, anti-angiotensin II agents, beta blockers, calcium channel blockers, vasodilators and miscellaneous antihypertensives. Non-limiting examples of an α-blocker, also known as an α-adrenergic blocker or an α-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin. In certain embodiments, an antihypertensive agent is both an α- and β-adrenergic antagonist. Non-limiting examples of an α/β-blocker comprise labetalol (normodyne, trandate). Non-limiting examples of anti-angiotension II agents include angiotensin converting enzyme inhibitors and angiotension II receptor antagonists. Non-limiting examples of angiotension converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-II type-1 receptor blocker (ARBS), include angiocandesartan, eprosartan, irbesartan, losartan and valsartan. Non-limiting examples of a sympatholytic include a centrally acting sympatholytic or a peripherially acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin). In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexyline, pimethylline, trapidil, tricromyl, trimetazidine, troInitrate phosphate and visnadine. In certain aspects, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain aspects, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a suflonamide derivative. Non-limiting examples of arylethanolamine derivatives include amosulalol, bufuralol, dilevalol, labetalol, pronethalol, sotalol and sulfinalol. Non-limiting examples of benzothiadiazine derivatives include althizide, bendroflumethazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothiazide, meticrane, metolazone, paraflutizide, polythizide, tetrachlormethiazide and trichlormethiazide. Non-limiting examples of N-carboxyalkyl(peptide/lactam) derivatives include alacepril, captopril, cilazapril, delapril, enalapril, enalaprilat, fosinopril, lisinopril, moveltipril, perindopril, Non-limiting examples of dihydropyridine derivatives include amlodipine, felodipine, isradipine, nicardipine, nifedipine, nilvadipine, nisoldipine and nitrendipine. Non-limiting examples of guanidine derivatives include bethanidine, debrisoquin, guanabenz, guanacline, guanadrel, guanazodine, guanethidine, guanfacine, guanochlor, guanoxabenz and guanoxan. Non-limiting examples of hydrazines/phthalazines include budralazine, cadralazine, dihydralazine, endralazine, hydracarbazine, hydralazine, pheniprazine, pildralazine and todralazine. Non-limiting examples of imidazole derivatives include clonidine, lofexidine, phentolamine, tiamenidine and tolonidine. Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate. Non-limiting examples of reserpine derivatives include bietaserpine, deserpidine, rescinnamine, reserpine and syrosingopine. Non-limiting examples of sulfonamide derivatives include ambuside, clopamide, furosemide, indapamide, quinethazone, tripamide and xipamide.

Other examples of cardiovascular drugs include vasopressors. Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

Other examples of cardiovascular drugs include agents that can be applied in the treatment or prevention of congestive heart failure. Non-limiting examples of agents for the treatment of congestive heart failure include anti-angiotension II agents, afterload-preload reduction treatment, diuretics and inotropic agents. Examples of afterload-preload reduction agents include hydralazine (apresoline) and isosorbide dinitrate (isordil, sorbitrate). Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furtherene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetamide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretamide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexyline, ticrnafen and urea. Non-limiting examples of a positive inotropic agent, also known as a cardiotonic, include acefylline, an acetyldigitoxin, 2-amino-4-picoline, aminone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythropnleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol. In particular aspects, an intropic agent is a cardiac glycoside, a β-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include aminone (inocor). Antianginal agents may comprise organonitrates, calcium channel blockers, beta blockers and combinations thereof. Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

D. Angiogenesis Targeting Ligands

Throughout this application, "angiogenesis targetring" refers to the use of an agent to bind to neovascular tissue. Throughout this application, "tumor angiogenesis targeting" refers to the use of an agent to bind to tumor neovascularization and tumor cells. Agents that are used for this purpose are known to those of ordinary skill in the art for use in performing various tumor measurements, including measurement of the size of a tumor vascular bed, and measurement of tumor volume. Some of these agents bind to the vascular wall. One of ordinary skill in the art would be familiar with the agents that are available for use for this purpose. Non-limiting examples of angiogenesis targeting ligands include celecoxib, C225, herceptin, angiostatin, and thalidomide, which have been developed for the assessment of biochemical process on angiogenesis.

In certain embodiments, a tumor targeting ligand may associate with tumor tissues by targeting the hypoxia associated with tumor cells. Examples of tumor targeting ligands that target hypoxic tissues include nitroimidazole and metronidazole, and these ligands may also be used to target other hypoxic tissues that are hypoxic due to a reason other than cancer (e.g., stroke).

E. Apoptosis Targeting Ligands

"Apoptosis targeting" refers to the use of an agent to bind to a cell that is undergoing apoptosis or is at risk of undergoing apoptosis. These agents are generally used to provide an indicator of the extent or risk of apoptosis, or programmed cell death, in a population of cells, such as a tumor. One of ordinary skill in the art would be familiar with agents that are used for this purpose. Certain examples of apoptosis targeting ligands are shown in Table 1. An "apoptosis targeting ligand" is a ligand that is capable of performing "apoptosis targeting" as defined in this paragraph. An example of a tumor apoptosis targeting ligand includes TRAIL (TNF-related apoptosis inducing ligand) monoclonal antibody. TRAIL is a member of the tumor necrosis factor ligand family that rapidly induces apoptosis in a variety of transformed cell lines. Other examples of apoptosis targeting ligands include a substrate of caspase-3, such as peptide or polypeptide that includes the 4 amino acid sequence aspartic acid-glutamic acid-valine-aspartic acid (for example, a peptide or chelator that includes the amino acid sequence aspartic acid-glutamic acid-valine-aspartic acid), and any member of the Bcl family. Examples of Bcl family members include, for example, Bax, Bcl-xL, Bid, Bad, Bak and Bcl-2. One of ordinary skill in the art would be familiar with the Bcl family, and their respective substrates.

Apoptosis suppressors are targets for drug discovery, with the idea of abrogating their cytoprotective functions and restoring apoptosis sensitivity to tumor cells (Reed, 2003).

Significant research is directed towards the creation and evaluation of new compounds that affect apoptosis, such as restoring apoptosis sensitivity to cancer cells (Reed, 2003). It is envisioned that the present invention may be used to expedite the evaluation and/or efficacy of known and/or subsequently discovered tumor apoptosis targeting compounds.

F. Disease Receptor Targeting Ligands

As "disease receptor targeting ligands," certain agents are exploited for their ability to bind to certain cellular receptors that are overexpressed in disease states, such as cancer, neurological diseases and cardiovascular diseases. Examples of such receptors which are targeted include estrogen receptors, amino acid transporters, androgen receptors, pituitary receptors, transferrin receptors, progesterone receptors, and glucose transporters. Non-limiting examples of agents that can be applied as disease-receptor targeting ligands include androgen, estrogen, somatostatin, progesterone, transferrin, luteinizing hormone and luteinizing hormone antibody and those shown in Table 1. Disease receptor targeting ligands (e.g., pentetreotide, octreotide, transferrin, and pituitary peptide) bind to cell receptors, some of which are overexpressed on certain cells.

Estrogen, estrone and tamoxifen target the estrogen receptor. Estrogen receptors are overexpressed in certain kinds of cancer, and $N_4$ conjugates that comprise an estrogen receptor targeting ligand may be used in certain embodiments to image tumors. The expression of estrogen receptors is also altered in the diseases of osteoporosis and endometriosis. It is anticipated that an $N_4$ conjugate comprising an estrogen receptor targeting ligand may be used to image other diseases such as osteoporosis and endometriosis.

Glucose transporters are overexpressed in various diseased cells such as certain cancerous cells. Tetraacetate mannose, deoxyglucose, certain polysaccharides (e.g., neomycin, kanamycin, tobramycin), and monosaccharides (e.g., glucosamine) also bind the glucose transporter and may be used as disease receptor targeting ligands. Since these ligands are not immunogenic and are cleared quickly from the plasma, receptor imaging would seem to be more promising compared to antibody imaging.

Similarly, amino acid transporters are also overexpressed in various diseased cells such as certain cancerous cells. Amino acids and/or amino acid derivatives (e.g., serine, tyrosine, alpha methyltyrosine) may be used as disease receptor targeting ligands.

Additional receptor targeting ligands are available and may be conjugated to $N_4$ compounds. Other examples of disease receptor targeting ligands include leuteinizing hormone and transferrin. EGFR-TK expression and biologic correlation of specific receptor targeting in brain and other tissues. Diseases associated with changes in dopaminergic synthetic rate such as chemotoxin-induced neuron loss (MPTP, cocaine), drug-induced neurotoxicity (such as related to treatment with chemotherapy drugs), Parkinson's disease (PD), Huntington disease, dementia and cognition, psychosis, depression, schizophrenia, obesity and stem cell therapy follow-up.

The folate receptor is included herein as another example of a disease receptor. Folate receptors (FRs) are overexposed on many neoplastic cell types (e.g., lung, breast, ovarian, cervical, colorectal, nasopharyngeal, renal adenocarcinomas, malignant melanoma and ependymomas), but primarily expressed only several normal differentiated tissues (e.g., choroid plexus, placenta, thyroid and kidney) (Weitman et al., 1992a; Campbell et al., 1991; Weitman et al., 1992b; Holm et al., 1994; Ross et al., 1994; Franklin et al., 1994; Weitman et al., 1994). FRs have been used to deliver folate-conjugated protein toxins, drug/antisense oligonucleotides and liposomes into tumor cells overexpressing the folate receptors (Ginobbi et al., 1997; Leamon and Low, 1991; Leamon and Low, 1992; Leamon et al., 1993; Lee and Low, 1994). Furthermore, bispecific antibodies that contain anti-FR antibodies linked to anti-T cell receptor antibodies have been used to target T cells to FR-positive tumor cells and are currently in clinical trials for ovarian carcinomas (Canevari et al., 1993; Bolhuis et al., 1992; Patrick et al., 1997; Coney et al., 1994; Kranz et al., 1995).

Examples of folate receptor targeting ligands include folic acid and analogs of folic acid. In certain embodiments, a folate receptor targeting ligand is selected from the group consisting of folate, folic acid, methotrexate and tomudex. Folic acid as well as antifolates such as methotrexate enter into cells via high affinity folate receptors (glycosylphosphatidylinositol-linked membrane folate-binding protein) in addition to classical reduced-folate carrier system (Westerhof et al., 1991; Orr et al., 1995; Hsuch and Dolnick, 1993).

G. Tumor Targeting Ligands

"Tumor targeting" refers to the ability of a compound to preferentially associate with tumors (e.g., cancerous, precancerous, benign). A "tumor targeting ligand" refers to a compound which preferentially binds to or associates with tumor tissues, as compared to non-tumor tissues. Ligands (e.g., small molecules or antibodies) which preferentially target tumors are well known in the art, and it is anticipated that tumor targeting ligands that are currently known, or which may be subsequently discovered, may be used with the present invention. Disease receptor targeting refers to the ability of a compound to preferentially associate with receptors whose altered expression correlates with presence of a disease. For example, disease receptor targeting can be used to treat diseases associated with altered dopaminergic synthetic rate.

H. Disease Cell Cycle Targeting Ligands

Disease cell cycle targeting refers to the targeting of agents that are upregulated in proliferating cells. Compounds used for this purpose can be used to measure various parameters in cells, such as tumor cell DNA content.

Certain disease cell cycle targeting ligands are nucleoside analogues. For example, pyrimidine nucleoside (e.g., 2'-fluoro-2'-deoxy-5-iodo-1-β-D-arabinofuranosyluracil [FIAU], 2'-fluoro-2'-deoxy-5-iodo-1-β-D-ribofuranosyluracil [FIRU], 2'-fluoro-2'-5-methyl-β-D-arabinofuranosyluracil [FMAU], 2'-fluoro-2'-deoxy-5-iodovinyl-1-β-D-ribofuranosyluracil [IVFRU]) and acycloguanosine: 9-[(2-hydroxy-1-(hydroxymethyl)ethoxy)methyl]guanine (GCV) and 9-[4-hydroxy-3-(hydroxy-methyl)butyl]guanine (PCV) (Tjuvajev et al., 2002; Gambhir et al., 1998; Gambhir et al., 1999) and other $^{18}$F-labeled acycloguanosine analogs, such as 8-fluoro-9-[(2-hydroxy-1-(hydroxymethyl)ethoxy)methyl]guanine (FGCV) (Gambhir et al., 1999; Namavari et al., 2000), 8-fluoro-9-[4-hydroxy-3-(hydroxymethyl)butyl]guanine (FPCV) (Gambhir et al., 2000; Iyer et al., 2001), 9-[3-fluoro-1-hydroxy-2-propoxy methyl]guanine (FHPG) (Alauddin et al., 1996; Alauddin et al., 1999), and 9-[4-fluoro-3-(hydroxymethyl)butyl]guanine (FHBG) (Alauddin and Conti, 1998; Yaghoubi et al., 2001) have been developed as reporter substrates for imaging wild-type and mutant (Gambhir et al., 2000) HSV1-tk expression. One of ordinary skill in the art would be familiar with these and other agents that are used for disease cell cycle targeting.

Examples of disease targeting ligands include, for example, adenosine and penciclovir. The antiviral nucleoside analog FHBG (a penciclovir analog), another disease targeting ligand, has for in vivo measurement of cell proliferation using PET (Alauddin et al., 2001), and it is anticipated that similar targeting ligands may be used with the present invention.

I. Hypoxia Targeting Ligands

Hypoxia targeting refers to the targeting of agents that are upregulated in hypoxic cells. Compounds used for this purpose can be used to measure various parameters in cells, such as tumor cell hypoxia, resistance or residual content.

In some embodiments of the present invention, the targeting ligand is a tumor hypoxia targeting ligand. For example, tumor cells are more sensitive to conventional radiation in the presence of oxygen than in its absence; even a small percentage of hypoxic cells within a tumor could limit the response to radiation (Hall, 1988; Bush et al., 1978; Gray et al., 1958). Hypoxic radioresistance has been demonstrated in many animal tumors but only in few tumor types in humans (Dische, 1991; Gatenby et al., 1988; Nordsmark et al., 1996). The occurrence of hypoxia in human tumors, in most cases, has been inferred from histology findings and from animal tumor studies. In vivo demonstration of hypoxia requires tissue measurements with oxygen electrodes and the invasiveness of these techniques has limited their clinical application.

Examples of tumor hypoxia targeting ligands include annexin V, colchicine, nitroimidazole, mitomycin and metronidazole.

Misonidazole, an example of a tumor hypoxia targeting ligand, is a hypoxic cell sensitizer, and labeling MISO with different radioisotopes (e.g., $^{18}$F, $^{123}$I, $^{99m}$Tc) may be useful for differentiating a hypoxic but metabolically active tumor from a well-oxygenated active tumor by PET or planar scintigraphy. [$^{18}$F]Fluoromisonidazole (FMISO) has been used with PET to evaluate tumors hypoxia. Recent studies have shown that PET, with its ability to monitor cell oxygen content through [$^{18}$F]FMISO, has a high potential to predict tumor response to radiation (Koh et al., 1992; Valk et al., 1992; Martin et al., 1989; Rasey et al., 1989; Rasey et al., 1990; Yang et al., 1995). PET gives higher resolution without collimation, however, the cost of using PET isotopes in a clinical setting is prohibitive. Accordingly, non-limiting examples of hypoxia targeting ligands include misonidazole (2-nitroimidazole) and metronidazole (5-nitroimidazole) analogues.

J. Cardiac Ischemia Markers

In some embodiments, the targeting ligand is a cardiac ischemia marker. A cardiac ischemia marker is a ligand that is relatively selective for ischemic cardiac tissue. Non-limiting examples of cardiac ischemia markers include interleukin-6, tumor necrosis factor alpha), matrix metalloproteinase 9, myeloperoxidase, intercellular and vascular adhesion molecules, soluble CD40 ligand, placenta growth factor, high sensitivity C-reactive protein [hs-CRP], and ischemia modified albumin [IMA], free fatty acids, and choline, and adenosine.

K. Viability Cardiac Tissue Markers

In some embodiments, the targeting ligand is a viability cardiac tissue marker. A viability cardiac tissue marker refers to a ligand that is relatively selective for viable cardiac tissue compared to nonviable cardiac tissue. Non-limiting examples of cardiac viability tissue markers include those selected from the group consisting of phospholipase C, myosin light-chain phosphatase, nitric oxide, prostacyclin, endothelin, thromboxane, L-arginine and L-citrulline.

L. Congestive Heart Failure Markers

In some embodiments, the targeting ligand is a congestive heart failure marker. A congestive heart failure marker is a ligand that is relatively selective for cardiac tissue of a heart in congestive heart failure compared to normal healthy heart tissue. Non-limiting examples of congestive heart failure markers include those selected from the group consisting of interleukin-1, cardiotrophin-1, insulin-like growth factor, epidermal growth factor, carnetin, tyrosine kinase receptor and angiotensin II.

M. Rest/Stress Cardiac Tissue Markers

In some embodiments, the targeting ligand is a rest/stress cardiac tissue marker. A rest/stress cardiac tissue marker is a ligand that is relatively selective for cardiac tissue that is stressed compared to non-stressed (at rest) cardiac tissue, or vice versa. Non-limiting examples of rest/stress cardiac tissue markers include those selected from the group consisting of mitogen-activated protein kinase, cyclic adenosine monophosphate, phospholipase C, phosphatidylinositol bisphosphate, isositol trisphosphate, diacylglycerol and tyrosine kinases.

N. Disease Cell Glycolysis Targeting Ligands

Disease cell glycolysis targeting refers to the targeting of agents that are upregulated by glucose utilization in cells. Compounds used for this purpose can be used to measure various parameters in cells, such as tumor cell growth, inflammation degrees. Disease cell glycolysis targeting ligands include glucose, galactose, mannose and ribose analogues.

O. Agents That Mimic Glucose as Targeting Ligands

Agents that mimic glucose are also contemplated for inclusion as targeting ligands. Such agents can also be considered "glucose analogs" or "glucose derivatives."

Glucose is utilized by living organisms through the glycolysis pathway. Compounds such as neomycin, kanamycin, gentamycin, amikacin, tobramycin, netilmicin, ribostamycin, sisomicin, micromicin, lividomycin, dibekacin, isepamicin, and astromicin belong to a group called aminoglycosides.

In terms of structure, agents that mimic glucose typically have a glucose ring structure. Exceptions exist, however, such as puromycin, which has a pentose ring structure, but which can still be considered an agent that mimics glucose.

In terms of function, aminoglycosides are used as antibiotics that block the glycolysis pathway by their property of being structurally similar to glucose and thus, they are functionally considered as agents that mimic glucose. When these aminoglycosides are used in imaging studies, there are no detectable pharmacological effects.

The word "mimic," as defined by the American Heritage Dictionary fourth edition, means "to resemble closely or simulate." Aminoglycosides are functionally utilized through the glycolytic pathway by virtue of their structural similarity to glucose and block the glycolysis pathway. Hence, aminoglycosides are considered to mimic or simulate glucose in structural and functional manner.

Non-limiting examples of chemical structures with their PubChem Database (NCBI) identifier CID number are as follows: Amikacin CID 37768; Aminoglycoside CID 191574; Astromicin CID 65345; Deoxy-glucose CID 439268; D-glucosamine CID 441-477; Dibekacin CID 3021; Gentamicin CID 3467; Glucose CID 5793; Isepamicin CID 456297; Kanamycin CID 5460349; Lividomycin CID 72394; Micromicin CID 107677; Neomycin CID 504578; Netilmycin CID 441306; Puromycin CID 439530; Ribostamycin CID 33042; Sisomicin CID 36119; and Tobramycin CID 36294.

References which describe the glycolysis blocking by aminoglycosides include, for example, Tachibana et al., 1976; Borodina et al., 2005; Murakami et al., 1996; Hoelscher et al., 2000; Yang et al., 2004; Michalik et al., 1989; Murakami et al., 1997; Diamond et al., 1978; Hostetler and Hall, 1982; Benveniste and Davies, 1973; Hu, 1998; Yanai et al., 2006; Myszka et al., 2003; Nakae and Nakae, 1982; Ozmen et al., 2005; and Tod et al., 2000.

In certain embodiments, agents that mimic glucose, or sugars, include neomycin, kanamycin, gentamycin, paromycin, amikacin, tobramycin, netilmicin, ribostamycin, sisomicin, micromicin, lividomycin, dibekacin, isepamicin, astromicin, and the aminoglycosides glucose and glucosamine. In particular embodiments, the targeting ligand is glucosamine.

P. Antibodies as Targeting Ligands

In further embodiments of the present invention, the targeting ligand is an antibody. Any antibody is contemplated as a targeting ligand in the context of the present invention. For example, the antibody may be a monoclonal antibody. One of ordinary skill in the art would be familiar with monoclonal antibodies, methods of preparation of monoclonal antibodies, and methods of use of monoclonal antibodies as ligands. In certain embodiments of the present invention, the monoclonal antibody is an antibody directed against a tumor marker. In some embodiments, the monoclonal antibody is monoclonal antibody C225, monoclonal antibody CD31, or monoclonal antibody CD40. The antibody may also be selected from the group consisting of troponins, tropomyosin, sarcolemmals, collagen, matrix metalloproteinases and tissue inhibitors of matrix metalloproteinases.

Q. Antimicrobials as Targeting Ligands

Any antimicrobial is contemplated for inclusion as a targeting ligand. Preferred antimicrobials include ampicillin, amoxicillin, penicillin, clindamycin, gentamycin, kanamycin, neomycin, natamycin, nafcillin, rifampin, tetracycline, vancomycin, bleomycin, doxycyclin, amikacin, netilmicin, streptomycin, tobramycin, loracarbef, ertapenem, imipenem, meropenem, cefadroxil, cefazolin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, teicoplanin, azithromycin, clarithromycin, dirithromycin, erythromycin, roxithromycin, troleandomycin, aztreonam, azlocillin, carbenicillin, cloxacillin, dicloxacillin, flucloxacillin, mezlocillin, piperacillin, ticarcillin, bacitracin, colistin, polymyxin b, ciprofloxacin, enoxacin, gatifloxacin, levofloxacin, lomefloxacin, moxifloxacin, norfloxacin, ofloxacin, trovafloxacin, mafenide, prontosil, sulfacetamide, sulfamethizole, sulfanilimide, sulfasalazine, sulfisoxazole, trimethoprim, trimethoprim-sulfamethoxazole, demeclocycline, minocycline, oxytetracycline, arsphenamine, chloramphenicol, ethambutol, fosfomycin, furazolidone, isoniazid, linezolid, metronidazole, mupirocin, nitrofurantoin, platensimycin, pyrazinamide, quinupristin, dalfopristin, spectinomycin and telithromycin.

Antifungals include natamycin, rimocidin, filipin, nystatin, amphotericin B, miconazole, ketoconazole, clotrimazole, econazole, bifonazole, butoconazole, finticonazole, isoconazole, oxiconazole, sertaconazole, sulconazole, tioconazole, fluconazole, itraconazole, ravuconazole, posaconazole, vorconazole, terconazole, terbinafine, amorolfine, naftifine, butenafine, anidulafungin, caspofungin, micafungin, ciclopirox, flucytosine, griseofulvin, gentian violet, haloprogin, tolnaftate, undecyclenic acid, amantadine, polymycin, acyclovir and ganciclovir for fungi. One of ordinary skill in the art would be familiar with the various agents that are considered to be antimicrobials.

R. Antisense Molecules as Targeting Ligands

Antisense molecules interact with complementary strands of nucleic acids, modifying expression of genes. In some embodiments, the targeting ligand is an antisense molecule or an siRNA such as such as guanine, uracil, glucocorticoids, progesterones, androgens, mineralocorticoids, estrogen, thyroxine, vitamin D3 and retinoic acid.

Some regions within a double strand of DNA code for genes, which are usually instructions specifying the order of amino acids in a protein along with regulatory sequences, splicing sites, noncoding introns and other complicating details. For a cell to use this information, one strand of the DNA serves as a template for the synthesis of a complementary strand of RNA. The template DNA strand is called the antisense strand and the RNA is said to be sense (the complement of antisense). Because the DNA is double-stranded, the strand complementary to the antisense strand is also called sense and has the same base sequence as the mRNA (though T bases in DNA are substituted with U bases in RNA). For example:

DNA strand 1: sense strand
DNA strand 2: antisense strand (copied to)→RNA strand (sense).

Many forms of antisense have been developed and can be broadly categorized into enzyme-dependent antisense or steric blocking antisense. Enzyme-dependent antisense includes forms dependent on RNase H activity to degrade target mRNA, including single-stranded DNA, RNA, and phosphorothioate antisense. Double stranded RNA acts as enzyme-dependent antisense through the RNAi/siRNA pathway, involving target mRNA recognition through sense-antisense strand pairing followed by target mRNA degradation by the RNA-induced silencing complex (RISC). Steric blocking antisense (RNase-H independent antisense) interferes with gene expression or other mRNA-dependent cellular processes by binding to a target sequence of mRNA and getting in the way of other processes. Steric blocking antisense includes 2'-O alkyl (usually in chimeras with RNase-H dependent antisense), peptide nucleic acid (PNA), locked nucleic acid (LNA) and Morpholino antisense. Cells can produce antisense RNA molecules naturally, which interact with complementary mRNA molecules and inhibit their expression.

Antisense nucleic acid molecules have been used experimentally to bind to mRNA and prevent expression of specific genes. Antisense therapies are also in development; the FDA has approved a phosphorothioate antisense oligo, fomivirsen (Vitravene), for human therapeutic use.

S. Imaging Moieties as Targeting Ligands

In certain embodiments of the compositions of the present invention, the targeting ligand is an imaging moiety. As defined herein, an "imaging moiety" is a part of a molecule that is a agent or compound that can be administered to a subject, contacted with a tissue, or applied to a cell for the purpose of facilitating visualization of particular characteristics or aspects of the subject, tissue, or cell through the use of an imaging modality. Imaging modalities are discussed in greater detail below. Any imaging agent known to those of ordinary skill in the art is contemplated as an imaging moiety of the present invention. Thus, for example, in certain embodiments of compositions of the present invention, the compositions can be applied in multimodality imaging techniques. Dual imaging and multimodality imaging are discussed in greater detail in the specification below.

In certain embodiments, the imaging moiety is a contrast media. Examples include CT contrast media, MRI contrast media, optical contrast media, ultrasound contrast media, or any other contrast media to be used in any other form of imaging modality known to those of ordinary skill in the art. Examples include diatrizoate (a CT contrast agent), a gadolinium chelate (an MRI contrast agent) and sodium fluorescein (an optical contrast media). Additional examples of contrast media are discussed in greater detail in the specification below. One of ordinary skill in the art would be familiar with the wide range of types of imaging agents that can be employed as imaging moieties in the chelators of the present invention.

T. Drug Assessment

Certain drug-based ligands can be applied in measuring the pharmacological response of a subject to a drug. A wide range of parameters can be measured in determining the response of a subject to administration of a drug. One of ordinary skill in the art would be familiar with the types of responses that can be measured. These responses depend in part upon various factors, including the particular drug that is being evaluated, the particular disease or condition for which the subject is being treated, and characteristics of the subject. Examples of drug-based ligands include carnitine, puromycin, verapamil, digoxin, prazosin, quinidine, disopyramide, theophylline, protease inhibitors, nidedipine, diltiazem, flecamide, amiodarone, sotalol, adenosine, dopamine dobutamine, inaminone, milrinone, spironolactone, prazosin, aspirin and warfarin.

U. Gene Expression Markers as Targeting Ligands

Gene expression markers refer to targeting ligands that can identify or assess a signaling pathway. Examples include glucosamine and tyrosine.

III. Synthetic Preparations Of $N_4$-Conjugates

A. Source of Reagents for the Compositions of the Present Invention

Reagents for preparation of the compositions of the present invention can be obtained from any source. A wide range of sources are known to those of ordinary skill in the art. For example, the reagents can be obtained from commercial sources such as Sigma-Aldrich Chemical Company (Milwaukee, Wis.), from chemical synthesis, or from natural sources. For example, one vendor of radionuclides is Cambridge Isotope Laboratories (Andover, Mass.). The reagents may be isolated and purified using any technique known to those of ordinary skill in the art, as described herein. The free unbound metal ions can be removed with, for example, ion-exchange resin or by adding a transchelator (e.g., glucoheptonate, gluconate, glucarate, or acetylacetonate).

B. Purification Procedures and Determinations of Purity

Persons of ordinary skill in the art will be familiar with methods of purifying compounds of the present invention. Purification of every compound of the present invention is generally possible, including the purification of intermediates as well as purification of the final products. Non-limiting examples of purification methods include gel filtration, size exclusion chromatography (also called gel filtration chromatography, gel permeation chromatography or molecular exclusion), dialysis, distillation, recrystallization, sublimation, derivatization, electrophoresis, silica gel column chromatography and high-performance liquid chromatography (HPLC), including normal-phase HPLC and reverse-phase HPLC. In certain embodiments, size exclusion chromatography and/or dialysis are specifically excluded as forms of purification of compounds of the present invention. Purification of compounds via silica gel column chromatography or HPLC, for example, offer the benefit of yielding desired compounds in very high purity, often higher than when compounds are purified via other methods.

Methods of determining the purity of compounds are well known to those of skill in the art and include, in non-limiting examples, autoradiography, mass spectroscopy, melting point determination, ultra violet analysis, calorimetric analysis, HPLC, thin-layer chromatography and nuclear magnetic resonance (NMR) analysis (including, but not limited to, $^1$H and $^{13}$C NMR). In some embodiments, a colorimetric method could be used to titrate the purity of an $N_4$ conjugate. In certain embodiments, the purity of an unknown compound may be determined by comparing it to a compound of known purity: this comparison may be in the form of a ratio whose measurement describes the purity of the unknown. Software available on varying instruments (e.g., spectrophotometers, HPLCs, NMRs) can aid one of skill in the art in making these determinations, as well as other means known to those of skill in the art.

In certain embodiments of the present invention, purification of a compound does not remove all impurities. In some embodiments, such impurities can be identified.

C. Non-limiting Exemplary Syntheses

A targeting ligand may be conjugated to an $N_4$ compound via several methods. One method is to synthesize a halide-containing (e.g., iodinated) targeting ligand. For example, the hydroxy group of a targeting ligand (e.g., a hydrophobic molecule) may be converted to a tosyl-, mesyl-, triflate, or halide (e.g., iodine) group. The reaction is typically performed in an organic solvent (e.g., dimethylformamide, DMF). Alternatively, another method to conjugate an $N_4$ compound to a targeting ligand is to synthesize a sulfonate (e.g., tosyl-, mesyl, or triflate) targeting ligand. Di-, tri-, or total substitution on the $N_4$ compound may be had by reacting one or more of these iodinated or sulfonate targeting ligands with an $N_4$ compound. For mono-, di-, or tri-substituted $N_4$ compounds, selective protection of the remaining nitrogen groups is needed. This can be accomplished using one or more amino protecting groups; such groups and their installation are well-known in the art. See, e.g., Greene and Wuts, 1999. In certain embodiments of the present invention, the final product is soluble in water after hydrochloride salt formation.

It is contemplated that virtually any targeting ligand that is known, or may be subsequently discovered, that possesses a hydroxy group or a halide, or alternatively may have a hydroxy group or halide introduced into its structure (e.g., via the addition of a sidechain, or by attaching a halide to a phenol group in the targeting ligand), may be used with the present invention. In certain embodiments, a targeting ligand may be directly conjugated to an $N_4$ compound (e.g., via a covalent bond between the targeting ligand and the $N_4$ compound), or a targeting ligand may be indirectly conjugated to an $N_4$ compound via a linker. It is envisioned that targeting ligands that have previously been conjugated to another (non-$N_4$ compound) chelator, such as EC, may be conjugated to $N_4$ compounds of the present invention and used for therapeutic purposes; in certain instances, it may be required to modify the targeting ligand (e.g., adding a side chain that contains a hydroxyl or a halide) in order to covalently bind the targeting ligand to the $N_4$ compound. For example, covalent binding of ligands with EC compounds are typically performed in water, and in certain instances it may be preferred to covalently attach a targeting ligand with an $N_4$ compound by utilizing a reaction in an organic solvent; in these instances, a targeting ligand that can be covalently bound to EC via a reaction in water may be modified (e.g., a hydrophobic linker may be added) to allow the targeting ligand to be covalently bound to an $N_4$ compound via a reaction in an organic solvent.

In general, then, the ligands for use in conjunction with the present invention will possess either a halide or a hydroxy group that are able to react with, or be modified to react with, and covalently bind to an $N_4$ compound. In certain embodiments, one targeting ligand may be conjugated to an $N_4$ compound, although conjugating at least one, at least two, at least three, or at least four or more targeting ligands is also contemplated. In certain embodiments, therefore, a conjugate of the present invention may comprise a single targeting ligand. In other embodiments, a conjugate may comprise only two targeting ligands. In further embodiments, a targeting ligand may comprise three or more targeting ligands. In any situation where a conjugate comprises two or more targeting ligands, the targeting ligands may be the same or different.

D. $N_4$ Compound-Targeting Ligand Linkages

The targeting ligands can be bound to the $N_4$ compound in any manner, including for example covalent bonds, ionic bonds and hydrogen bonds. For example, the targeting ligand may be bound to the $N_4$ compound in an amide linkage, an ester linkage, or a carbon-carbon bond linkage of any length. If two or more targeting ligands are bound to a $N_4$ compound, the modes of binding may be the same or different.

In a preferred embodiment, the present invention further provides a method of organically synthesizing an $N_4$-targeting ligand conjugate. The method includes obtaining, for example, an $N_4$ compound as described above and admixing it with a thiol protecting group in an organic medium in order to protect both free thiols, resulting in an S—S'-bis-protected-$N_4$, which is then admixed with an amino protecting group in an organic/aqueous medium in order to protect free amines. Thiol groups are more reactive than nitrogen groups; thus, thiol groups are typically protected first. As described above, persons of skill in the art will be familiar with the proper ordering of the installation of protecting groups depending on the types of functional groups present on the $N_4$ compound. This protected $N_4$ compound is then conjugated to a targeting ligand of any type described herein via any mode of conjugation described herein followed by removal of the thiol and amino protecting groups, which results in a $N_4$ compound-targeting ligand conjugate.

In certain embodiments, conjugation between an $N_4$ compound and a targeting ligand takes place in one step. In particular embodiments, the conjugation comprises a covalent attachment of a chelator to a targeting ligand, wherein the covalent attachment occurs in one step. As mentioned, such one-step procedures are preferable as they minimize time, reagents, waste and loss of product.

$N_4$ compound-targeting ligand conjugates synthesized by this method may next be chelated to a metal ion of any type described herein. Such methods of chelation are well known to those of ordinary skill in the art and are described herein. Examples of methods of chelation of metal ions to chelator-targeting ligand conjugates are described, for example, in U.S. Pat. No. 6,692,724.

Benefits of synthesizing $N_4$ compound-targeting ligand conjugates via methods of the present invention using organic synthesis include, for example, obtaining conjugates of high purity relative to conjugates obtained via aqueous synthesis, and the efficient synthesis and purification of small-molecule compounds (e.g., 1000 g/mol or less). These benefits allow for conjugates that can be utilized in imaging, diagnostic, and/or therapeutic experiments and/or clinical trials.

For example, the targeting ligand may be bound to the chelator in an amide linkage, an ester linkage, or a carbon-carbon bond linkage of any length. If two or more targeting ligands are bound to a chelator, the modes of binding may be the same or different. In other embodiments, the linkage comprises a linker. For example, if the targeting ligand is not water soluble, a linker which will increase the solubility of the ligand may be used. Linkers may attach to, for example, an aliphatic or aromatic alcohol, amine, peptide, or to a carboxylic acid. Non-limiting examples of such linkers include peptides, glutamic acid, aspartic acid, bromoethylacetate, ethylene diamine, lysine and any combination of one or more of these groups. See also Table 3. One of ordinary skill in the art would be familiar with the chemistry of these agents, and methods to conjugate these agents as ligands to the chelators of the claimed invention.

TABLE 3

Linkers

| Drug Functional Group | Linker | Example |
|---|---|---|
| Aliphatic or phenolic-OH | EC-poly(glutamic acid) (MW 750-15,000) or EC poly(aspartic acid) (MW 2000-15,000) or bromo ethylacetate or EC-glutamic acid or EC-aspartic acid | estradiol, topotecan, paclitaxel, raloxifen etoposide |
| Aliphatic or aromatic-NH$_2$ or peptide | EC-poly(glutamic acid) (MW 750-15,000) or EC-poly(aspartic acid) (MW 2000-15,000) or EC-glutamic acid (mono- or diester) or EC-aspartic acid | doxorubicin, mitomycin C, endostatin, annexin V, LHRH, octreotide, VIP |
| Carboxylic acid or peptide | Ethylene diamine, lysine | methotrexate, folic acid |

E. Metal Ion Labeling of $N_4$ Conjugates

Certain embodiments of the present invention pertain to compositions that will function to chelate one or more metal ions. Along with the $N_4$ compounds, the targeting ligands of the present invention may also participate in chelating one or more metal ions in an $N_4$ conjugate. A "metal ion" is defined herein to refer to a metal ion that is capable of forming a bond, such as a non-covalent bond, with one or more atoms or molecules. The other atom(s) or molecule(s) may be negatively charged. The metal ion may be radioactive or non-radioactive (cold).

Any metal ion known to those of ordinary skill in the art is contemplated for inclusion in the compositions of the present invention. One of ordinary skill in the art would be familiar with the metal ions and their application(s). In some embodiments, the metal ion may be selected from the group consisting of Tc-99m, Cu-60, Cu-61, Cu-62, Cu-67, In-111, Tl-201, Ga-67, Ga-68, As-72, Re-186, Re-187, Re-188, Ho-166, Y-90, Sm-153, Sr-89, Gd-157, Bi-212, Bi-213, Fe-56, Mn-55, Lu-177, an iron ion, an arsenic ion, a selenium ion, a thallium ion, a manganese ion, a cobalt ion, a platinum ion, a rhenium ion, a calcium ion and a rhodium ion. In certain particular embodiments, an $N_4$ conjugate is chelated to $^{187}$Re.

As mentioned, the metal ion may be radioactive or non-radioactive. To facilitate certain embodiments involving, for example, imaging or the use of an $N_4$ conjugate as a chemotherapeutic, a radioactive metal ion (that is, a radioisotope) may be chelated to the $N_4$ conjugate. In certain embodiments, the radioactive metal ion is selected from the group consisting of $^{99m}$Tc, $^{188}$Re, $^{186}$Re, $^{153}$Sm, $^{166}$Ho, $^{90}$Y, $^{89}$Sr, $^{67}$Ga, $^{68}$Ga, $^{111}$In, $^{148}$Gd $^{55}$Fe, $^{225}$Ac, $^{212}$Bi, $^{211}$At, $^{45}$Ti, $^{60}$Cu, $^{61}$Cu, $^{67}$Cu, $^{64}$Cu and $^{62}$Cu. In certain embodiments, the non-radioactive metal ion is selected from the group consisting of Cu-62, As-72, Re-187, Gd-157, Bi-213, Fe-56, Mn-55, an iron ion, a manganese ion, a cobalt ion, a platinum ion and a rhodium ion.

Generally, it is believed that virtually any α-, β-emitter, γ-emitter, or β,γ-emitter may be used in conjunction with the invention. Certain α-emitters of the present invention include bismuth-212, bismuth-213, astatine-211, and radium-223. Certain β,γ-emitters of the present invention include $^{166}$Ho, $^{188}$Re, $^{186}$Re, $^{153}$Sm, and $^{89}$Sr. Certain β-emitters of the present invention include $^{90}$Y and $^{225}$Ac. Certain γ-emitters of the present invention include $^{67}$Ga, 68Ga, $^{64}$Cu, $^{62}$Cu and $^{111}$In. It is also envisioned that para-magnetic substances, such as Gd, Mn, Cu, or Fe can be chelated with $N_4$ conjugates for use in conjunction with the present invention.

In radioimaging, the radiolabel is typically a gamma-radiation emitting radionuclide and the radiotracer is typically located using a gamma-radiation detecting camera (this process is often referred to as gamma scintigraphy). The imaged site is detectable because the radiotracer is chosen either to localize at a pathological site (termed positive contrast) or, alternatively, the radiotracer is chosen specifically not to localize at such pathological sites (termed negative contrast).

A variety of radionuclides are known to be useful for radioimaging and radioimmunotherapy, including $^{67}$Ga/$^{68}$Ga, $^{99m}$Tc, $^{111}$In, $^{123}$I, $^{125}$I, $^{169}$Yb or $^{186}$Re/$^{188}$Re. Due to better imaging characteristics and lower price, attempts have been made to replace or provide an alternative to $^{123}$I, $^{131}$I, $^{67}$Ga and $^{111}$In labeled compounds with corresponding $^{99m}$Tc labeled compounds when possible. Due to favorable physical characteristics as well as extremely low price ($0.21/mCi), $^{99m}$Tc is often preferred to label radiopharmaceuticals. However, $^{99m}$Tc may not always be an adequate substitute. For example, although it has been reported that diethylenetriamine (DTPA)-drug conjugate could be labeled with $^{99m}$Tc effectively (Mathias et al., 1997), the DTPA moiety does not chelate with $^{99m}$Tc as stably as with $^{111}$In (Goldsmith, 1997).

A number of factors must be considered for optimal radioimaging in humans. To maximize the efficiency of detection, a radionuclide that emits gamma energy in the 100 to 200 keV range may be chosen. To minimize the absorbed radiation dose to the patient, the physical half-life of the radionuclide should be as short as the imaging procedure will allow. To allow for examinations to be performed on any day and at any time of the day, it is advantageous to have a source of the radionuclide always available at the clinical site. $^{99m}$Tc is often a preferred radionuclide because it emits gamma radiation at 140 keV, it has a physical half-life of 6 hours, and it is readily available on-site using a molybdenum-99/technetium-99m generator.

In certain embodiments, an $N_4$ conjugate may be labeled (e.g., chelated) with $^{68}$Ga for PET imaging or $^{188}$Re (a beta and gamma emitter) for internal radionuclide therapy. As stated above, $^{99m}$Tc, $^{68}$Ga and $^{188}$Re may be obtained from generators which are accessible and affordable.

Technetium has a number of oxidation states: +1, +2, +4, +5, +6 and +7. When it is in the +1 oxidation state, it is called Tc MIBI. Tc MIBI is typically produced with a heat reaction (Seabold et al. 1999). For certain embodiments of the present invention involving chelating Tc to an $N_4$ compound or an $N_4$ conjugate, Tc is in the +4 oxidation state. This oxidation state is ideal for forming the chelate with an $N_4$ compound or an $N_4$ conjugate. Thus, in forming a complex of radioactive technetium with the drug conjugates of the invention, the technetium complex (e.g., a salt of $^{99m}$Tc pertechnetate) is typically reacted with the drug conjugates of the invention in the presence of a reducing agent.

One type of reducing agent for use in the present invention is a stannous ion in the form of stannous chloride ($SnCl_2$) to reduce the Tc to its +4 oxidation state. However, it is contemplated that other reducing agents, such as dithionate ion or ferrous ion may be useful in conjunction with the present invention. It is also contemplated that the reducing agent may be a solid phase reducing agent. The amount of reducing agent can be important as it is necessary to avoid the formation of a colloid. In certain embodiments, about 10 to about 100 μg $SnCl_2$ per about 100 to about 300 mCi of Tc pertechnetate may be used, or in further embodiments, about 0.1 mg $SnCl_2$ per about 200 mCi of Tc pertechnetate and about 2 ml saline may be used.

In addition to imaging tumors with $N_4$ conjugates labeled with radionuclides, it is envisioned that these compounds may also be used for imaging of tissue related to other diseases, as well as diagnostics related to cancer and other diseases. For example, it is contemplated that $N_4$ conjugates labeled with radionuclides of the invention may be useful to image not only tumors, but also other tissue-specific conditions, such as infection, hypoxic tissue (stroke), myocardial infarction, apoptotic cells, Alzheimer's disease and endometriosis. An advantage of imaging using an $N_4$ conjugate that comprises a radiolabeled $N_4$ compound conjugated to a tissue targeting ligand is that the specific binding properties of the tissue targeting ligand concentrates the radioactive signal over the area of interest.

In certain embodiments, the $N_4$ conjugate may be chelated to a non-radioactive metal ion. When chelated with non-radioactive metals (e.g., copper, cobalt, platinum, iron, arsenic, rhenium (e.g., $^{187}$Re), germanium), the cold (non-radioactive) $N_4$ conjugate may be used as a metallic chemotherapeutic agent.

One aspect of the uniqueness of this technology is to use the same PET sulfonate precursors or SPECT iodinated agents to react with an $N_4$ compound which is a chelator. The end product may then be chelated with metals which is easier, more accessible and more affordable.

F. Protecting Groups

When a chemical reaction is to be carried out selectively at one reactive site in a multifunctional compound, other reactive sites often must be temporarily blocked. A "protecting group," as used herein, is defined as a group used for the purpose of this temporary blockage. Thus, the function of a protecting group is to protect one or more functional groups (e.g., —$NH_2$, —SH, —COOH) during subsequent reactions which would not proceed well, either because the free (in other words, unprotected) functional group would react and be functionalized in a way that is inconsistent with its need to be free for subsequent reactions, or the free functional group would interfere in the reaction. Persons of skill in the art recognize that the use of protecting groups is typical in synthetic organic chemistry.

During the synthesis of the compounds of the present invention, various functional groups must be protected using protecting agents at various stages of the synthesis. A "protecting agent" is used to install the protecting group. Thus, in a typical procedure, a protecting agent is admixed with a compound featuring a functional group that is to be protected, and the protecting agent forms a covalent bond with that functional group. In this manner, the functional group is "protected" by a protecting group (and effectively rendered unreactive) by the covalent bond that formed with the protecting agent. Multiple functional groups can be protected in one or more steps using properly selected protecting agents. Such proper selection is understood by those of skill in the art. Such selection is often based upon the varying reactivity of the functional groups to be protected: thus, more reactive groups (such as sulfur/thiol) are typically protected before less reactive groups (such as amine) are protected.

There are a number of methods well known to those skilled in the art for accomplishing such a step. For protecting agents, their reactivity, installation and use, see, e.g., Greene and Wuts, 1999, herein incorporated by reference in its entirety. The same protecting group may be used to protect one or more of the same or different functional group(s). Non-limiting examples of protecting group installation are described below.

Use of the phrase "protected hydroxy" or "protected amine" and the like does not mean that every functional group available to be protected is protected. Similarly, a "protected chelator," as used herein, does not imply that every functional group of the chelator is protected.

Compounds of the present invention, including compounds used and made during the practice of the method of the present invention, are contemplated both in protected and unprotected (or "free") form. Persons of ordinary skill in the art will understand that functional groups necessary for a desired transformation should be unprotected.

When a protecting group is no longer needed, it is removed by methods well known to those skilled in the art. For deprotecting agents and their use, see, e.g., Greene and Wuts, 1999. Agents used to remove the protecting group are typically called deprotecting agents. Protecting groups are typically readily removable (as is known to those skilled in the art) by methods employing deprotecting agents that are well known to those skilled in the art. For instance, acetate ester and carbamate protecting groups may be easily removed using mild acidic or basic conditions, yet benzyl and benzoyl ester protecting groups need much stronger acidic or basic conditions. It is well known that certain deprotecting agents remove some protective groups and not others, while other deprotecting agents remove several types of protecting groups from several types of functional groups. For instance, Birch reduction reactions using liquid ammonia and sodium (as described below) deprotect benzyl groups from thiols (or sulfur, more particularly) or carbamate groups from nitrogen, but not acetate groups from oxygen. Thus, a first deprotecting agent may be used to remove one type of protecting group, followed by the use of a second deprotecting agent to remove a second type of protecting group, and so on.

Persons of ordinary skill in the art will be familiar with the proper ordering of protective group removal using deprotecting agents. See e.g., Greene and Wuts, 1999. Non-limiting examples of protecting group removal are discussed below.

Amine protecting groups are well known to those skilled in the art. See, for example, Greene and Wuts, 1999, Chapter 7.

These protecting groups can be installed via protecting agents well known to those of skill in the art. Removal of these groups is also well known to those of skill in the art.

In some embodiments, the amine protecting group may be selected from the group consisting of t-butoxycarbonyl, benzyloxycarbonyl, formyl, trityl, acetyl, trichloroacetyl, dichloroacetyl, chloroacetyl, trifluoroacetyl, difluoroacetyl, fluoroacetyl, benzyl chloroformate, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluoyl)prop-2-yloxycarbonyl, cyclopentanyloxycarbonyl, 1-methylcyclopentanyloxycarbonyl, cyclohexanyloxycarbonyl, 1-methylcyclohexanyloxycabonyl, 2-methylcyclohexanyloxycarbonyl, 2-(4-toluoylsulfonyl)ethoxycarbonyl, 2-(methylsulfonyl)ethoxycarbonyl, 2-(triphenylphosphino) ethoxycarbonyl, fluorenylmethoxycarbonyl, 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and 9-fluorenylmethyl carbonate.

In some embodiments, the protecting agent for amine protection is selected from the group consisting of benzylchloroformate, p-nitro-chlorobenzylformate, ethylchloroformate, di-tert-butyl-dicarbonate, triphenylmethyl chloride and methoxytriphenylmethyl chloride. In a preferred embodiment, the protecting group is benzyloxycarbonyl, installed by the protecting agent benzyloxychloroformate.

Thiol protecting groups are well known to those skilled in the art. See, e.g., Greene and Wuts, 1999, Chapter 6. These protecting groups can be installed via protecting agents well known to those of skill in the art. Removal of these groups is also well known to those of skill in the art.

In some embodiments, a thiol protecting group may be selected from the group consisting of acetamidomethyl, benzamidomethyl, 1-ethoxyethyl, benzoyl, triphenylmethyl, t-butyl, benzyl, adamantyl, cyanoethyl, acetyl and trifluoroacetyl.

In some embodiments, the protecting agent for thiol protection is selected from the group consisting of an alkyl halide, a benzyl halide, a benzoyl halide, a sulfonyl halide, a triphenylmethyl halide, a methoxytriphenylmethyl halide and cysteine. Non-limiting examples of these protecting agents include ethyl halides, propyl halides and acetyl halides. Halides may comprise chloro, bromo or iodo, for example. In a preferred embodiment, the protecting group is benzyl, installed by the protecting agent benzyl chloride.

Hydroxy (or alcohol) protecting groups are well known to those skilled in the art. See, e.g., Greene and Wuts, 1999, Chapter 2. These protecting groups can be installed via protecting agents well known to those of skill in the art. Removal of these groups is also well known to those of skill in the art.

A suitable hydroxy protecting group may be selected from the group consisting of esters or ethers. Esters such as acetate, benzoyl, tert-butylcarbonyl and trifluoroacetyl groups are removable by acidic or basic conditions. Ethers such as methoxy, ethoxy and tri-benzylmethyl are removable by stronger acidic or basic conditions. A preferred protecting group is an acetate ester.

Carbonyl protecting groups are well known to those skilled in the art. See, e.g., Greene and Wuts, 1999, Chapter 4. These protecting groups can be installed via protecting agents well known to those of skill in the art. Removal of these groups is also well known to those of skill in the art.

In some embodiments, a carbonyl protecting group may be selected from the group consisting of dimethylacetal, dimethylketal, diisopropylacetal, diisopropylketal, enamines and enol ethers.

Carboxylic acid protecting groups are well known to those skilled in the art. See, e.g., Greene and Wuts, 1999, Chapter 5. Removal of these groups is also well known to those of skill in the art.

A suitable carboxylic acid protecting group may be selected from the group consisting of amides or esters, for example. Amides such as sulfonamide, para-nitroaniline, benzylamide and benzolyamide may be hydrolyzed in acidic conditions. Esters such as methyl ester, ethyl ester and benzyl ester maybe hydrolyzed by acidic or basic conditions. A preferred protecting group is an amide.

IV. Exemplary Uses for $N_4$ Conjugates

The $N_4$ conjugates of the present invention may be used for any application known to those of skill in the art. For example, $N_4$ conjugates may be used to target tumors (e.g., cancerous, precancerous, benign), tumor angiogenesis, hypoxia, apoptosis defects, disease receptors (e.g., cell receptors that are indicative of cancer), disease functional pathways (e.g., a metabolic pathway that has been altered by a disease state) and disease cell cycles. Additionally, $N_4$ conjugates may be used for the assessment of a pharmaceutical agent's effectiveness on these biochemical processes.

$N_4$ conjugates may also be used as a diagnostic tool and/or for predicting responses to certain kinds of treatment. For example, an $N_4$ conjugate that comprises tamoxifen (an estrogen receptor targeting ligand) may be used to image cancerous tumors; in this example, the imaging may provide important information about the disease such as to what degree the cancerous cells express the estrogen receptor which can be used to predict how the disease will respond to treatments that target cells expressing the estrogen receptor (e.g., when it is identified that cancerous tumors selectively express high levels of estrogen receptor, this information indicates that the cancerous cells will likely respond to therapeutic doses of anti-cancer agents that target cells expressing the estrogen receptor). This approach is referred to as "image guided therapy."

An advantage of conjugating an $N_4$ compound with a tissue targeting ligand is that the specific binding properties of the tissue targeting ligand can concentrate the radioactive signal over the area of interest. It is therefore envisioned that $N_4$ conjugates used for imaging and/or therapy may comprise, in certain embodiments, an $N_4$ compound conjugated to a targeting ligand designed for targeting cancerous tumors, precancerous tumors, disease receptors, hypoxic tissues (hypoxia), apoptosis pathways, disease cell cycles, and/or disease functional pathways.

The $N_4$ conjugates of the invention may also be used for prognostic purposes. It is envisioned that $N_4$ conjugates may be administered to a patient having a tumor. It is envisioned that the use of a radiolabelled $N_4$ compound as a labeling strategy can be effective with ligands designed for targeting disease receptors, hypoxia markers, apoptosis defects, disease cell cycles, disease functional pathways, and assessment of pharmaceutical agents effectiveness of these or other biochemical processes. Imaging may be performed, for example, to determine the effectiveness of the $N_4$ conjugate against a patient's specific problem relating to disease receptors, hypoxia markers, apoptosis defects, disease cell cycles, disease functional pathways, and assessment of pharmaceutical agent's effectiveness on these biochemical processes. Using this methodology, physicians can quickly determine which $N_4$ conjugate will be most effective for the patient and design the corresponding therapy or mode of treatment. This methodology possesses significant advantages over methods involving first choosing a drug and administering a round of chemotherapy, which may involve months of the patient's time at a substantial physical and financial cost before the effectiveness of the cancer chemotherapeutic agent can be determined.

The present invention may also be used to monitor the progress of former patients who have successfully undergone chemotherapy or radiation treatment to determine if cancer has remained in remission or is metastasizing. People with a history of cancer in their family or who have been diagnosed with a gene(s) associated with cancer may undergo monitoring by health professionals using the methodology of the current invention. The methods and pharmaceutical agents of the current invention may also be used by a health professional to monitor if cancer has started to develop in a person with cancer risk factors, such as environmental exposure to carcinogens.

Certain drug-based targeting ligands that may be conjugated to an $N_4$ compound of the present invention can be used to measure the pharmacological response of a subject to a drug. A wide range of parameters can be measured in determining the response of a subject to administration of a drug. One of ordinary skill in the art would be familiar with the types of responses that can be measured. These responses depend in part upon various factors, including the particular drug that is being evaluated, the particular disease or condition for which the subject is being treated, and characteristics of the subject. In certain embodiments, radiolabelled agents can be applied in measuring drug assessment.

A. Hyperproliferative Disease

Certain aspects of the present invention pertain to compositions wherein a therapeutic moiety is conjugated to an $N_4$ compound. When a metal ion is chelated to an an $N_4$ compound or to both an $N_4$ compound and its conjugated targeting ligand, the composition of the present invention may, in certain embodiments, be useful in dual imaging and therapy. In certain particular embodiments, the therapeutic moiety is a moiety that is an agent known or suspected to be of benefit in the treatment or prevention of hyperproliferative disease in a subject. The subject may be an animal, such as a mammal. In certain particular embodiments, the subject is a human.

In other embodiments of the present invention, the metal ion is a therapeutic metal ion (e.g., Re-188, Re-187, Re-186, Ho-166, Y-90, Sr-89, and Sm-153), and the $N_4$ conjugate is an agent that is a therapeutic agent (rather than an imaging agent) that can be applied in the treatment or prevention of a hyperproliferative disease.

A hyperproliferative disease is herein defined as any disease associated with abnormal cell growth or abnormal cell turnover. For example, the hyperproliferative disease may be cancer. The term "cancer" as used herein is defined as an uncontrolled and progressive growth of cells in a tissue. A skilled artisan is aware other synonymous terms exist, such as neoplasm or malignancy or tumor. Any type of cancer is contemplated for treatment by the methods of the present invention. For example, the cancer may be breast cancer, lung cancer, ovarian cancer, brain cancer, liver cancer, cervical cancer, colon cancer, renal cancer, skin cancer, head and neck cancer, bone cancer, esophageal cancer, bladder cancer, uterine cancer, stomach cancer, pancreatic cancer, testicular cancer, lymphoma, or leukemia. In other embodiments of the present invention, the cancer is metastatic cancer.

B. Dual Chemotherapy and Radiation Therapy ("Radiochemotherapy")

In certain embodiments of the present invention, the compositions of the present invention are suitable for dual chemotherapy and radiation therapy (radiochemotherapy). For example, an $N_4$ compound or conjugate as set forth herein may be chelated to a metal ion that is a therapeutic metal ion, as well as a targeting ligand that is a therapeutic moiety (such as an anti-cancer moiety). As another example, a therapeutic metal ion may be chelated to both an $N_4$ compound and its targeting ligand conjugate.

For example, the metal ion may be a beta-emitter. As herein defined, a beta emitter is any agent that emits beta energy of any range. Examples of beta emitters include Re-188, Re-187, Re-186, Ho-166, Y-90, and Sn-153. One of ordinary skill in the art would be familiar with these agents for use in the treatment of hyperproliferative disease, such as cancer.

One of ordinary skill in the art would also be familiar with the design of chemotherapeutic protocols and radiation therapy protocols that can applied in the administration of the compounds of the present invention. As set forth below, these agents may be used in combination with other therapeutic modalities directed at treatment of a hyperproliferative disease, such as cancer. Furthermore, one of ordinary skill in the art would be familiar with selecting an appropriate dose for administration to the subject. The protocol may involve a single dose, or multiple doses. The patient would be monitored for toxicity and response to treatment using protocols familiar to those of ordinary skill in the art.

C. Methods of Diagnosis, Treatment, or Imaging in a Subject with Known or Suspected Heart Disease Embodiments of the present invention also generally pertain to methods of diagnosis, treatment, or imaging in a subject with known or suspected heart disease. The subject can be any subject, such as a mammal or avian species. The mammal, for example, may be a dog, cat, rat, mouse, or human. In preferred embodiments, the subject is a human with known or suspected cardiovascular disease.

The cardiovascular disease can be any disease of the heart or of a blood vessel. The blood vessel may be a coronary vessel, or may be a vessel other than a coronary vessel. The vessel may be an artery, vein, arteriole, venule, or capillary.

Examples of cardiovascular diseases include diseases of the heart, such as myocardial infarction, myocardial ischemia, angina pectoris, congestive heart failure, cardiomyopathy (congenital or acquired), arrhythmia, valvular heart disease, noncardiac circulatory congestion, systolic heart failure, heart failure with normal systolic function, and right-sided heart failure. In particular embodiments, the subject is known or suspected to have myocardial ischemia. In particular embodiments, the cardiovascular disease is a myocardial infarction, myocardial ischemia, or angina pectoris and the method further comprises imaging the heart of the subject with the use of SPECT, PET, SPECT/CT, MRI, SPECT/MRI, PET/CT, PET/MRI, or other nuclear medicine-based imaging. Any part of the heart may be imaged, such as the myocardium, areas of ischemia, the coronary arteries, and so forth.

The subject, for example, may be a patient who presents to a clinic with signs or symptoms suggestive of myocardial ischemia or myocardial infarction. Imaging of the heart of the subject to diagnose disease may involve administering to the subject a pharmaceutically effective amount of a metal ion labeled chelator-targeting ligand conjugate synthesized using any of the methods set forth herein. Imaging can be performed using any imaging modality known to those of ordinary skill in the art. In particular embodiments, imaging involves use radionuclide-based imaging technology, such as PET or SPECT. In particular embodiments, the metal ion-labeled radionuclide-targeting ligand conjugate is 99m-Tc-EC-glucosamine. Glucosamine is actively taken up by viable myocardial tissue. Areas of ischemic myocardium would take up less or no conjugate. Severity of ischemia can be visually assessed or graded depending on magnitude of the signal that is measured using any method known to those of ordinary skill in the art. In some embodiments, imaging using any of the conjugates set forth herein is performed before, during, or after imaging of the heart using a second imaging modality. For example, the second imaging modality may be thallium scinigraphy.

Myocardial Perfusion SPECT (MPS) consists of a combination of a stress modality (exercise or pharmacologic) with rest and stress administration and imaging of radiopharmaceuticals. Thallium has excellent physiologic properties for myocardial perfusion imaging. Being highly extracted during the first pass through the coronary circulation, a linear relationship between blood flow to viable myocardium and thallium uptake has been shown during exercise; however, at very high levels of flow, a "roll-off" in uptake occurs. As an unbound potassium analogue, thallium redistributes over time. Its initial distribution is proportional to regional myocardial perfusion and at equilibrium, the distribution of thallium is proportional to the regional potassium pool, reflecting viable myocardium. The mechanisms of thallium redistribution are differential washout rates between hypoperfused but viable myocardium and normal zones and wash-in to initially hypoperfused zones. The washout rate of thallium is the concentration gradient between the myocardial cell and the blood. There is slower blood clearance of thallium following resting or low-level exercise injection. Diffuse slow washout rates, mimicking diffuse ischemia, may be observed in normal patients who do not achieve adequate levels of stress. Hyperinsulinemic states slow redistribution, leading to an underestimation of viable myocardium; thus fasting is recommended prior to and for 4 hrs following thallium injection. Thus, if an $N_4$ conjugate is used as an viable agent in combination with thallium, the conjugate will target the precise area of interest (the viable area). See Angello et al., 1987; Gutman et al., 1983; Pohost et al., 1977.

Imaging using any of the metal ion-labeled chelator-targeting ligand conjugates of the present invention may also be performed in conjunction with other diagnostic methods, such as measurement of cardiac isozymes, or cardiac catheterization. The imaging may be performed at various intervals following onset of symptoms, or can be performed to assess for changes in myocardial perfusion over time.

In certain embodiments, the methods involve methods of dual imaging and delivery of a therapeutic agent to the heart. For example, the therapeutic agent can be administered as a targeting ligand conjugated to a chelator. Examples of such therapeutic agents include those cardiovascular drugs set forth elsewhere in this specification.

V. Examples Of Imaging Modalities

A. Gamma Camera Imaging

A variety of nuclear medicine techniques for imaging are known to those of ordinary skill in the art. Any of these techniques can be applied in the context of the imaging methods of the present invention to measure a signal from the reporter. For example, gamma camera imaging is contemplated as a method of imaging that can be utilized for measuring a signal derived from the reporter. One of ordinary skill in the art would be familiar with techniques for application of gamma camera imaging (see, e.g., Kundra et al., 2002, herein specifically incorporated by reference). In one embodiment, measuring a signal can involve use of gamma-camera imaging of a 111-In-octreotide-SSRT2A reporter system.

B. PET and SPECT

Radionuclide imaging modalities (positron emission tomography, (PET); single photon emission computed tomography (SPECT)) are diagnostic cross-sectional imaging techniques that map the location and concentration of radionuclide-labeled radiotracers. Although CT and MRI provide considerable anatomic information about the location and the extent of tumors, these imaging modalities cannot adequately differentiate invasive lesions from edema, radiation necrosis, grading or gliosis. PET and SPECT can be used to localize and characterize tumors by measuring metabolic activity.

PET and SPECT provide information pertaining to information at the cellular level, such as cellular viability. In PET, a patient ingests or is injected with a slightly radioactive substance that emits positrons, which can be monitored as the substance moves through the body. In one common application, for instance, patients are given glucose with positron emitters attached, and their brains are monitored as they perform various tasks. Since the brain uses glucose as it works, a PET image shows where brain activity is high.

Closely related to PET is single-photon emission computed tomography, or SPECT. The major difference between the two is that instead of a positron-emitting substance, SPECT uses a radioactive tracer that emits low-energy photons. SPECT is valuable for diagnosing coronary artery disease, and already some 2.5 million SPECT heart studies are done in the United States each year.

PET radiopharmaceuticals for imaging are commonly labeled with positron-emitters such as $^{11}C$, $^{13}N$, $^{15}O$, $^{18}F$, $^{82}Rb$, $^{62}Cu$ and $^{68}Ga$. SPECT radiopharmaceuticals are commonly labeled with positron emitters such as $^{99m}Tc$, $^{201}Tl$ and $^{67}Ga$. Regarding brain imaging, PET and SPECT radiopharmaceuticals are classified according to blood-brain-barrier permeability (BBB), cerebral perfusion and metabolism receptor-binding, and antigen-antibody binding (Saha et al., 1994). The blood-brain-barrier SPECT agents, such as $^{99m}TcO4$-DTPA, $^{201}Tl$, and [$^{67}Ga$]citrate are excluded by normal brain cells, but enter into tumor cells because of altered BBB. SPECT perfusion agents such as [$^{123}I$]IMP, [$^{99m}Tc$]HMPAO, [$^{99m}Tc$]ECD are lipophilic agents, and therefore diffuse into the normal brain. Important receptor-binding SPECT radiopharmaceuticals include [$^{123}I$]QNE, [$^{123}I$]IBZM and [$^{123}I$]iomazenil. These tracers bind to specific receptors, and are of importance in the evaluation of receptor-related diseases.

C. Computerized Tomography (CT)

Computerized tomography (CT) is contemplated as an imaging modality in the context of the present invention. By taking a series of X-rays, sometimes more than a thousand, from various angles and then combining them with a computer, CT made it possible to build up a three-dimensional image of any part of the body. A computer is programmed to display two-dimensional slices from any angle and at any depth.

In CT, intravenous injection of a radiopaque contrast agent can assist in the identification and delineation of soft tissue masses when initial CT scans are not diagnostic. Similarly, contrast agents aid in assessing the vascularity of a soft tissue or bone lesion. For example, the use of contrast agents may aid the delineation of the relationship of a tumor and adjacent vascular structures.

CT contrast agents include, for example, iodinated contrast media. Examples of these agents include iothalamate, iohexyl, diatrizoate, iopamidol, ethiodol and iopanoate. Gadolinium agents have also been reported to be of use as a CT contrast agent (see, e.g., Henson et al., 2004). For example, gadopentate agents has been used as a CT contrast agent (discussed in Strunk and Schild, 2004).

D. Magnetic Resonance Imaging (MRI)

Magnetic resonance imaging (MRI) is an imaging modality that is newer than CT that uses a high-strength magnet and radio-frequency signals to produce images. The most abundant molecular species in biological tissues is water. It is the quantum mechanical "spin" of the water proton nuclei that ultimately gives rise to the signal in imaging experiments. In MRI, the sample to be imaged is placed in a strong static magnetic field (1-12 Tesla) and the spins are excited with a pulse of radio frequency (RF) radiation to produce a net magnetization in the sample. Various magnetic field gradients and other RF pulses then act on the spins to code spatial information into the recorded signals. By collecting and analyzing these signals, it is possible to compute a three-dimensional image which, like a CT image, is normally displayed in two-dimensional slices.

Contrast agents used in MR imaging differ from those used in other imaging techniques. Their purpose is to aid in distinguishing between tissue components with identical signal characteristics and to shorten the relaxation times (which will produce a stronger signal on T1-weighted spin-echo MR images and a less intense signal on T2-weighted images). Examples of MRI contrast agents include gadolinium chelates, manganese chelates, chromium chelates, and iron particles.

Both CT and MRI provide anatomical information that aid in distinguishing tissue boundaries and vascular structure. Compared to CT, the disadvantages of MRI include lower patient tolerance, contraindications in pacemakers and certain other implanted metallic devices, and artifacts related to multiple causes, not the least of which is motion (Alberico et al., 2004). CT, on the other hand, is fast, well tolerated, and readily available but has lower contrast resolution than MRI and requires iodinated contrast and ionizing radiation (Alberico et al., 2004). A disadvantage of both CT and MRI is that neither imaging modality provides functional information at the cellular level. For example, neither modality provides information regarding cellular viability.

E. Optical Imaging

Optical imaging is another imaging modality that has gained widespread acceptance in particular areas of medicine. Examples include optical labelling of cellular components, and angiography such as fluorescein angiography and indocyanine green angiography. Examples of optical imaging agents include, for example, fluorescein, a fluorescein derivative, indocyanine green, Oregon green, a derivative of Oregon green derivative, rhodamine green, a derivative of rhodamine green, an eosin, an erythrosin, Texas red, a derivative of Texas red, malachite green, nanogold sulfosuccinimidyl ester, cascade blue, a coumarin derivative, a naphthalene, a pyridyloxazole derivative, cascade yellow dye, or dapoxyl dye.

F. Ultrasound

Another biomedical imaging modality that has gained widespread acceptance is ultrasound. Ultrasound imaging has been used noninvasively to provide realtime cross-sectional and even three-dimensional images of soft tissue structures and blood flow information in the body. High-frequency sound waves and a computer to create images of blood vessels, tissues and organs.

Ultrasound imaging of blood flow can be limited by a number of factors such as size and depth of the blood vessel. Ultrasonic contrast agents, a relatively recent development, include perfluorine and perfluorine analogs, which are designed to overcome these limitations by helping to enhance grey-scale images and Doppler signals.

G. Procedure for Dual Imaging

Certain embodiments of the present invention pertain to methods of imaging a site within a subject using two imaging modalities that involve measuring a first signal and a second signal from the imaging moiety-chelator-metal ion complex. The first signal is derived from the metal ion and the second signal is derived from the imaging moiety. As set forth above, any imaging modality known to those of ordinary skill in the art can be applied in these embodiments of the present imaging methods.

The imaging modalities are performed at any time during or after administration of the composition comprising the diagnostically effective amount of the composition of the present invention. For example, the imaging studies may be performed during administration of the dual imaging composition of the present invention, or at any time thereafter. In some embodiments, the first imaging modality is performed beginning concurrently with the administration of the dual imaging agent, or about 1 sec, 1 hour, 1 day, or any longer period of time following administration of the dual imaging agent, or at any time in between any of these stated times.

The second imaging modality may be performed concurrently with the first imaging modality, or at any time following the first imaging modality. For example, the second imaging modality may be performed about 1 sec, about 1 hour, about 1 day, or any longer period of time following completion of the first imaging modality, or at any time in between any of these stated times. In certain embodiments of the present invention, the first and second imaging modalities are performed concurrently such that they begin at the same time following administration of the agent. One of ordinary skill in the art would be familiar with performance of the various imaging modalities contemplated by the present invention.

In some embodiments of the present methods of dual imaging, the same imaging device is used to perform a first imaging modality and a second imaging modality. In other embodiments, a different imaging device is used to perform the second imaging modality. One of ordinary skill in the art would be familiar with the imaging devices that are available for performance of a first imaging modality and a second imaging modality, and the skilled artisan would be familiar with use of these devices to generate images.

H. Kits

Certain embodiments of the present invention are generally concerned with kits for preparing an imaging or diagnostic agent. For example, in some embodiments the kit includes one or more sealed containers that contain a predetermined quantity of an $N_4$ conjugate. In some embodiments, the kit further includes a sealed container containing a metal ion. For example, the metal ion may be a radionuclide.

A kit of the present invention may include a sealed vial containing a predetermined quantity of an $N_4$ conjugate of the present invention and a sufficient amount of reducing agent to label the compound with a metal ion. In some embodiments of the present invention, the kit includes a metal ion that is a radionuclide. In certain further embodiments, the radionuclide is $^{99m}Tc$.

The kit may also contain conventional pharmaceutical adjunct materials such as, for example, pharmaceutically acceptable salts to adjust the osmotic pressure, buffers, preservatives and the like.

In certain embodiments, an antioxidant is included in the composition to prevent oxidation of the chelator moiety. In certain embodiments, the antioxidant is vitamin C (ascorbic acid). However, it is contemplated that any other antioxidant known to those of ordinary skill in the art, such as tocopherol, pyridoxine, thiamine, or rutin, may also be used. The components of the kit may be in liquid, frozen, or dry form. In a preferred embodiment, kit components are provided in lyophilized form.

The cold (that is, non-radioactivity containing) instant kit is considered to be a commercial product. The cold instant kit could serve a radiodiagnostic purpose by adding pertechnetate to vial with API and bulking agents (agents which have not been tested yet). The technology is known as the "shake and shoot" method to those of skill in the art. The preparation time of radiopharmaceuticals would be less than 15 min. The same kit could also encompass an $N_4$ conjugate that could be chelated with different metals for different imaging applications. For instance, copper-61 (3.3 hrs half life) for PET; gadolinium for MRI. The cold kit itself could be used for prodrug purposes to treat disease. For example, the kit could be applied in tissue-specific targeted imaging and therapy. The kit could also encompass an $N_4$ compound that could be conjugated to different targeting ligands, which may or may not also be provided in the kit, and optionally chelated to a metal ion, which also may or may not be provided in the kit.

The kit may also contain conventional pharmaceutical adjunct materials such as, for example, pharmaceutically acceptable salts to adjust the osmotic pressure, buffers, preservatives, antioxidants and the like.

In certain embodiments, an antioxidant and a transition chelator are included in the composition to prevent oxidation of the $N_4$ conjugate. However, it is contemplated that any other antioxidant known to those of ordinary skill in the art, such as tocopherol, pyridoxine, thiamine, or rutin, may also be used. Examples of transition chelators for use in the present invention include, but are not limited to, glucoheptonate, gluconate, glucarate, citrate and tartarate. The components of the kit may be in liquid, frozen or dry form. In certain embodiments, kit components may be provided in lyophilized form.

VI. Pharmaceutical Preparations

Pharmaceutical compositions of the present invention comprise an effective amount of an $N_4$ conjugate of the present invention dissolved or dispersed in a pharmaceutically acceptable carrier. The phrases "pharmaceutical" and "pharmacologically acceptable" refer to molecular entities and compositions that do not produce an adverse, allergic, or other untoward reaction when administered to an animal, such as, for example, a human, as appropriate. The preparation of a pharmaceutical composition that contains at least one $N_4$ conjugate, such as a radiolabelled $N_4$ conjugate, or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, and general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated. Other examples of pharmaceutically acceptable carriers include glutamic acid and other mild acids, and cold metals.

An $N_4$ conjugate of the present invention may comprise different types of carriers depending on whether it is to be administered in solid, liquid, or aerosol form, and whether it needs to be sterile for such routes of administration such as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), or by other method or any combination of the foregoing as would be known to one of ordinary skill in the art (see, for example, Remington's Pharmaceutical Sciences, 18th Ed. Mack Printing Company, 1990).

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, about or at least about 0.1% of an $N_4$ conjugate. In other embodiments, the active compound (e.g., an $N_4$ conjugate) may comprise between about 2% to about 75% of the weight of the unit, or between about 25% to about 60%, for example, and any range derivable therein. In other non-limiting examples, a dose may also comprise from about 0.1 mg/kg/body weight, 0.5 mg/kgl body weight, 1 mg/kg/body weight, about 5 mg/kg/body weight, about 10 mg/kg/body weight, about 20 mg/kg/body weight, about 30 mg/kg/body weight, about 40 mg/kg/body weight, about 50 mg/kg/body weight, about 75 mg/kg/body weight, about 100 mg/kg/body weight, about 200 mg/kg/body weight, about 350 mg/kg/body weight, about 500 mg/kg/body weight, about 750 mg/kg/body weight, to about 1000 mg/kg/body weight or more per administration, or any range derivable therein. In non-limiting examples of a derivable range from the numbers listed herein, a range of about 10 mg/kg/body weight to about 100 mg/kg/body weight, etc., can be administered, based on the numbers described above.

In any case, the composition may comprise various antioxidants to retard oxidation of one or more components. Additionally, prevention of the action of microorganisms can be brought about by preservatives such as various antibacterial and antifungal agents, including, but not limited to parabens (e.g., methylparabens, propylparabens), chlorobutanol, phenol, sorbic acid, thimerosal, or combinations thereof.

An $N_4$ conjugate may be formulated into a composition in a free base, neutral or salt form. Such forms are well-known to those of skill in the art. Pharmaceutically acceptable salts include, for example, the salts formed with the free carboxyl groups derived from inorganic bases such as for example, sodium, potassium, ammonium, calcium or ferric hydroxides; or such organic bases as isopropylamine, trimethylamine, histidine, or procaine.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example, liquid polyol or lipids; by the use of surfactants such as, for example, hydroxypropylcellulose; or combinations thereof such methods. In many cases, isotonic agents, such as, for example, sugars, sodium chloride or combinations thereof, may be included.

Sterile injectable solutions may be prepared by incorporating an $N_4$ conjugate in the required amount of the appropriate solvent with various amounts of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin, or combinations thereof.

VII. Combinational Therapy

It is an aspect of this invention that $N_4$ conjugates, such as a radiolabelled $N_4$ conjugate, of the present invention can be used in combination with another agent or therapy method, e.g., another cancer treatment. The $N_4$ conjugate may precede or follow the other agent treatment by intervals ranging from minutes to weeks. In embodiments where the other agent and the $N_4$ conjugate are applied separately, one would generally ensure that a significant period of time did not expire between the time of each delivery, such that the agent and the $N_4$ conjugate would still be able to exert an advantageously combined effect. For example, in such instances, it is contemplated that one may contact the cell, tissue or organism with two, three, four or more agents substantially simultaneously (i.e., within less than about a minute) with an $N_4$ conjugate. In other aspects, one or more agents may be administered within about, at least about, or at most about 1 minute, 5 minutes, 10 minutes, 20 minutes 30 minutes, 45 minutes, 60 minutes, 2 hours, 3 hours, 4 hours, 5 hours, 6 hours, 7 hours 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, to, at least, or 48 hours or more prior to and/or after administering the $N_4$ conjugate. In certain other embodiments, an agent may be administered within about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20, to 21 days prior to and/or after administering the $N_4$ conjugate. In some situations, it may be desirable to extend the time period for treatment significantly, however, where several weeks (e.g., 1, 2, 3, 4, 5, 6, 7 or 8 weeks or more) lapse between the respective administrations.

Various combination regimens of the agents may be employed. Non-limiting examples of such combinations are shown below, wherein the $N_4$ conjugate is "A" and the secondary agent, which can be any other therapeutic agent, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of an $N_4$ conjugate of the present invention to a patient will follow general protocols for the administration of chemotherapeutics, taking into account the toxicity, if any, of the conjugate. It is expected that the treatment cycles would be repeated as necessary. It also is contemplated that various standard therapies, as well as surgical intervention, may be applied in combination with the $N_4$ conjugate. These therapies include but are not limited to chemotherapy, radiotherapy, immunotherapy, gene therapy and surgery. Certain of these therapies are described in more detail below.

A. Chemotherapy

Cancer therapies include a variety of combination therapies with both chemical and radiation based treatments. Combination chemotherapy include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP 16), tamoxifen, raloxifene, estrogen receptor binding agents, taxol, gemcitabien, navelbine, farnesyl-protein transferase inhibitors, cisplatin, 5-fluorouracil, vincristin, vinblastin and methotrexate, or any analog or derivative variant of the foregoing.

B. Radiotherapy

Factors that cause DNA damage that have been used extensively in various cancer treatments include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionucleotide, ricin A chain, cholera toxin, pertussis toxin, etc.) and serve merely as a targeting ligand. Alternatively, the effector may be a lymphocyte carrying a surface molecule that interacts, either directly or indirectly, with a tumor cell target. Various effector cells include cytotoxic T cells and NK cells.

Immunotherapy could thus be used as part of a combined therapy, possibly in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Gene Therapy

In yet another embodiment, the secondary treatment is a secondary gene therapy. For example, a therapeutic polynucleotide may be administered before, after, or at the same time a first therapeutic agent. Delivery of the therapeutic agent in conjunction with an $N_4$ conjugate may have a combined anti-hyperproliferative effect on target tissues.

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. Curative surgery includes resection in which all or part of cancerous tissue is physically or partially removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

VIII. EXAMPLES

The following examples are included to demonstrate certain preferred embodiments of the invention. It should be appreciated by those of skill in the art that the techniques disclosed in the examples which follow represent techniques discovered by the inventor to function well in the practice of the invention, and thus can be considered to constitute certain preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Protection of $N_4$ Compounds for N-Mono Substitutes

A. Protection of Cyclam with Ethyl Trifluoroacetate

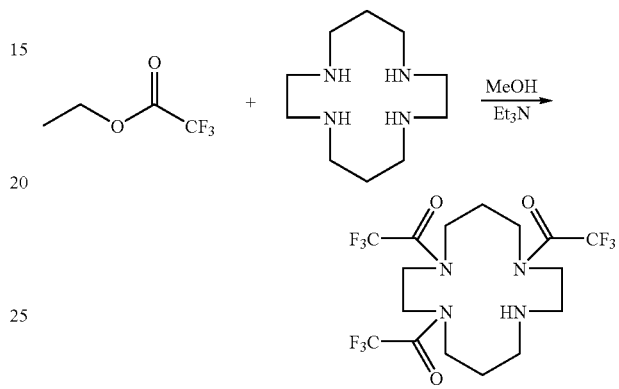

4.006 g (20 mmol) of cyclam (1,4,8,11-tetraazacyclotetradecane) was placed into a solution of 2.79 ml of triethylamine in 15 ml of dried methanol. 6.92 ml of ethyl trifluoroacetate was added dropwise to the upper solution at room temperature with stirring. The addition continued over a period of 5 min. The homogeneous reaction mixture was cooled with an ice-water bath to control the mild exothermicity. Stirring was continued under nitrogen for 5 hours. Volatiles were removed in vacuo. The residue was passed through a small silica-gel plug (25 g) and eluted with 100% ethyl acetate. The eluted solvent was concentrated to give the product as a white foam (8.972 g, 95% yield).

B. Protection of Cyclen with Ethyl Trifluoroacetate

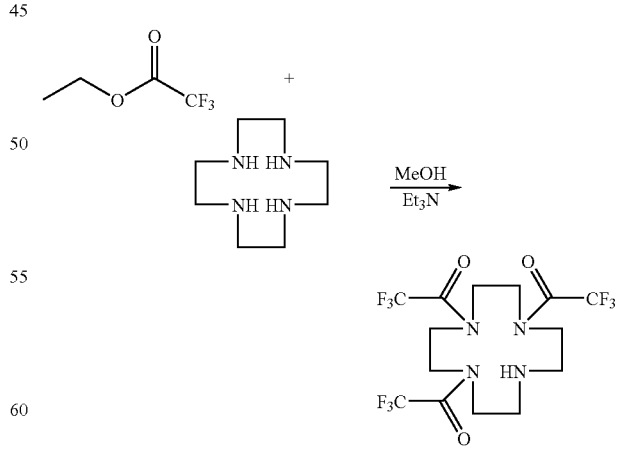

The same protocol as described in Example 1A was used for this reaction, with the substitution of 3.445 mg (20 mmol) of cyclen (1,4,7,10-tetraazacyclododecane) (8.276 g, 93% yield).

C. Protection of Cyclal with Ethyl Trifluoroacetate

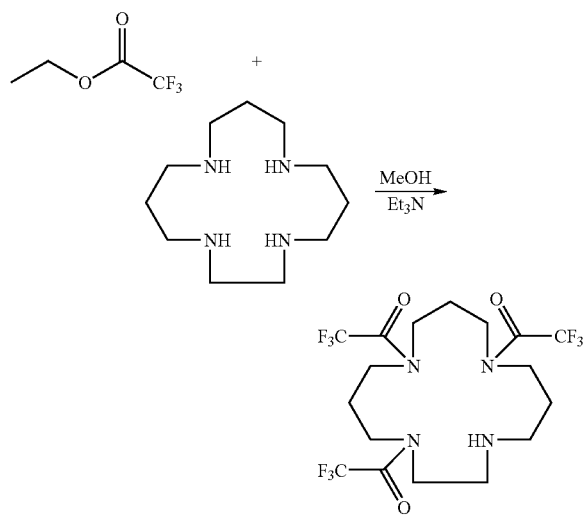

The same protocol as described in Example 1A was used for this reaction, with the substitution of 4.287 g (20 mmol) of cyclal (1,4,8,12-tetraazacyclopentadecane) (9.227 g, 95% yield).

Example 2

Preparation of Sulfonated and Iodinated Tyrosine Derivatives

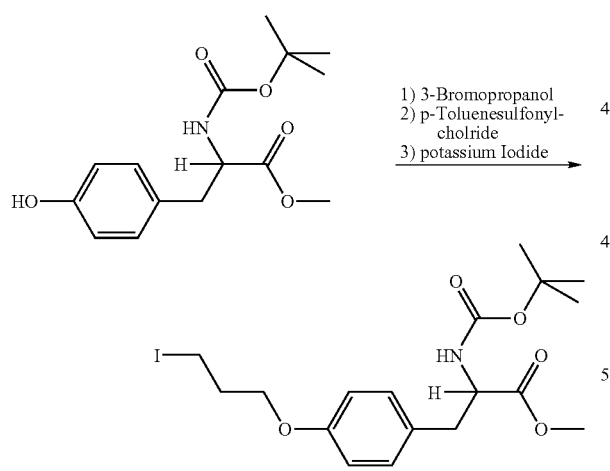

A. O-Alkylation of Tyrosine with 3-Bromopropanol 2953.3 mg (10 mmol) of N-(tert-butoxycarbonyl)-L-tyrosine methyl ester (Boc-Tyr) in 30 ml of anhydrous methanol solution was added into 50 ml of methanol solution containing of 540.2 mg (10 mmol) of sodium methoxide. 1363 µL (15 mmol) of 3-bromopropanol was added to the upper Boc-Tyr solution. The mixture was stirred at 70° C. for 6 hours after at room temperature for 20 min under a nitrogen atmosphere. The mixture was dissolved in 20 ml of ethyl acetate after evaporation under reduced pressure in order to remove volatiles. The organic layer washed with water (2×20 ml), dried with anhydrous magnesium sulfate and solvent was removed using a rotary evaporator. A clear liquid that turned to a white solid (hydroxypropyl-Boc-Tyr (HOPr-Boc-Tyr), 2.9158 g, 82.5% yield) was yielded through column chromatography using a hexane-ethyl acetate gradient (10:1 to 1:1).

B. Tosylation of 3-Hydroxypropyl-Boc-Tyr 1413.6 mg (4.0 mmol) of HOPr-Boc-Tyr in 10 ml of anhydrous pyridine was poured into a solution of 1143.9 mg (6.0 mmol) of p-toluenesulfonyl chloride in 20 ml of anhydrous pyridine with stirring in an ice-water bath under a nitrogen atmosphere. The mixture was placed in a refrigerator overnight. The reaction mixture can be followed by the development of color, followed by filter separation of pyridine hydrochloride. The filtrate was evaporated under reduced pressure in order to remove pyridine. A white solid (1.8123 g, 87.9% yield) was yielded through column chromatography using a hexane-ethyl acetate gradient (10:1 to 2:1).

C. Synthesis of 3-Iodopropyl-Boc-Tyr (1-Pr-Boc-Tyr)

Potassium iodide 1992.1 mg (12 mmol) was poured into the solution of TsO—Pr-Boc-Tyr (1522.8 mg, 3.0 mmol) in 15 ml of anhydrous acetonitrile. The mixture did not fully dissolve and was allowed to reflux for 2 hours. The solid was removed by filtration and the filtered solution was evaporated to remove acetonitrile. The residue was isolated by column chromatography using a hexane:ethyl acetate gradient (10:1 to 10:4). A clear liquid (1324.5 mg) was recovered (95.3% yield).

Example 3

Preparation of Sulfonated and Iodinated α-Methyltyrosine Derivatives

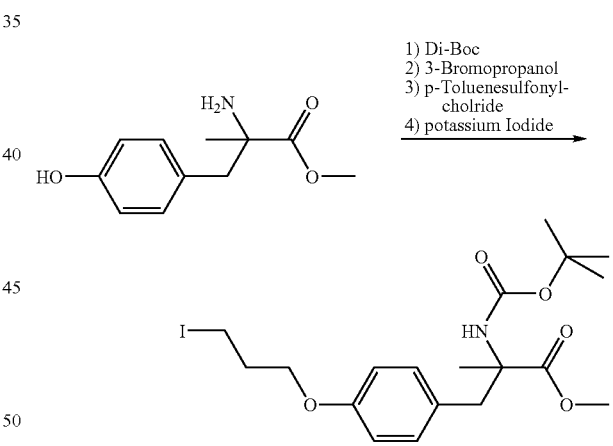

A. N-Protection of α-Methyltyrosine

Di-tert-butyl dicarbonate 13.095 g (60 mmol) was added to a solution of α-methyltyrosine (AMT) (8.370 g, 40 mmol) and anhydrous triethylamine (11.2 ml, 80 mmol) in 40 ml of anhydrous DMF. After stirring overnight at room temperature, the mixture was evaporated under reduced pressure followed by filtration. A white solid (Boc-AMT, 11.217 g, 90.6% yield) was gained through column isolation of the residue using a hexane-ethyl acetate gradient (10:1 to 10:7).

B. O-Alkylation of Boc-AMT with 3-Bromopropanol

The procedure of Example 2A was followed with the substitution of 3.094 g (10 mmol) of Boc-AMT. A clear liquid, which turned to a white solid (HO—Pr-Boc-AMT, 3.289 g, 89.5% yield) was yielded through column chromatography using a hexane-ethyl acetate gradient (10:1 to 10:5).

C. Tosylation of 3-HO—Pr-Boc-AMT

The procedure of Example 2B was followed with the substitution of 2.940 g (8.0 mmol) of HO—Pr-Boc-AMT. A white solid (TsO—Pr-Boc-AMT, 3.493 g, 83.7% yield), was yielded through column chromatography using a hexane-ethyl acetate gradient (10:1 to 10:5).

D. Synthesis of 3-Iodopropyl-Boc-Tyr (1-Pr-Boc-Tyr)

The procedure of Example 2C was followed with the substitution of 3.130 g (6.0 mmol) of TsO-Pr-Boc-AMT. A clear liquid (1-Pr-Boc-AMT), 2.801 g (97.8% yield), was yielded through column chromatography using hexane-ethyl acetate gradient (10:1 to 10:4).

Example 4

Preparation of Sulfonated and Iodinated Tamoxifen Derivatives

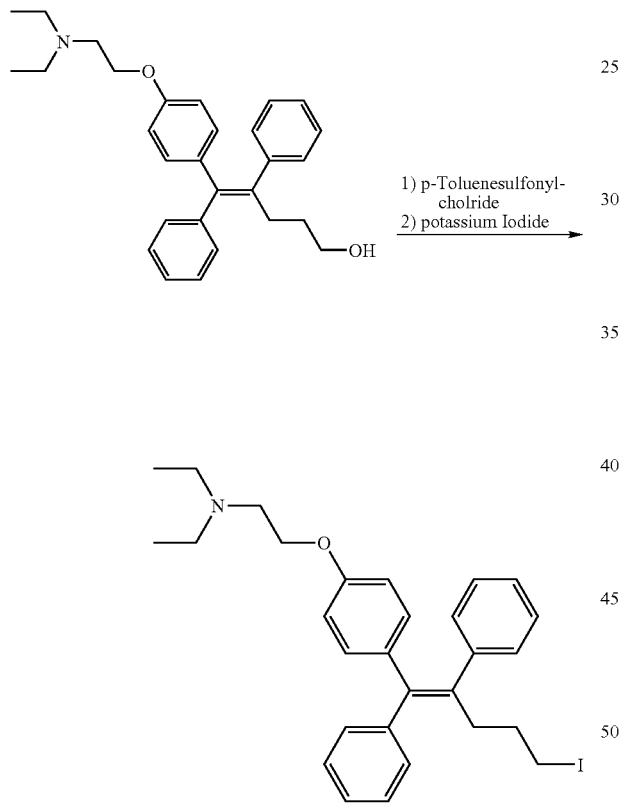

A. Tosylation of 4-Hydroxymethyl-N,N-Diethyl Tamoxifen

The procedure of Example 2B was followed with the substitution of 1.289 g (8.0 mmol) of 4-hydroxymethyl-N,N-diethyl tamoxifen (HO-TMX). A pale yellow liquid (TsO-TMX), 1.445 g (82.5% yield), was yielded through column chromatography using a hexane:ethyl ether:triethylamine gradient (100:100:5 to 100:100:20).

B. Synthesis of 4-Iodomethyl-N,N-Diethyl Tamoxifen

The procedure of Example 2C was followed with the substitution of 1.168 g (2.0 mmol) of I-TMX. A clear liquid (I-TMX, 1.058 g, 98.1% yield), was yielded after passing through a short column using a hexane:ethyl ether:triethylamine gradient (100:100:1 to 100:100:10).

Example 5

Preparation of Sulfonated and Iodinated Estrone Derivatives

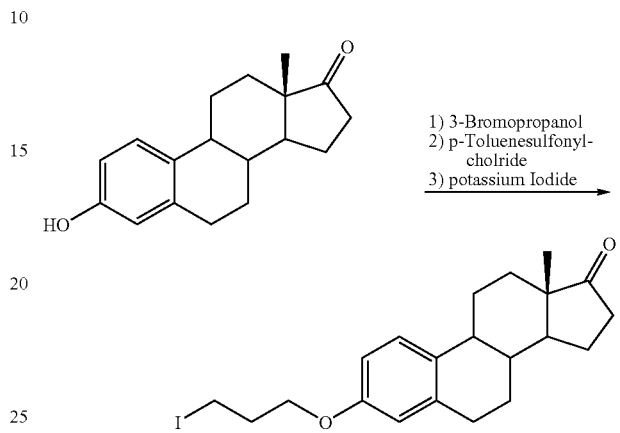

A. O-Alkylation of Estrone (EST) with 3-Bromopropanol

The procedure of Example 2A was followed with the substitution of 2.703 g (10 mmol) of estrone. A clear liquid, which turned to a white solid (HO—Pr-EST, 2.405 g, 73.2% yield) was yielded through column chromatography using a hexane-ethyl acetate:gradient (10:1 to 10:5).

B. Tosylation of HO—Pr-EST

The procedure of Example 2B was followed with the substitution of 1.971 g (6.0 mmol) of HO—Pr-EST. A white solid (TsO—Pr-EST, 2.253 g, 77.8% yield) was yielded through column chromatography using a hexane-ethyl acetate gradient (10:1 to 10:5).

C. Synthesis of 3-Iodopropyl-EST

The procedure of Example 2C was followed with the substitution of 1.930 g (4.0 mmol) of TsO—Pr-EST. A clear liquid (I—Pr-EST, 1.720 g, 98.1% yield) was yielded through column chromatography using a hexane-ethyl acetate gradient (10:1 to 10:4).

Example 6

Reaction of Cyclal with 1,3,4,6-Tetra-O-acetyl-2-O-trifluoromethanesulfonyl-β-D-mannopyranose (A Precursor for FDG Synthesis)

A. Example of N,N',N",N"'-Tetra-Substituted Cyclal-DG

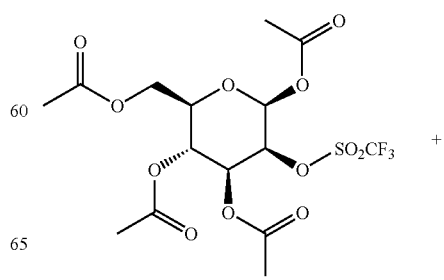

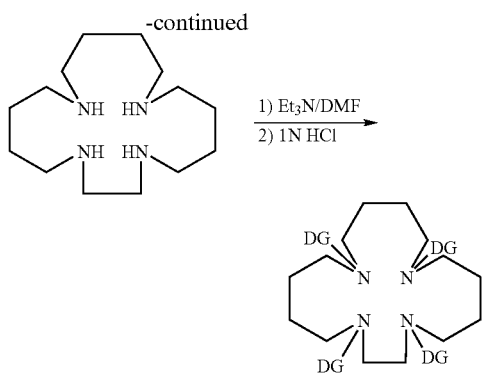

1,3,4,6-Tetra-O-acetyl-2-O-trifluoromethanesulfonyl-β-D-mannopyranose (200 mg, 0.416 mmol) was placed into a solution of cyclal (22.3 mg, 0.104 mmol) and triethylamine (84.2 mg, 116 µL, 0.832 mmol) in anhydrous DMF (10 ml). The mixture was stirred at 50° C. for 16 hours under a nitrogen atmosphere and evaporated to remove volatiles. The residue put into 1,4-dioxane (6 ml), upon which a white precipitate formed. The precipitate was removed through filtration. 1 ml 4N HCl in 1,4-dioxane was then added dropwise to the filtrate, and a pale brown powder precipitated. The powder was collected via filtration and dried through lyophilization. The dried solid was next dissolved in 1N HCl (3 ml) and stirred for 30 min. 1N NaHCO$_3$ was added to the upper solution until the pH reached approximately 9. The solution was purified using a membrane (MW cutoff<500), and evaporated under lyophilization. A pale brown solid (63.2 mg, 67.2% yield) was collected.

B. Example of N,N',N'''-Tri-Substituted Cyclal-DG 1,3,4,6-Tetra-O-acetyl-2-O-trifluoromethanesulfonyl-β-D-mannopyranose (200 mg, 0.416 mmol) was placed into a solution of cyclal (29.6 mg, 0.138 mmol) and triethylamine (84.2 mg, 116 µL, 0.832 mmol) in anhydrous DMF (10 ml). The mixture was stirred at 50° C. for 16 hours under a nitrogen atmosphere and evaporated to remove volatiles. The residue placed into 6 ml of 1,4-dioxane, upon which a white precipitate formed. The precipitate was removed through filtration. 1 ml 4N HCl in 1,4-dioxane was added dropwise to the filtrate, and a pale brown powder precipitated. The powder was collected via filtration and dried through lyophilization. The dried solid was dissolved in 1N HCl (3 ml) and stirred for 30 min. 1N NaHCO$_3$ was added to the upper solution until the pH reached approximately 9. The solution was purified with a membrane (MW cutoff<500), and evaporated under lyophilization. A pale brown solid (58.8 mg, 57.4% yield) was collected.

C. Example of N,N'-Di-Substituted Cyclal-DG 1,3,4,6-Tetra-O-acetyl-2-O-trifluoromethanesulfonyl-β-D-mannopyranose (200 mg, 0.416 mmol) was placed into a solution of cyclal (44.6 mg, 0.208 mmol) and triethylamine (84.2 mg, 116 µL, 0.832 mmol) in anhydrous DMF (10 ml). The mixture was stirred at 50° C. for 16 hours under a nitrogen atmosphere and evaporated to remove volatiles. The residue placed into 6 ml of 1,4-dioxane, upon which a white precipitate formed. The precipitate was removed through filtration. 1 ml 4N HCl in 1,4-dioxane was added dropwise to the filtrate, and a pale brown powder precipitated. The solid was collected with filtering and dried under lyophilizer. The powder was collected via filtration and dried through lyophilization. The dried solid was dissolved in 1N HCl (3 ml) and stirred for 30 min. 1N NaHCO$_3$ was added to the upper solution until the pH reached approximately 9. The solution was purified with a membrane (MW cutoff <500), and evaporated under lyophilization. A pale brown solid (23.9 mg, 19.8% yield) was collected through lyophilization after Sephadex G-75 isolation.

D. Example of N-Mono-Substituted Cyclal-DG 1,3,4,6-Tetra-O-acetyl-2-O-trifluoromethanesulfonyl-β-D-mannopyranose (200 mg, 0.416 mmol) was placed into a solution of N,N',N''-tris(trifluoroacetyl)-cyclal from Example 1C (209 mg, 0.416 mmol) and triethylamine (84.2 mg, 116 µL, 0.832 mmol) in anhydrous DMF (10 ml). The mixture was stirred at 50° C. for 6 hours under a nitrogen atmosphere and evaporated to remove volatiles. The residue was put into 6 ml of 1,4-dioxane, upon which a white precipitate formed. The precipitate was removed through filtration. 1 ml 4N HCl in 1,4-dioxane was added dropwise to the filtrate, and a pale brown powder precipitated. The solid collected via filtration was dissolved in 1N HCl (3 ml) and stirred for 30 min. 1N NaHCO$_3$ was added to the upper solution until the pH reached approximately 9. The solution was evaporated under lyophilization and dissolved in minimal water. A white solid (123.3 mg, 78.7% yield) was collected through lyophilization after Sephadex G-25 isolation.

Example 7

Reaction of Cyclal with Iodinated α-Methyltyrosine (AMT)

Similar reaction conditions to the ones presented herein may be used to prepare other cyclal-targeting ligand conjugates.

A. Example of N,N',N'',N'''-Tetra-Substituted AMT

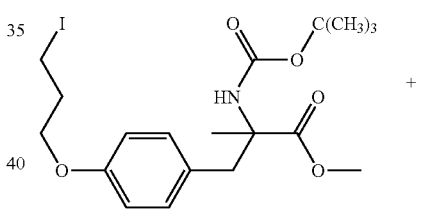

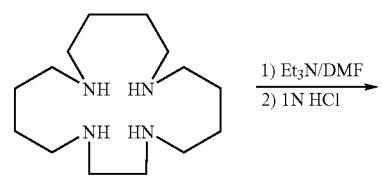

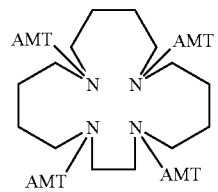

I-AMT (286.4 mg, 0.6 mmol) was placed into a solution of cyclal (32.2 mg, 0.15 mmol) and triethylamine (83.6 µL, 0.6 mmol) in anhydrous DMF (10 ml). The mixture was stirred at 70° C. for 16 hours under a nitrogen atmosphere and evaporated to remove volatiles. 1N HCl (5 ml) was poured into an ethanolic solution (5 ml) of the resulting residue. The reaction mixture was heated at 60° C. for 30 min without a condenser and then cooled. 1N NaHCO₃ was added to the upper solution until the pH reached approximately 9. The solvent was removed under reduced pressure and the residue was dissolved in minimal water. A white solid (91.3 mg, 52.7% yield) was collected through lyophilization after Sephadex G-75 isolation.

B. Example of N,N',N"-Tri-Substituted AMT

I-AMT (286.4 mg, 0.6 mmol) was placed into a solution of cyclal (42.9 mg, 0.2 mmol) and triethylamine (83.6 µL, 0.6 mmol) in anhydrous DMF (10 ml). The mixture was stirred at 70° C. for 16 hours under a nitrogen atmosphere and evaporated to remove volatiles. 1N HCl (5 ml) was poured into an ethanolic solution (5 ml) of the resulting residue. The reaction mixture was heated at 60° C. for 30 min without a condenser and then cooled. 1N NaHCO₃ was added to the upper solution until the pH reached approximately 9. The solvent was removed under reduced pressure and the residue dissolved in minimal water. A white solid (76.7 mg, 41.7% yield) was collected through lyophilization after Sephadex G-75 isolation.

C. Example of N,N'-Di-Substituted AMT

I-AMT (286.4 mg, 0.6 mmol) was placed into a solution of cyclal (64.3 mg, 0.3 mmol) and triethylamine (83.6 µL, 0.6 mmol) in anhydryous DMF (10 ml). The mixture was stirred at 70° C. for 16 hours under a nitrogen atmosphere and evaporated to remove volatiles. 1N HCl (5 ml) was poured into an ethanolic solution (5 ml) of the resulting residue. The reaction mixture was heated at 60° C. for 30 min without a condenser and then cooled. 1N NaHCO₃ was added to the upper solution until the pH reached approximately 9. The solvent was removed under reduced pressure and the residue dissolved in minimal water. A white solid (52.3 mg, 25.9% yield) was collected through lyophilization after Sephadex G-75 isolation.

D. Example of N-Mono Substituted AMT

I-AMT (286.4 mg, 0.6 mmol) was placed into a solution of N,N',N"-tris(trifluoroacetyl)-cyclal (from Examples 1-3) (301.4 mg, 0.6 mmol) and triethylamine (83.6 µL, 0.6 mmol) in anhydrous DMF (10 ml). The mixture was stirred at 70° C. for 6 hours under a nitrogen atmosphere and evaporated to remove volatiles. 1N K₂CO₃ (2 ml) poured into an ethanolic solution (5 ml) of the resulting residue and the mixture was allowed to keep at 40° C. for 1 hour. 1N HCl (9 ml) was next added to the upper solution. The reaction mixture was heated at 60° C. for 30 min without a condenser and then cooled. 1N NaHCO₃ was added to the upper solution until the pH reached approximately 9. The solvent was removed under reduced pressure and the residue dissolved in minimal water. A white solid (233.4 mg, 86.5% yield) was collected through lyophilization after Sephadex G-25 isolation.

Example 8

Reaction of Cyclal with Sulfonated α-Methyltyrosine (TsO-AMT)

Similar reaction conditions to the ones presented herein may be used to prepare other cyclal-targeting ligand conjugates.

A. Example of N,N',N",N'"-Tetra-Substituted AMT

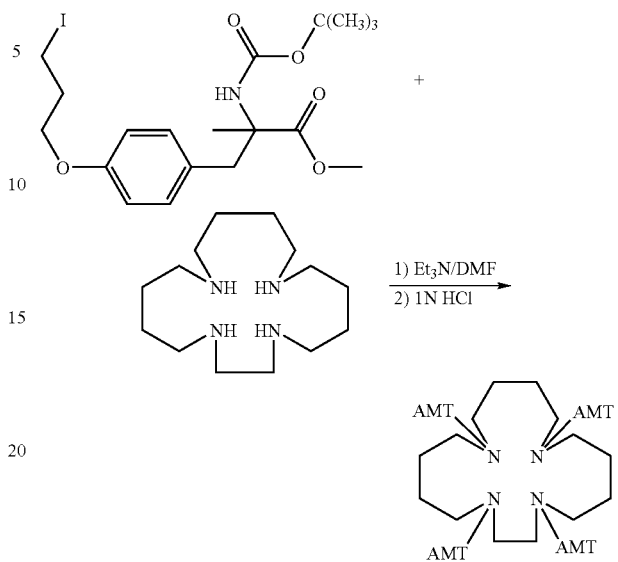

The protocol followed that of Example 7A with the following substitution: TsO-AMT (313 mg, 0.6 mmol) was placed into a solution of cyclal (32.2 mg, 0.15 mmol) and triethylamine (167.2 µL, 1.2 mmol) in anhydrous DMF (10 ml). A white solid (72.3 mg, 41.7% yield) was collected.

B. Example of N,N',N"-Tri-Substituted AMT

The protocol followed that of Example 7B with the following substitution: TsO-AMT (313 mg, 0.6 mmol) was placed into a solution of cyclal (42.9 mg, 0.2 mmol) and triethylamine (167.2 µL, 1.2 mmol) in anhydrous DMF (10 ml). A white solid (56.7 mg, 30.8% yield) was collected.

C. Example of N,N'-Di-Substituted AMT

The protocol followed that of Example 7C with the following substitution: TsO-AMT (313.0 mg, 0.6 mmol) was placed into a solution of cyclal (64.3 mg, 0.3 mmol) and triethylamine (167.2 µL, 1.2 mmol) in anhydrous DMF (10 ml). A white solid (45.4 mg, 22.1% yield) was collected.

D. Example of N-Mono Substituted AMT

The protocol followed that of Example 7D with the following substitution: TsO-AMT (313.0 mg, 0.6 mmol) was placed into a solution of N,N',N"-tris(trifluoroacetyl)-cyclal from Examples 1-3 (301.4 mg, 0.6 mmol) and triethylamine (167.2 µL, 1.2 mmol) in anhydrous DMF (10 ml). A white solid (197.2 mg, 73.1% yield) was collected.

E. Example of Synthesis of 68-Ga—N4-Tyrosine

Figure 11:
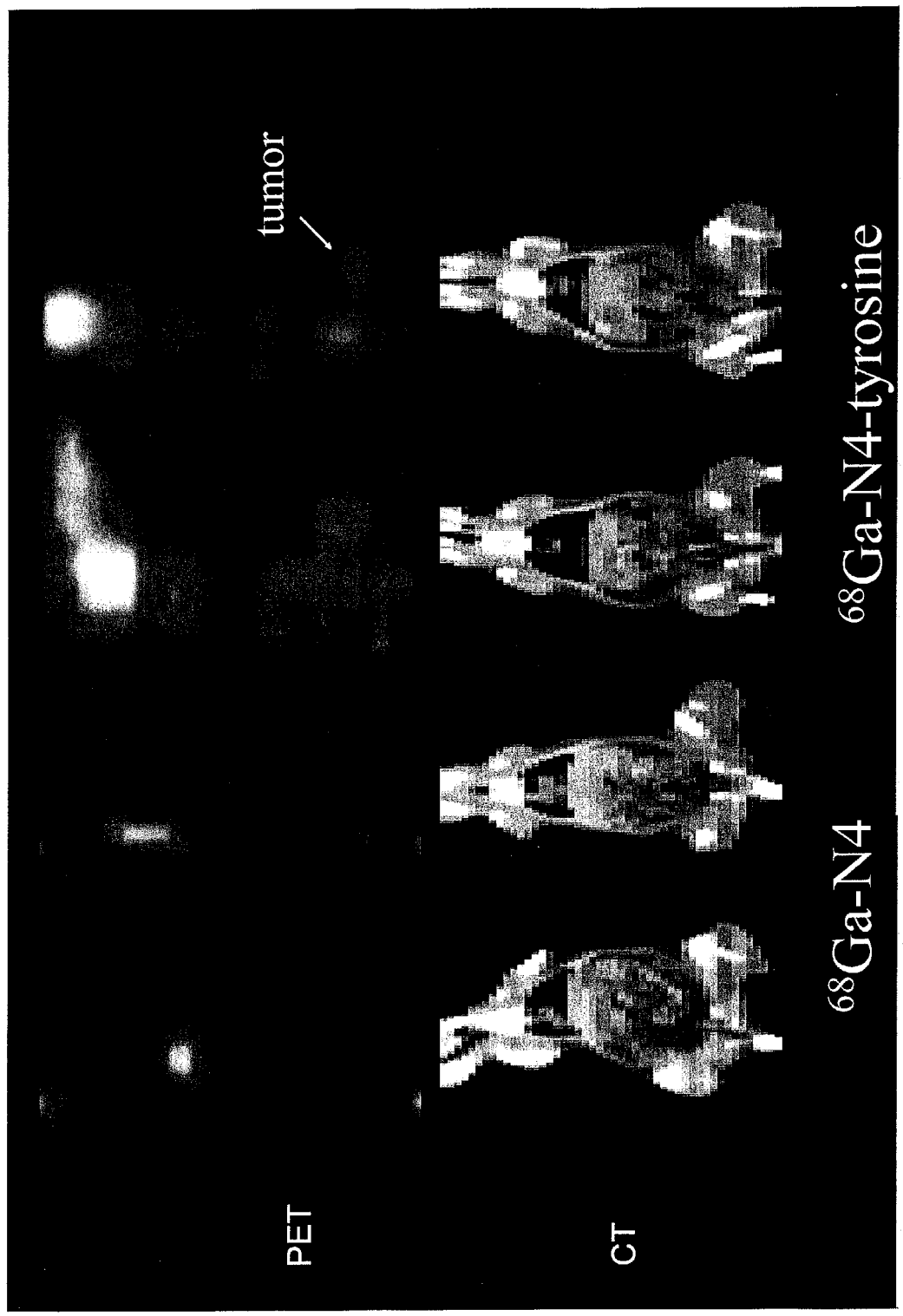
FIG. 11. Dynamic Study of $^{68}$Ga—N4-Tyrosine in Breast Tumor-Bearing Rats. The findings indicated that the tumor could be imaged as early as 3 minutes.
Figure 12:
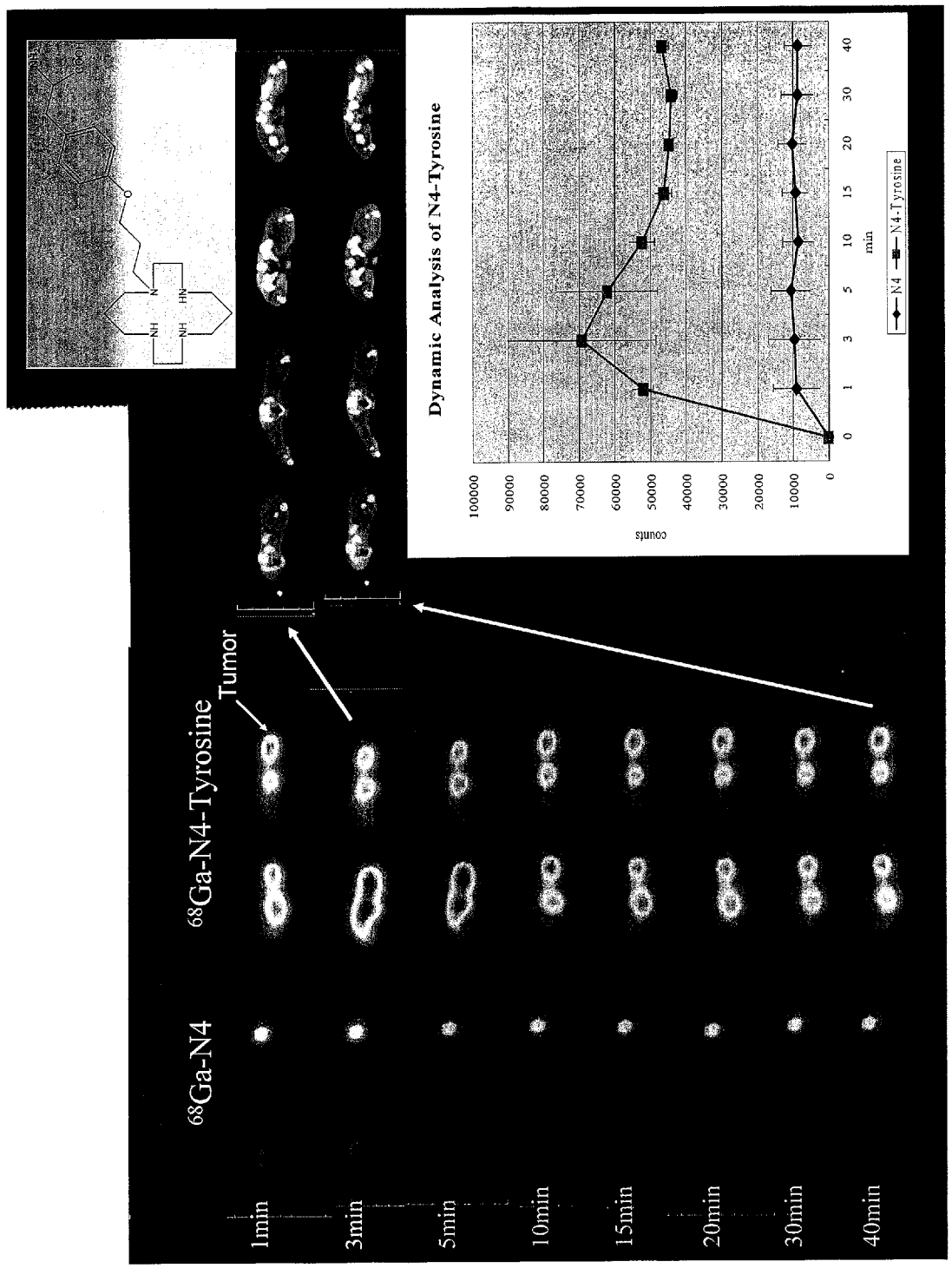
FIG. 12. Dynamic Study of $^{68}$Ga—N4-tyrosine in breast tumor-bearing rats.
Figure 13:
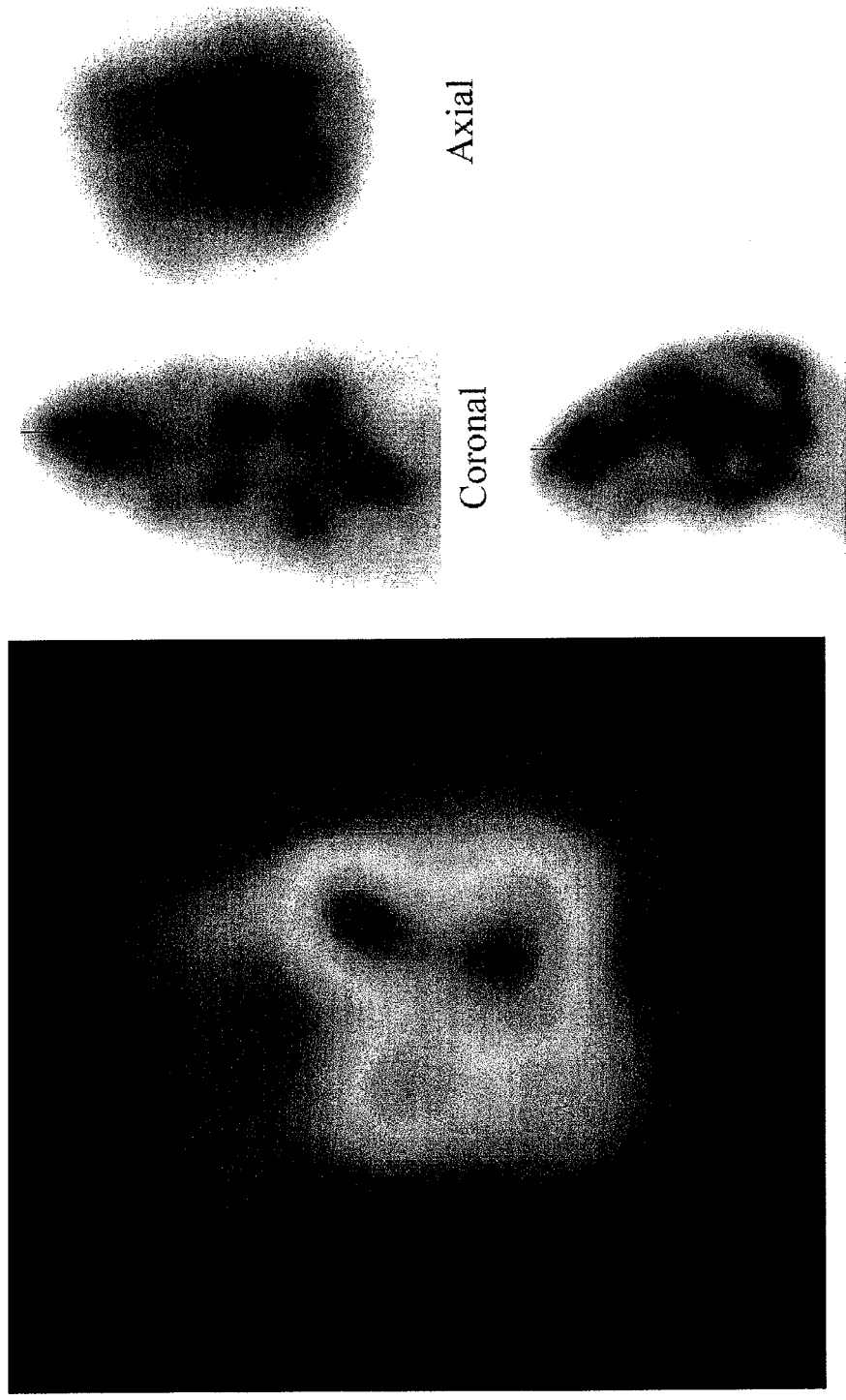
FIG. 13. A female New Zealand white rabbit was administered with 1 mCi of $^{68}$Ga—N4-Tyrosine (iv) and the dynamic images were acquired for 60 min. Basal ganglion in thalamas region could be visualized.
Figure 14:
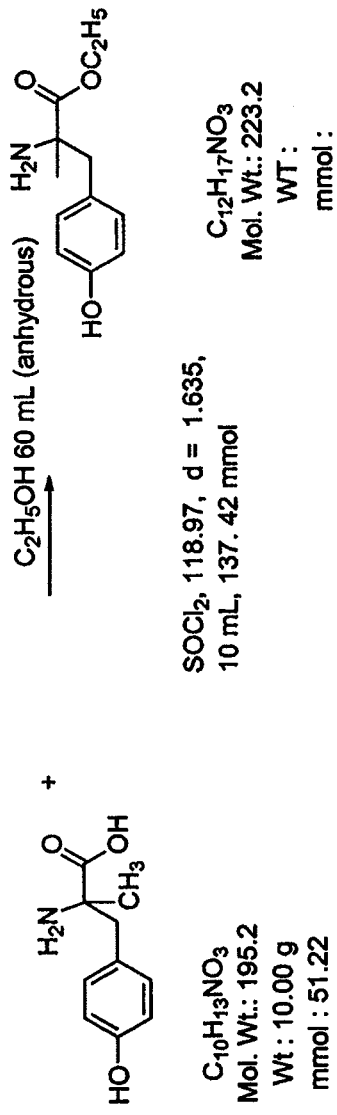
FIG. 14. Protection of acid group to alpha methyl tyrosine.
Figure 15:
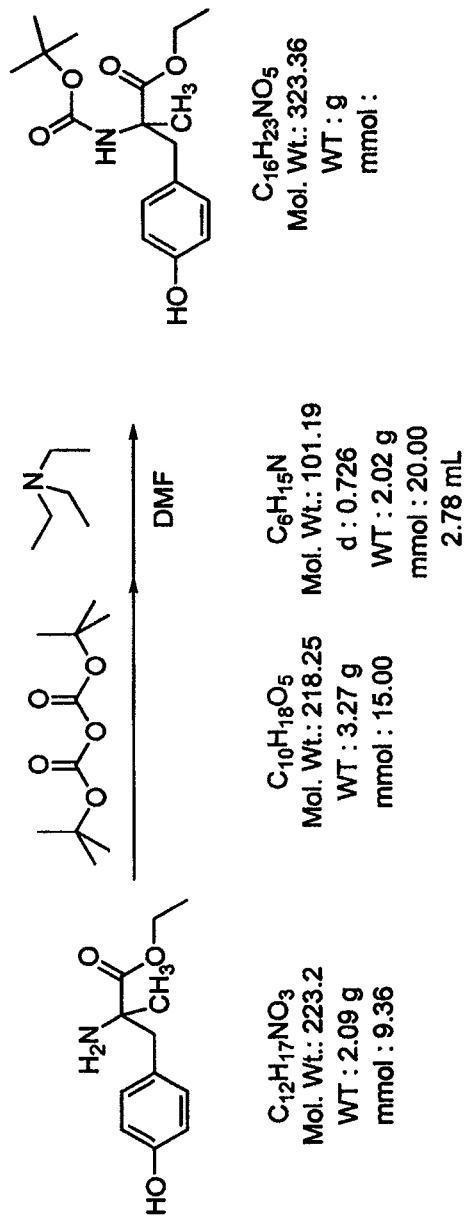
FIG. 15. Protection of amino group on alpha methyl tyrosine.
Figure 16:
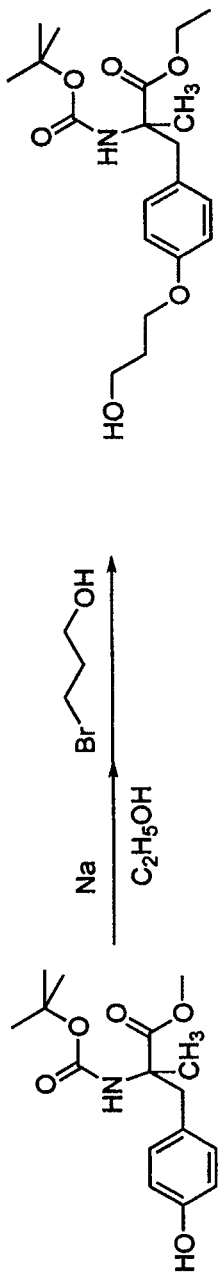
FIG. 16. Synthetic scheme and procedure.
Figure 17:
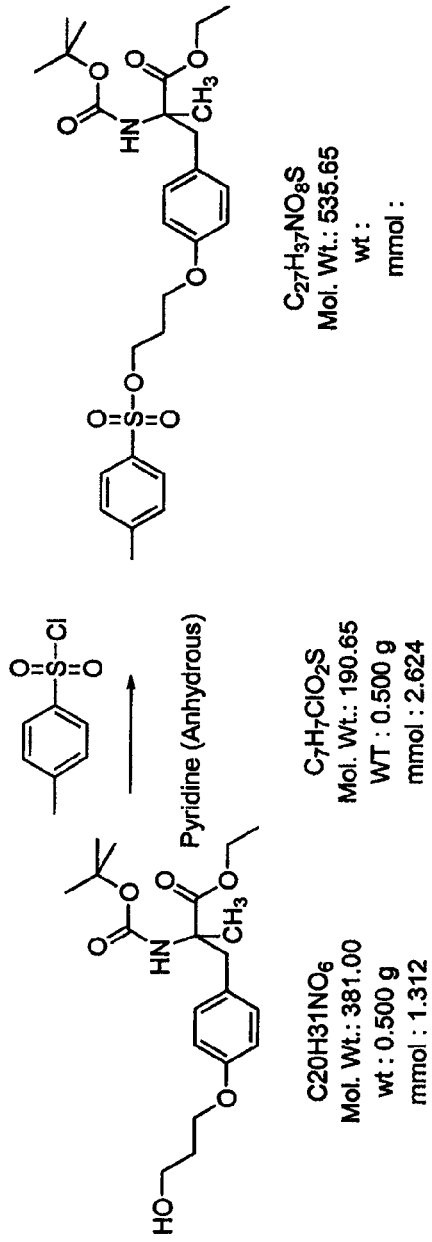
FIG. 17. Tosylation of HO-Pr-AMT
Figure 19:
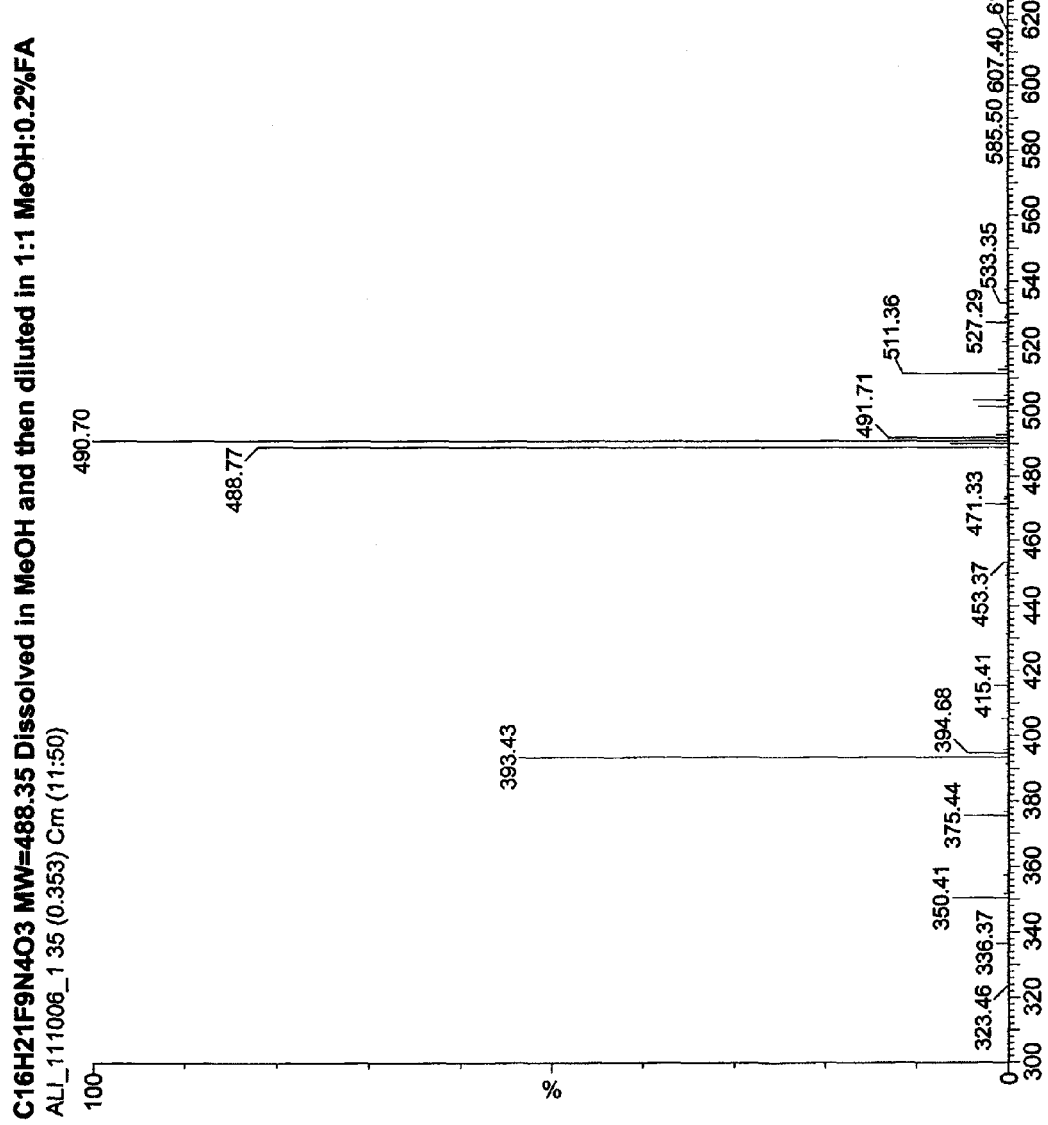
FIG. 19. Synthetic information.
Figure 20:
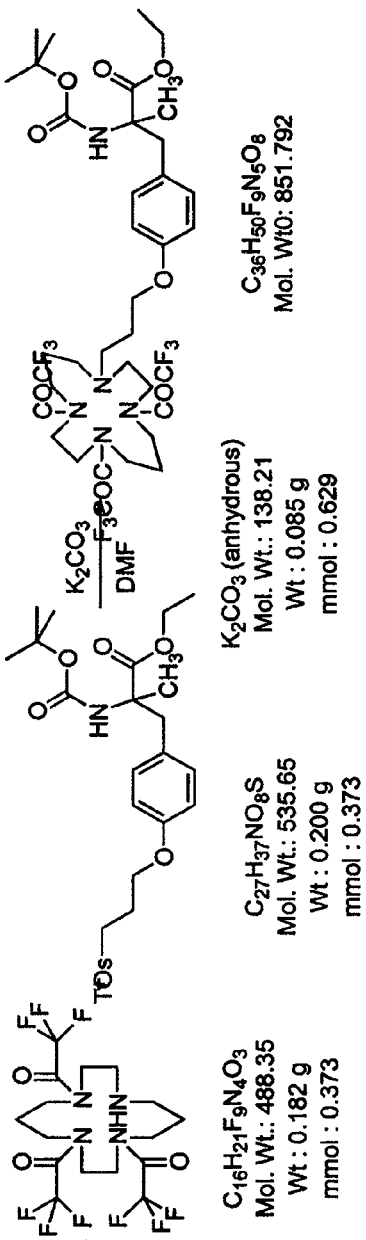
FIG. 20. Rx of tri-protected cyclam (N4) with TsO-alpha methyl tyrosine.
Figure 23:
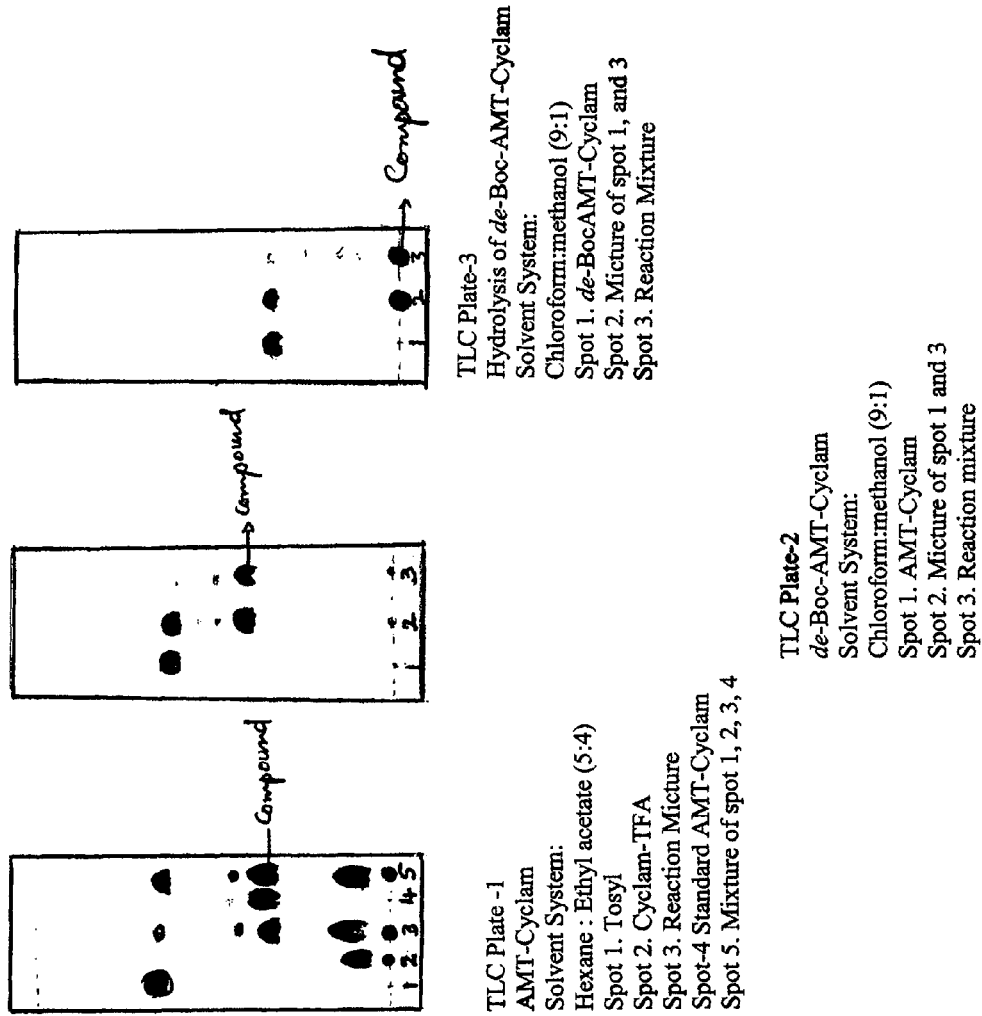
FIG. 23. TLC Plates.
Figure 24:
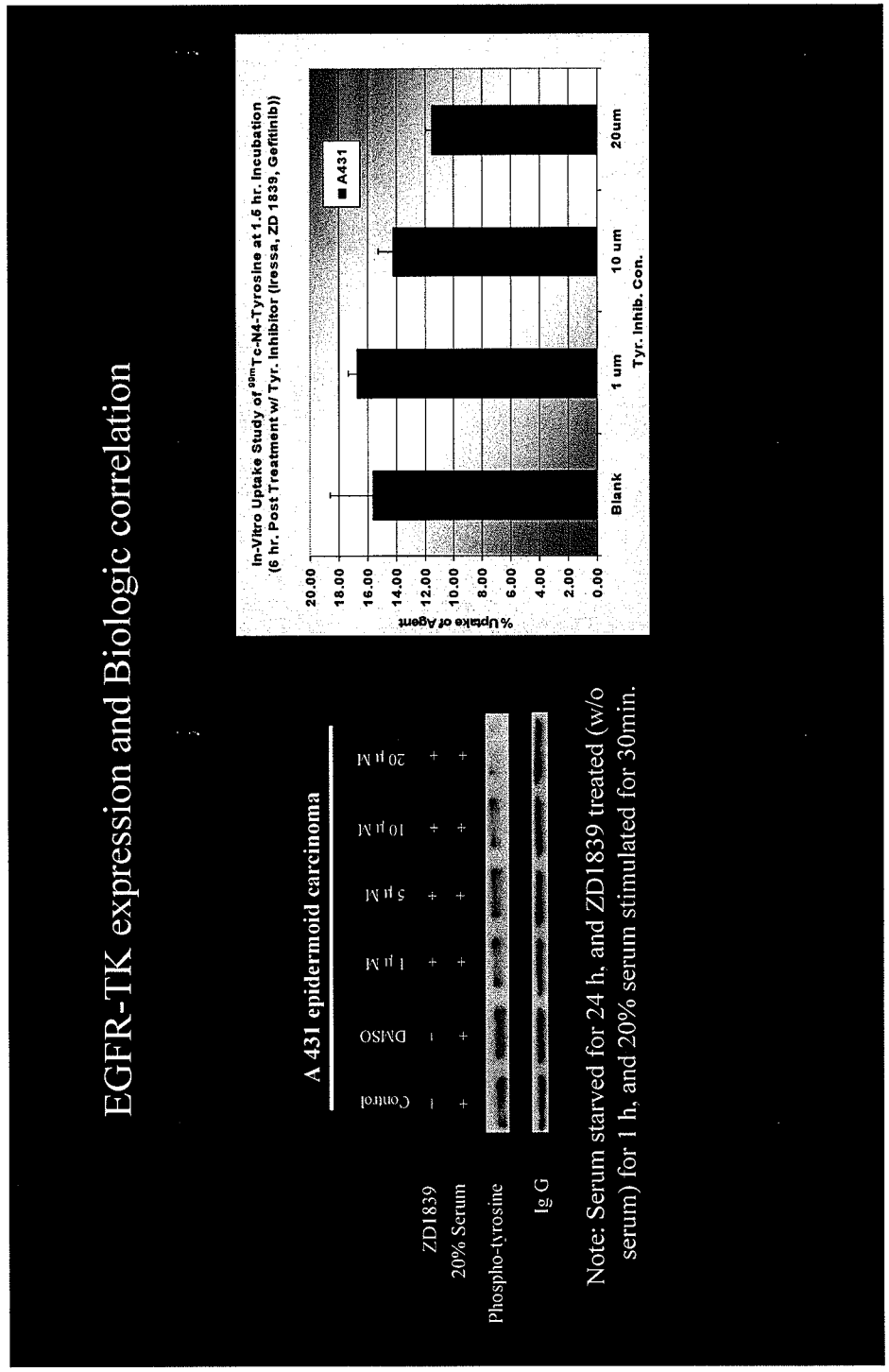
FIG. 24. EGFR-TK expression and biologic correlation
Figure 25:
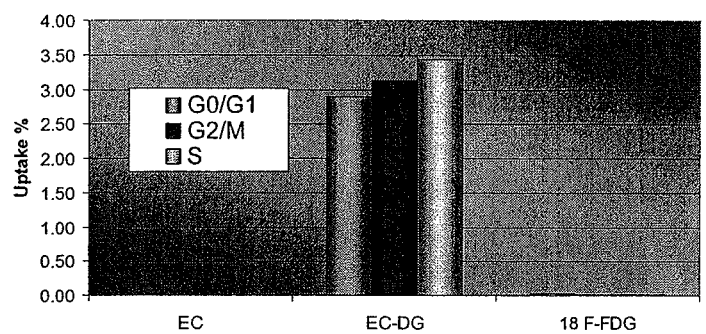
FIG. 25. Effect of N4-glucosamine on cell cycle uptake in breast cancer cells.
Figure 26:
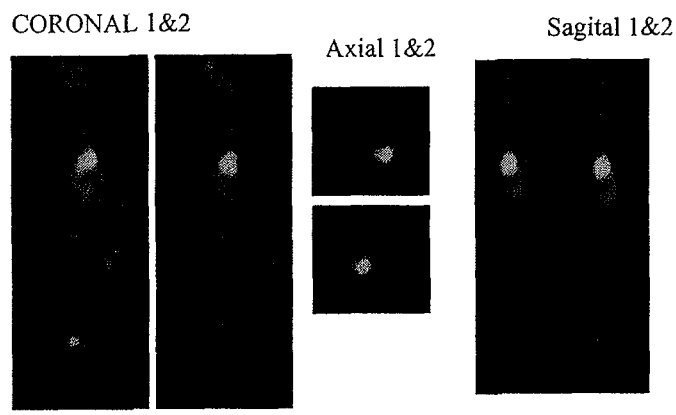
FIG. 26. $^{68}$Ga—N4-TML PET imaging.

Information regarding imaging using 68-Ga—N4 (cyclam)-Tyrosine can be found in FIGS. 11-13. Results of PET dynamic studies demonstrating surprisingly effective imaging of the brain of rat (FIGS. 11-12) and rabbit (FIG. 13). Information regarding the synthesis of 68-Ga—N4-Tyrosine can be found in FIGS. 14-23.

Example 9

Imaging Using N₄ Conjugates

A. Materials and Methods
Reaction of Cyclam with Tetraacetate Mannose Conjugates (N₄-DG-cyclam)
1,3,4,6-Tetra-O-acetyl-2-O-trifluoromethanesulfonyl-β-D-mannopyranose (300 mg, 0.625 mmol) in 5 ml DMF was added to the mixture of 1,4,8,12-tetraazacyclopentacecane (N4) (250.2 mg, 1.237 mmol) and triethylamine (174 μL, 1.249 mmol) in 5 ml of DMF. The reaction mixture was stirred at room temperature for 6 hrs. The reaction solvent was evaporated to dryness at 40-45° C. under high vacuum. 1,4-Dioxane (10 ml) was then added. The precipitate was filtered. Hydrochloric acid (4N) in 1,4-dioxane (2 ml, 8 mmol) was added. The mixture was cooled in an ice-bath. The mixture was filtered through a Büchner funnel and washed with diethyl ether (2×5 ml). The filtrate was evaporated to dryness, yielding a white solid (383.1 mg, 90.8%). 1H-NMR of $N_4$-DG δ (ppm) 8.50 (s, 1H), 3.98-4.01 (m, 1H), 3.76 (s, 2H), 3.54-3.60 (m, 9H), 3.38-3.45 (m, 8H), 3.31-3.37 (m, 1H), 3.18-3.22 (m, 1H), 2.02-2.31 (m, 4H), 2.15 (s, 12H). $^{13}$C-NMR of $N_4$-DG 6 (ppm) 197.3, 175.2, 170.4, 165.6, 67.0, 66.8, 66.4, 51.7, 45.3, 44.0, 43.6, 43.2, 42.9, 42.5, 41.9, 38.6, 37.5, 37.3, 31.8, 19.5, 19.3, 14.5. The synthetic scheme is shown in FIG. 1.

Radiolabeling of $N_4$-DG ($N_4$-DG-cyclam)

$N_4$-DG (5 mg) was dissolved in 0.2 ml water. Tin(II) chloride solution (0.1 ml, 1 mg/ml) was added. Sodium pertechnetate ($Na^{99m}TcO_4$, 37-370 MBq, Mallinckrodt, Houston, Tex.) was added. Finally, water was added to this solution to adjust the volume to 1 ml. Radiochemical purity was determined by TLC (ITLC SG, Gelman Sciences, Ann Arbor, Mich.) eluted with methanol:ammonium acetate (1:4). From radio-TLC analysis (Bioscan, Washington, D.C.), the radiochemical purity was more than 97%.

For $^{68}$Ga-labeling, $^{68}$Ga was eluted from a $^{68}$Ge/$^{68}$Ga generator (Isotope Products Laboratories, Valencia, Calif.) using 1N HCl. The acidic solution was evaporated to dryness with either $GaCl_3$ carrier added or no carrier added. The solution was reconstituted in water. $N_4$-DG (5 mg) dissolved in 0.2 ml water was then added to the radioactive solution.

Figure 2:
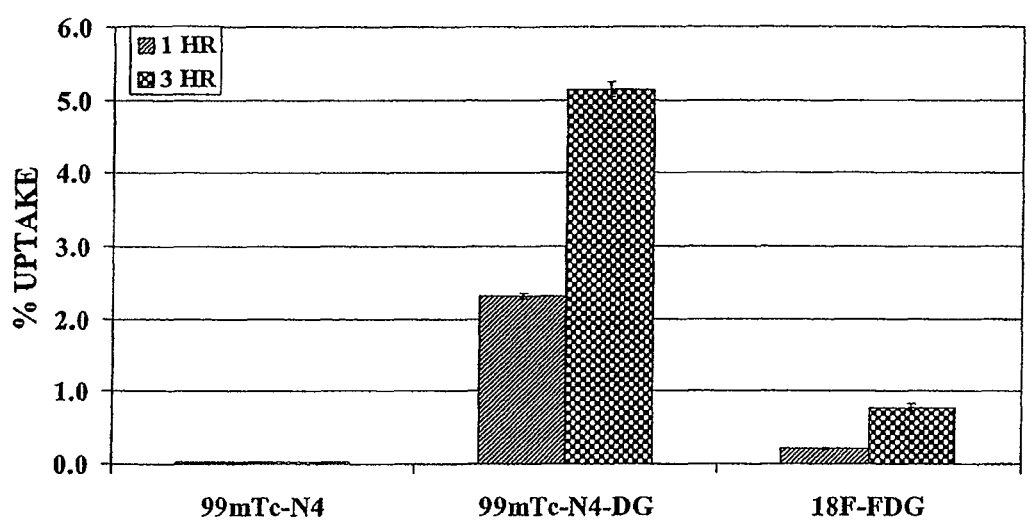
FIG. 2. In vitro cellular uptake of $^{99m}Tc$—$N_4$-DG (cyclam) in 231 breast cancer cells. 50,000 cells/well were plated and allowed to reach 70-80% confluency. Tracers were administered at 4 µCi/well and incubated at 37° C. for 1-3 hrs. Cells were then harvested and radioactivity was counted and quantified.
Figure 3:
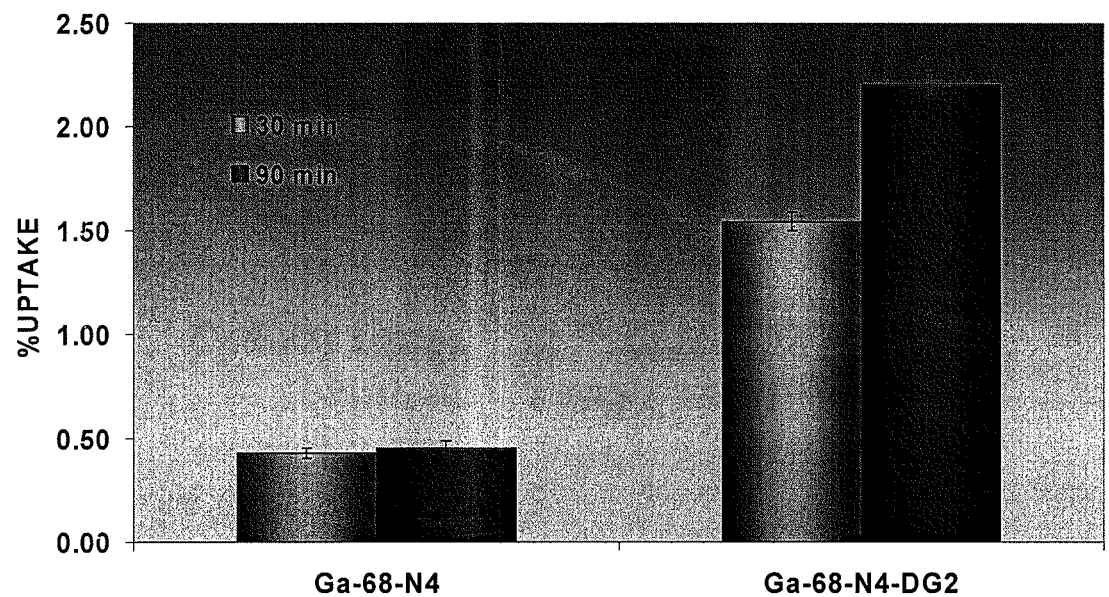
FIG. 3. Cellular uptake of $^{68}Ga$—$N_4$-DG2 (cyclam) in human lung cancer cells. In vitro cellular uptake using A549 cells showed increased uptake of $^{68}Ga$—$N_4$-DG whereas $^{68}Ga$—$N_4$ showed poor uptake.
Figure 4A:
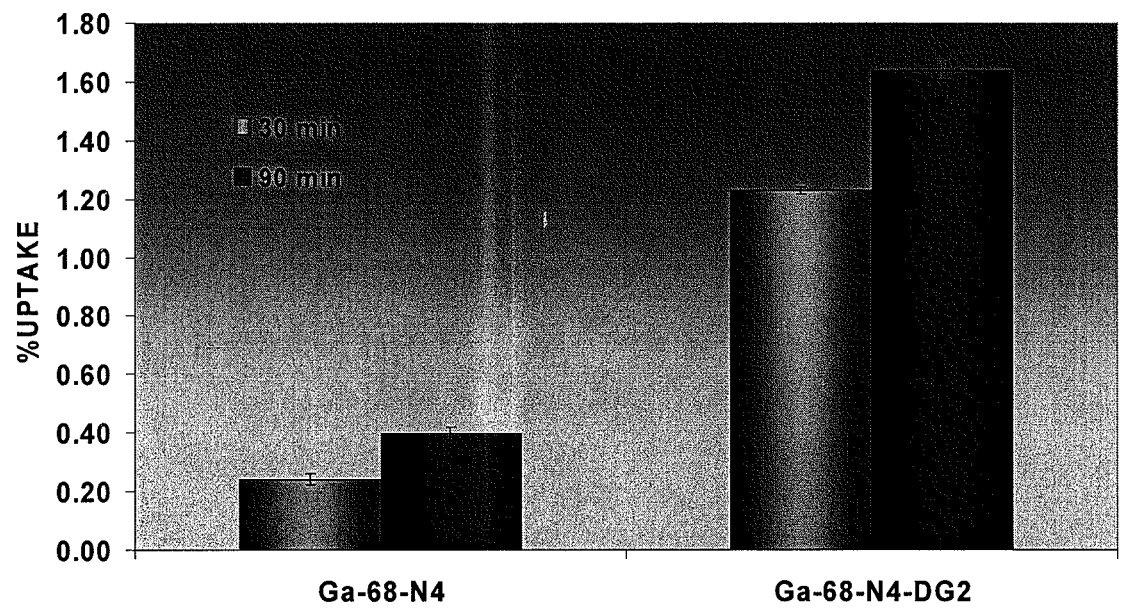
FIGS. 4A-C.
Figure 4B:
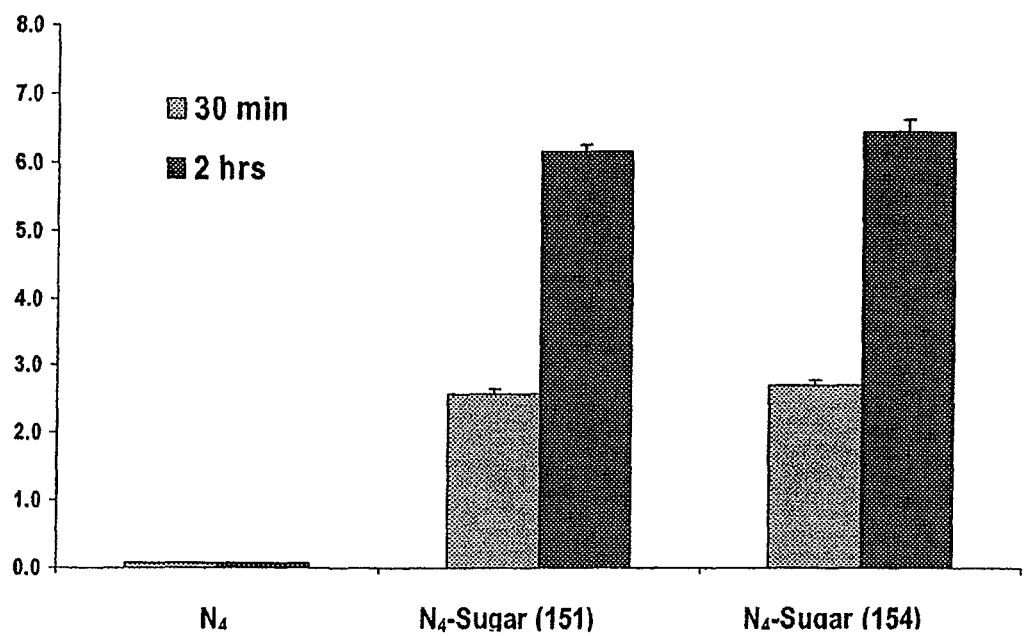
Figure 4C:
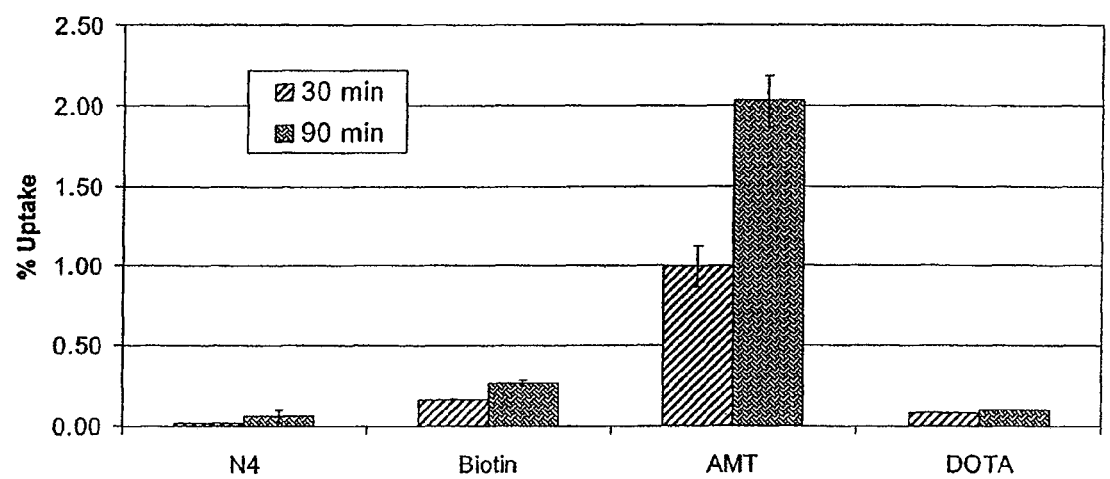
Figure 5A:
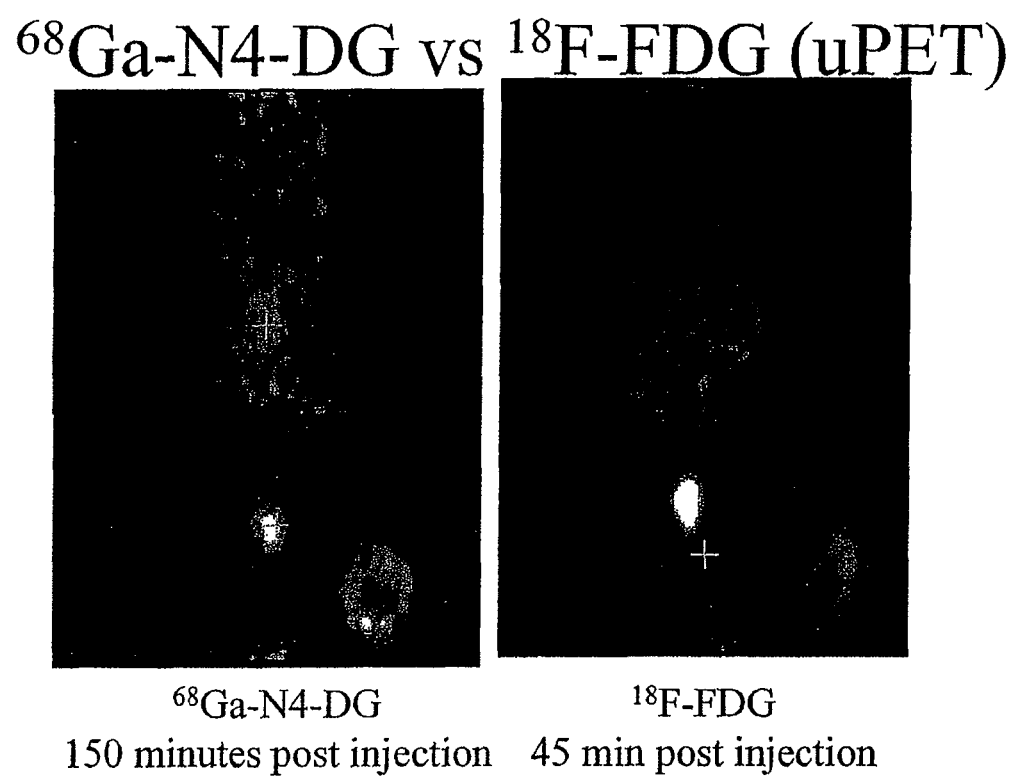
FIGS. 5A-B.
Figure 5B:
Figure 6:
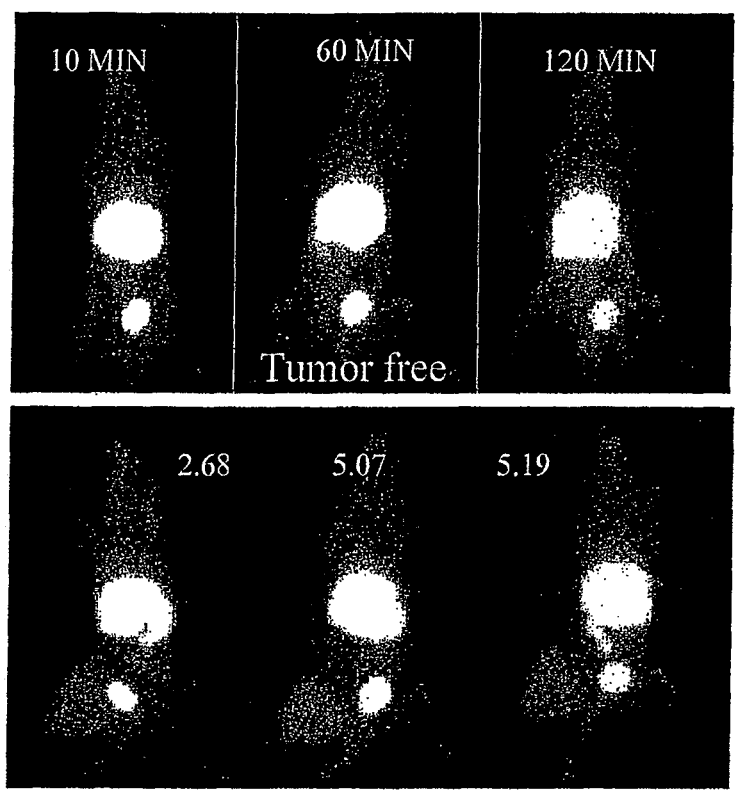
FIG. 6. 10, 60 and 120 min $^{99m}Tc$—$N_4$-DG (cyclam) imaging in rats with and without tumor. 10, 60, and 120 min planar scintigraphy of $^{99m}Tc$—$N_4$-DG in rats with and without tumor (breast tumor cell line) after 300 µCi/rat, i.v. injection, acquired 500,000 count to demonstrate tumor visualization. Tumor-to-non tumor ratios are shown. T=tumor and M=muscle.
Figure 7:
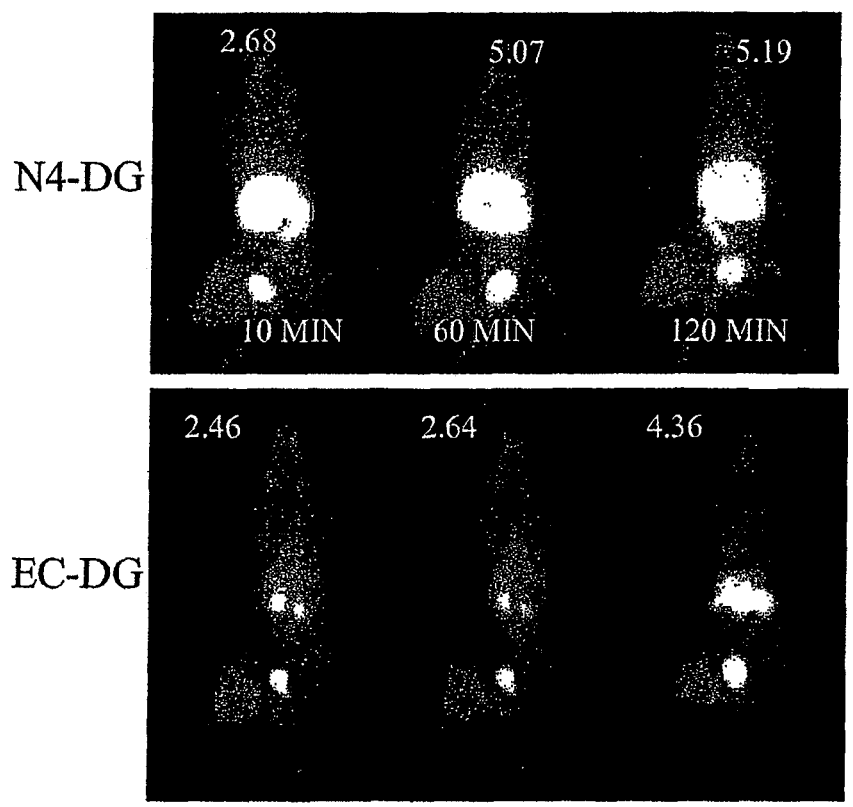
FIG. 7. 10, 60 and 120 min comparison of $^{99m}Tc$—$N_4$-DG (cyclam) & $^{99m}Tc$-EC-DG image of breast tumor cell line bearing rats. 60, and 120 min planar scintigraphy of $^{99m}Tc$—$N_4$-DG & $^{99m}Tc$-EC-DG comparison in breast tumor cell line bearing rats. (300 µCi/rat, i.v. injection, acquired 500,000 count). Tumor-to-non tumor ratios are shown. T=tumor and M=muscle.

In Vitro Cellular Uptake of $^{99m}$Tc—$N_4$-DG ($N_4$-DG-cyclam) and $^{68}$Ga—$N_4$-DG-cyclal Two different cancer cell lines (human lung NSCLC A549, breast 13762) were used for cellular uptake assays. The cell lines were obtained from American Type Culture Collection (Rockville, Md.). The cells were plated to a 12 well tissue culture plate that contained 50,000 cells per each well. 4 μCi (0.148 MBq) of $^{99m}$Tc— and $^{68}$Ga—$N_4$-DG or $N_4$ (0.1 mg/well) was added to each well. Cells were incubated with radiotracers at 37° C. at different time intervals. After incubation, cells were washed with ice-cold phosphate-buffered saline (PBS) twice and trypsinized with 0.5 ml of trypsin solution. Then cells were collected and the radioactivity was measured by gamma counter. Data are expressed in mean ±SD percent uptake ratio of three measurements (FIG. 2).

Biodistribution of $^{99m}$Tc—$N_4$-DG in Breast Tumor-Bearing Rats

The animals were housed in the University of Texas M. D. Anderson Cancer Center facility. All protocols involving animals (rats and rabbits [see below]) were approved by the M. D. Anderson Animal Use and Care Committee. Fischer-344 Rats (150±25 g) (Harlan Sprague-Dawley, Indianapolis, Ind.) (n=18) were inoculated subcutaneously with rat breast adenocarcinoma cells ($10^6$ cells/rodent) into the lumber region in legs using 25-gauge needles. The studies were performed 12 to 15 days after inoculation. Tumor sizes of approximately 1 cm were measured. Biodistribution studies using $^{99m}$Tc—$N_4$-DG were conducted. The rodents were divided into three groups, each group representing a time interval (0.5, 2 and 4 hrs, n=3/time point) and containing total 9 rodents per compound. The injection activity was 25±0.5 μCi (0.925±0.019 MBq)/rat. The injected mass of $^{99m}$Tc—$N_4$-DG was 0.1 mg/rodent. Following administration of the radiotracers, the rats were sacrificed and the selected tissues were excised, weighed and counted for radioactivity. The biodistribution of tracer in each sample was calculated as percentage of the injected dose per gram of tissue wet weight (% ID/g). Tumor/nontarget tissue count density ratios were calculated from the corresponding % ID/g values.

Scintigraphic Imaging Studies

Female Fischer 344 rats (150±25 g) (Harlan Sprague-Dawley, Indianapolis, Ind.) were inoculated subcutaneously with 0.1 ml of mammary tumor cells from the 13762 tumor cell line suspension ($10^6$ cells/rat, a tumor cell line specific to Fischer rats) into the hind legs. Imaging studies were performed 12 to 15 days after inoculation. Tumor sizes of approximately 1-1.5 cm were measured. Scintigraphic images were obtained using an M-camera from Siemens Medical Systems (Hoffman Estates, Ill.). The camera was equipped with a low-energy parallel-hole collimator. The field of view is 53.3 cm×38.7 cm. The intrinsic spatial resolution is 3.2 mm and the pixel size is 19.18 mm (32×32, zoom=1) to 0.187 mm (1024×1024, zoom=3.2). With a low-energy, high-resolution collimator (as required with $^{99m}$Tc), the system is designed for a planar sensitivity of at least 172 counts/minute (cpm)/μCi and spatial resolution of 4-20 mm. pPET was used for PET imaging studies (0.5 mCi/rat).

Planar scintigraphy was obtained at immediate, 0.5-4 hrs after i.v. injection of $^{99m}$Tc—$N_4$-DG, or $^{99m}$Tc—$N_4$ (0.3 mCi/rat; 0.1 mg mass/rabbit). To compare the radiotracer accumulation, ROIs (region of interest in counts per pixel) were determined. The ROIs count between tumor and muscle was used to calculate tumor-to-nontumor ratios.

B. Results

In Vitro Cellular Uptake Studies

There was an increased uptake of $^{99m}$Tc— or $^{68Ga}$—$N_4$-DG or $^{99m}$Tc—$N_4$-AMT as a function of incubation time in the cancer cell lines tested (FIG. 2, FIG. 3, FIGS. 4A-C). Uptake of $^{99m}$Tc—$N_4$ as the control group was less that 0.5% at any time point.

Biodistribution and Scintigraphic Imaging Studies

Figure 8:
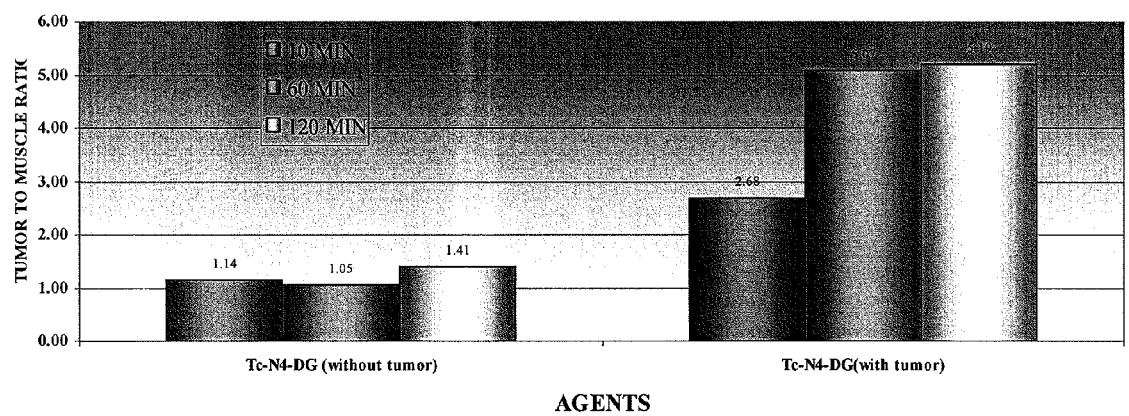
FIG. 8. Tumor-to-muscle count density ratios of $^{99m}$Tc—N$_4$-DG (cyclam) imaging with and without breast cancer cell line bearing rats. Increased tumor-to-muscle ratios was observed with $^{99m}$Tc—N$_4$-DG.
Figure 9:
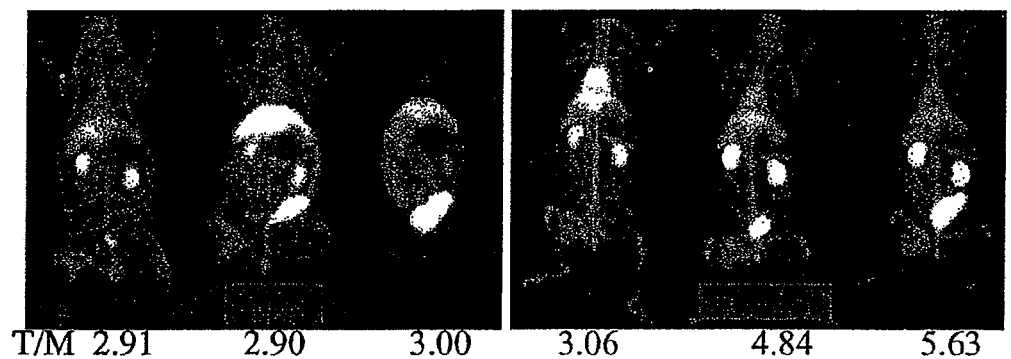
FIG. 9. Comparison of $^{99m}$Tc—N$_4$ & $^{99m}$Tc—N$_4$-AMT (cyclam) imaging in rabbit immediate, 1 hr and 3 hr after injection. Planar scintigraphy of $^{99m}$Tc—N$_4$ & $^{99m}$Tc—N$_4$-AMT in VX2 tumor-bearing rabbits (1 mCi/rabbit, i.v. injection) to compare tumor visualization. Increased tumor/muscle ratios were seen in $^{99m}$Tc—N$_4$-AMT groups.

Biodistribution of $^{99m}$Tc—$N_4$-DG in tumor-bearing rats showed increased tumor-to-tissue count density ratios as a function of time (Table 4). Planar images of tumor-bearing animal models confirmed that the tumors could be visualized clearly with $^{99m}$Tc— or $^{68Ga}$—$N_4$-DG (FIGS. 5A-B, FIG. 6, FIG. 7) and $N_4$-AMT (FIG. 9, FIG. 10). Computer outlined region of interest (ROI) showed that tumor/background ratios in $^{99m}$Tc—$N_4$-DG group were increased as a function of time (FIG. 8). The optimal imaging time was 1 hr in a rat model.

TABLE 4

Biodistribution of $^{99m}$Tc-$N_4$-$DG_2$-(Cyclam) in Breast Tumor-Bearing Rats % of injected dose per gram of tissue weight (n = 3/time, interval, iv)

|  | 30 MIN | 2 HOURS | 4 Hours |
| --- | --- | --- | --- |
| BLOOD | 4.102 ± 0.560 | 1.185 ± 0.154 | 0.984 ± 0.034 |
| HEART | 0.847 ± 0.069 | 0.306 ± 0.017 | 0.253 ± 0.018 |
| LUNG | 3.659 ± 0.212 | 2.368 ± 0.050 | 3.196 ± 0.395 |
| LIVER | 20.959 ± 3.548 | 24.282 ± 0.723 | 26.653 ± 2.338 |
| SPLEEN | 8.535 ± 0.886 | 16.647 ± 3.310 | 11.962 ± 0.655 |
| KIDNEY | 6.995 ± 0.464 | 7.512 ± 0.643 | 8.405 ± 0.146 |
| INTESTINE | 0.626 ± 0.147 | 0.454 ± 0.124 | 0.256 ± 0.033 |
| UTERUS | 0.575 ± 0.067 | 0.294 ± 0.032 | 0.230 ± 0.002 |
| MUSCLE | 0.122 ± 0.021 | 0.060 ± 0.007 | 0.048 ± 0.002 |
| TUMOR | 0.624 ± 0.050 | 0.345 ± 0.019 | 0.274 ± 0.020 |
| THYROID | 1.285 ± 0.298 | 0.485 ± 0.075 | 0.314 ± 0.031 |
| STOMACH | 0.547 ± 0.033 | 0.331 ± 0.038 | 0.216 ± 0.003 |
| T/MUSCLE | 5.348 ± 1.347 | 6.010 ± 1.111 | 5.723 ± 0.079 |
| T/BLOOD | 0.157 ± 0.033 | 0.297 ± 0.023 | 0.279 ± 0.026 |

TABLE 4-continued

Biodistribution of $^{99m}$Tc-N$_4$-DG$_2$-(Cyclam) in Breast Tumor-Bearing Rats
% of injected dose per gram of tissue weight (n = 3/time, interval, iv)

|  | 30 MIN | 2 HOURS | 4 Hours |
|---|---|---|---|
| H/BLOOD | 0.208 ± 0.012 | 0.264 ± 0.023 | 0.257 ± 0.010 |
| H/MUSCLE | 7.057 ± 0.802 | 5.328 ± 1.007 | 5.353 ± 0.633 |

The data represent the mean ± standard deviation from 3 animals

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,141,654
U.S. Pat. No. 5,268,163
U.S. Pat. No. 5,648,063
U.S. Pat. No. 5,880,281
U.S. Pat. No. 5,955,053
U.S. Pat. No. 5,986,074
U.S. Pat. No. 6,692,724
U.S. Pat. No. 6,071,490
U.S. Pat. No. 6,613,305
AU Appln. 01/75210A5
PCT Appln. WO 01/80906A2
PCT Appln. WO 01/91807A2
PCT Appln. WO 91/16076A1
Alauddin and Conti, *Nucl. Med. Biol.*, 25(3):175-180 1998.
Alauddin et al., *J. Nucl. Med.*, 42(11):1682-1690, 2001.
Alauddin et al., *Nucl. Med. Biol.*, 23(6):787-792 1996.
Alauddin et al., *Nucl. Med. Biol.*, 26:371-376, 1999.
Alberico et al., *Surg. Oncol. Clin. N. Am.*, 13(1):β-35, 2004.
Angello et al., *Am J Cardiol.*, 60:528-533, 1987.
Banner et al, *J. Natl. Cancer Inst.*, 88:140, 1994.
Benveniste and Davies, *Proc. Natl. Acad. Sci. USA*, 70(8): 2276-2280, 1973.
Blondeau et al., *Can. J. Chem.*, 45:49-52, 1967.
Bolhuis et al., *Int. J. Cancer Suppl.*, 7:78-81, 1992.
Borodina et al., *Appl. Environ. Microb.*, 71(5):2294-302, 2005.
Bush et al., *Br. J. Cancer Suppl.*, 37(3):302-306, 1978.
Campbell et al., *Cancer Res.*, 51(19):5329-5338 1991.
Canevari et al., *Hybridoma.*, 12(5):501-507, 1993.
Chasselle et al, *Lancet*, 34B:143, 1995.
Coney et al., *Cancer Res.*, 54(9):2448-2455, 1994.
Connors, *Ann. Oncol.*, 7(5):445-52, 1996.
Davison et al., *Inorg. Chem.*, 20:1629-1632, 1980.
Diamond et al., *J. Biol. Chem.* 253(3):866-871, 1978.
Dische, *Int. J. Radiat. Oncol. Biol. Phys.*, 20(1):147-152, 1991.
Evans et al., *J. Amer. Chem. Soc.*, 112:4011-4030, 1990.
Franklin et al., *Int. J. Cancer Suppl.*, 8:89-95, 1994.
Gambhir et al., *J Nucl. Med.*, 39(11):2003-2011, 1998.
Gambhir et al., *Proc. Natl. Acad. Sci. USA*, 96(5):2333-2338, 1999.
Gambhir et al., *Proc. Natl. Acad. Sci. USA*, 97:2785-2790, 2000.
Gatenby et al., *Int. J. Radiat. Oncol. Biol. Phys.*, 14(5):831-838, 1988.
Ginobbi et al., *Anti-cancer Res.*, 17(1A):29-35, 1997.
Goldsmith, *Sem. Nucl. Med.*, 27:85-93, 1997.
Gray et al., *Nature*, 182(4640):952-953, 1958.
Greene and Wuts, In: *Protective Groups in Organic Synthesis*, John Wiley & Sons, New York, 1999.
Gutman et al., *Am. Heart J*, 106:989-995, 1983.
Hall et al., *Radiat. Res.*, 114(3):415-424 1988.
Henson et al., *AJNR Am. J. Neuroradiol.*, 25(6):969-972, 2004.
Hoelscher et al., *Spine*, 25(15):1871-7, 2000.
Holm, et al., *APMIS*, 102(11):828-836, 1994.
Hostetler and Hall, *Proc. Natl. Acad. Sci. USA*, 79:1663-1667, 1982.
Hsuch and Dolnick, Biochem. Pharmacol., 45(12):2537-2545, 1993.
Hu, *Proc. Natl. Acad. Sci. USA*, 95; 9791-95, 1998.
Iyer et al., *J Nucl. Med.*, 42(1):96-105, 2001.
Koh et al., *Int. J. Radiat. Oncol. Biol. Phys.*, 22:199-212, 1992.
Kranz et al., *Proc. Natl. Acad. Sci. USA*, 92(20):9057-61, 1995.
Kundra et al., *J. Nucl. Med.*, 43(3):406-412, 2002.
Leamon and Low, *Biochem. J*, 291 (Pt 3):855-60, 1993.
Leamon and Low, *J. Biol. Chem.*, 267(35):24966-71, 1992.
Leamon and Low, *Proc. Natl. Acad. Sci. USA*, 88(13):5572-76 1991.
Lee and Low, *J. Biol. Chem.*, 269(5):3198-3204, 1994.
Martin et al., *J. Nucl. Med.*, 30:194-201, 1989.
Mathias et al., *J. Nucl. Med.*, 37:1003-1008, 1996.
Mathias et al., *J. Nucl. Med.*, 38:133P, 1997b.
Mathias et al., *J. Nucl. Med.*, 38:87P, 1997a.
Medical Letter, 34:78, 1992.
Michalik et al., *Pharmacol Res.* 21(4):405-414, 1989.
Murakami et al., *Bone*, 21(5):411-418, 1997.
Murakami et al., *J Orthop Res.*, 14(5):742-8, 1996.
Myszka et al., *Carb. Res.*, 338:133-141, 2003.
Nakae and Nakae, *Antimicrobial Agents and Chemo.*, October; 22(4):554-59, 1982.
Namavari et al., *Nucl. Med. Biol.*, 27(2):157-162 2000.
Nordsmark et al., *Radiother. Oncol.*, 41(1):31-39, 1996.
Orr et al., *J. Natl. Cancer Inst.*, 87(4):299-303, 1995.
Ozmen et al., *Drug Chem Toxicol.* 28(4):433-45, 2005.
Patrick et al., *J. Neurooncol.*, 32(2):111-23, 1997.
Pohost et al., *Circulation*, 55:294-302, 1977.
Pu et al., *J. Amer. Chem. Soc.*, 56:1280-1283, 1991.
Rasey et al., *Int. J. Radiat. Oncol. Biol. Phys.*, 17(5):985-91 1989.
Rasey et al., *Radiother. Oncol.*, 17(2):167-73, 1990.
Reed, *Cancer Cell*, 3:17-22, 2003.
Remington's Pharmaceutical Sciences, 18th Ed. Mack Printing Company, 1289-1329, 1990.
Ross et al., *Cancer*, 73(9):2432-43, 1994.
Saha et al., *Semin. Nucl. Med.*, 24(4):324-49, 1994.
Seabold et al., *J. Nucl. Med.*, 40(9):1434-1440, 1999.
Srivastava et al., *J. Tox. Env. Health*, 47:173-182, 1996.
Strunk and Schild, *Eur. Radiol.*, 14(6):1055-1062, 2004.

Surma et al., *Nucl. Med. Comm.*, 15:628-635, 1994.
Tachibana et al., *Biochem. Pharmacol.* 25(20):2297-301, 1976.
Tjuvajev et al., *J. Nucl. Med.*, 43(8):1072-1083, 2002.
Tod et al., *Clin Pharmacokinet.*, March; 38(3):205-223, 2000.
Valk et al., *J. Nucl. Med.*, 33(12):2133-2137, 1992.
Van Nerom et al., *Eur. J. Nucl. Med.*, 16:417, 1990.
Van Nerom et al., *Eur. J. Nucl. Med.*, 20:738-746, 1993.
Verbruggen et al., *Eur. J. Nucl. Med.*, 16:429, 1990.
Verbruggen et al., *J. Nucl. Med.*, 33:551-557, 1992.
Warrell, Jr et al, *N. Engl. J. Med.*, 329(3):177-189, 1993.
Weitman et al., *Cancer Res.*, 52(12):3396-3401 1992b.
Weitman et al., *Cancer Res.*, 52(23):6708-6711, 1992a.
Weitman et al., *J Neurooncol.*, 21(2):107-112, 1994.
Westerhof et al., *Cancer Res.*, 51(20):5507-5513, 1991.
Williams et al., *J. Amer. Chem. Soc.*, 113:9276-9286, 1991.
Williams, In: *Synthesis of Optically Active .alpha.-Amino Acids*, Pergamon Press, 1989.
Yaghoubi et al., *J. Nucl. Med.*, 42:1225-1234, 2001.
Yanai et al., *Proc. Natl. Acad. Sci. USA*, 103(25):9661-9666, 2006.
Yang et al., *Anticancer Res.*, 15:2479-2488, 1995.
Yang et al., *Diabetes*, 53:67-73, 2004.

What is claimed is:

1. A compound of formula (I):

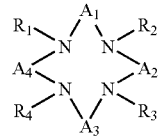 (I)

wherein $A_1$, $A_2$, $A_3$, and $A_4$ are each independently —$(CH_2)_x$—, wherein x=2-4; and
$R_1$, $R_2$, $R_3$, $R_4$ are each independently H, alkyl, substituted alkyl, -alkyl-COOH, a protecting group, a targeting ligand that targets an amino acid transporter, or a linker-targeting ligand that targets an amino acid transporter, provided that $R_1$, $R_2$, $R_3$, and $R_4$ are not all H, not all the same alkyl radical, or not all —$CH_2COOH$;
wherein if $A_1$=—$(CH_2)_2$— and $A_3$=—$(CH_2)_2$—, and either $A_2$ and $A_4$=—$(CH_2)_2$—, or $A_2$ and $A_4$=—$(CH_2)_3$—, then at least one of $R_1$, $R_2$, $R_3$, and $R_4$ is a targeting ligand that targets an amino acid transporter further wherein the targeting ligand is an amino acid or an amino acid derivative.

2. The compound of claim 1, wherein $R_1$, $R_2$, $R_3$ and/or $R_4$ is a linker-targeting ligand.

3. The compound of claim 2, wherein the linker is selected from the group consisting of a peptide, glutamic acid, aspartic acid, bromo ethylacetate, ethylene diamine, lysine and any combination of one or more of these groups.

4. The compound of claim 1, wherein at least one of $R_1$, $R_2$, $R_3$, and $R_4$ is a targeting ligand.

5. The compound of claim 4, wherein $A_1$=—$(CH_2)_2$—, $A_2$=—$(CH_2)_3$—, $A_3$=—$(CH_2)_2$—, and $A_4$=—$(CH_2)_3$—, and at least one of $R_1$, $R_2$, $R_3$, and $R_4$ is a targeting ligand.

6. The compound of claim 4, wherein $A_1$=—$(CH_2)_2$—, $A_2$=—$(CH_2)_2$—, $A_3$=—$(CH_2)_2$—, and $A_4$=—$(CH_2)_2$—, and at least one of $R_1$, $R_2$, $R_3$, and $R_4$ is a targeting ligand.

7. The compound of claim 1, wherein $A_1$=—$(CH_2)_2$—, $A_3$=—$(CH_2)_2$—, $A_2$=—$(CH_2)_3$—, and $A_4$=—$(CH_2)_3$—, and at least one of $R_1$, $R_2$, $R_3$, and $R_4$ is a protecting group.

8. The compound of claim 7, wherein the protecting group is ethyl trifluoroacetate.

9. The compound of claim 1, wherein $A_1$=—$(CH_2)_2$—, $A_2$=—$(CH_2)_2$—, $A_3$=—$(CH_2)_2$—, and $A_4$=—$(CH_2)_2$—, and at least one of $R_1$, $R_2$, $R_3$, and $R_4$ is a protecting group.

10. The compound of claim 9, wherein the protecting group is ethyl trifluoroacetate.

11. The compound of claim 1, wherein $A_1$=—$(CH_2)_3$—, $A_2$=—$(CH_2)_2$—, $A_3$=—$(CH_2)_2$—, and $A_4$=—$(CH_2)_2$—.

12. The compound of claim 1, wherein $A_1$=—$(CH_2)_2$—, $A_2$=—$(CH_2)_3$—, $A_3$=—$(CH_2)_2$—, and $A_4$=—$(CH_2)_3$—.

13. The compound of claim 1, wherein $A_1$=—$(CH_2)_2$—, $A_2$=—$(CH_2)_3$—, $A_3$=—$(CH_2)_3$—, and $A_4$=—$(CH_2)_3$—.

14. The compound of claim 1, wherein $A_1$=—$(CH_2)_3$—, $A_2$=—$(CH_2)_3$—, $A_3$=—$(CH_2)_3$—, and $A_4$=—$(CH_2)_3$—.

15. The compound of claim 1, wherein $A_1$=—$(CH_2)_4$—, $A_2$=—$(CH_2)_3$—, $A_3$=—$(CH_2)_3$—, and $A_4$=—$(CH_2)_3$—.

16. The compound of claim 1, wherein $A_1$=—$(CH_2)_4$—, $A_2$=—$(CH_2)_4$—, $A_3$=—$(CH_2)_3$—, and $A_4$=—$(CH_2)_3$—.

17. The compound of claim 1, wherein $A_1$=—$(CH_2)_3$—, $A_2$=—$(CH_2)_4$—, $A_3$=—$(CH_2)_3$—, and $A_4$=—$(CH_2)_4$—.

18. The compound of claim 1, wherein $A_1$=—$(CH_2)_3$—, $A_2$=—$(CH_2)_4$—, $A_3$=—$(CH_2)_4$—, and $A_4$—$(CH_2)_4$—.

19. The compound of claim 1, wherein $A_1$=—$(CH_2)_4$—, $A_2$=—$(CH_2)_4$—, $A_3$=—$(CH_2)_4$—, and $A_4$=—$(CH_2)_4$—.

20. The compound of claim 1, wherein if $A_1$=—$(CH_2)_2$—, $A_2$=—$(CH_2)_3$—, and $A_3$=—$(CH_2)_2$—, then $A_4$ is not —$(CH_2)_3$—.

21. The compound of claim 1, wherein if $A_1$=—$(CH_2)_2$—, $A_2$=—$(CH_2)_2$—, and $A_3$=—$(CH_2)_2$—, then $A_4$ is not —$(CH_2)_2$.

22. The compound of claim 1, further defined as having the formula:

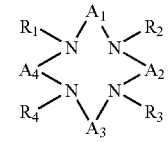

wherein $A_1$, $A_2$, $A_3$, and $A_4$, are each independently —$(CH_2)_x$—, wherein x=2-4;
and $R_1$, $R_2$, and $R_3$ are each independently hydrogen,

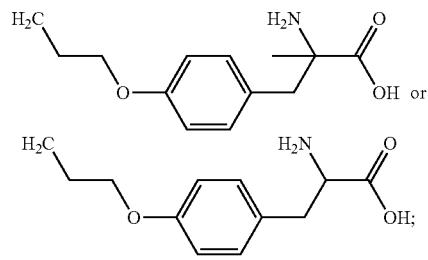

and $R_4$ is chosen from the group consisting of:

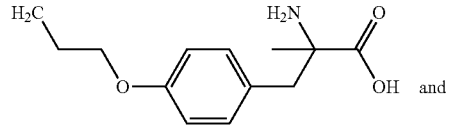

-continued

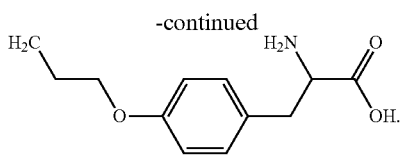

23. The compound of claim 1, wherein the compound is chelated to a metal ion.

24. The compound of claim 23, wherein the metal ion is selected from the group consisting of a technetium ion, a copper ion, an indium ion, a thallium ion, a gallium ion, an arsenic ion, a rhenium ion, a holmium ion, a yttrium ion, a samarium ion, a selenium ion, a strontium ion, a gadolinium ion, a bismuth ion, an iron ion, a manganese ion, a lutecium ion, a cobalt ion, a platinum ion, a calcium ion and a rhodium ion.

25. The compound of claim 23, wherein the metal ion is selected from the group consisting of Tc-99m, Cu-60, Cu-61, Cu-62, Cu-64, Cu-67, In-111, Tl-201, Ga-67, Ga-68, As-72, Re-186, Re-187, Re-188, Ho-166, Y-90, Sm-153, Sr-89, Gd-157, Gd-183, Bi-212, Bi-213, Fe-56, Fe-59, Ac-225, At-211, Ti-45, Mn-55, Lu-177, an iron ion, a manganese ion, a cobalt ion, a platinum ion and a rhodium ion.

26. The compound of claim 23, wherein the metal ion is Re-187.

27. The compound of claim 23, wherein the metal ion is a radionuclide.

28. The compound of claim 27, wherein the radionuclide is selected from the group consisting of $^{99m}$Tc, $^{188}$Re, $^{186}$Re, $^{153}$Sm, $^{166}$Ho, $^{90}$Y, $^{89}$Sr, $^{67}$Ga, $^{68}$Ga, $^{111}$In, $^{183}$Gd, $^{59}$Fe, $^{225}$Ac, $^{212}$Bi, $^{211}$At, $^{45}$Ti, $^{60}$Cu, $^{61}$Cu, $^{67}$Cu, and $^{64}$Cu.

29. The compound of claim 28, wherein the radionuclide is $^{99m}$Tc.

30. The compound of claim 28, wherein the radionuclide is $^{188}$Re.

31. The compound of claim 23, wherein the metal ion is not radioactive.

32. A composition comprising the compound of claim 1 and a pharmaceutically acceptable carrier.

33. The composition of claim 32, wherein the composition further comprises a metal ion chelated to the compound of claim 1.

34. The compound of claim 1, wherein the amino acid or amino acid derivative is serine, tryptophan, tyrosine or a tyrosine derivative.

35. The compound of claim 34, wherein the tyrosine derivative is α-β-tyrosine, tyrosine or α-methyltyrosine.

* * * * *